(12) United States Patent
Subramanian et al.

(10) Patent No.: US 10,329,548 B2
(45) Date of Patent: Jun. 25, 2019

(54) FUNGAL CELLOBIOHYDROLASES

(71) Applicant: Alliance for Sustainable Energy, LLC, Golden, CO (US)

(72) Inventors: Venkataramanan Subramanian, Arvada, CO (US); Michael E. Himmel, Littleton, CO (US); Stephen Robert Decker, Berthoud, CO (US); Gregg Tyler Beckham, Golden, CO (US); Jeffrey G. Linger, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 16/007,797

(22) Filed: Jun. 13, 2018

(65) Prior Publication Data

US 2018/0355333 A1 Dec. 13, 2018

Related U.S. Application Data

(60) Provisional application No. 62/518,754, filed on Jun. 13, 2017.

(51) Int. Cl.
*C12N 9/24* (2006.01)
*C12N 15/00* (2006.01)

(52) U.S. Cl.
CPC .... *C12N 9/2402* (2013.01); *C12Y 302/01091* (2013.01)

(58) Field of Classification Search
CPC .................................. C12N 9/14; C12N 9/42
See application file for complete search history.

(56) References Cited

PUBLICATIONS

Chen et al., "Comparison of Different Mechanical Refining Technologies on the Enzymatic Digestibility of Low Severity Acid Pretreated Corn Stover", Bioresource Technology, 2013, vol. 147, pp. 401-408.

Linger et al., "A Consitutive Expression System for Glycosyl Hydrolase Family 7 Cellobiohydrolases in *Hypocrea jecorina*", Biotechnology for Biofuels, 2015, vol. 8, No. 45, pp. 1-12.

Subramanian et al., "A Random Evolution Approach for Improving Fungal Cellobiohydrolase Activity", Symposium on Biotechnology for Fuels and Chemicals, Poster and Abstract, Apr. 26, 2016, available at https://sim.confex.com/sim/38th/webprogram/Paper31934.html, pp. 1-2.

*Primary Examiner* — Maryam Monshipouri
(74) *Attorney, Agent, or Firm* — Sam J. Barkley; John C. Stolpa

(57) ABSTRACT

Disclosed herein are chimeric Cel7A polypeptides useful for producing biofuels from lignocellulosic biomass.

16 Claims, 33 Drawing Sheets
Specification includes a Sequence Listing.

FIG. 2A (SEQ ID NO: 1)

ATGCTAAGAAGAGCTTTACTATTGAGCTCTTCTGCTATCTTGGCCGTTAAGGCTCAACAAGCCG
GTACCGCTACTGCTGAAAACCACCCTCCATTGACCTGGCAAGAATGTACCGCTCCAGGTTCTTG
TACCACCCAAAACGGTGCTGTCGTCTTGGACGCTAACTGGAGATGGGTCCACGACGTCAACGGT
TACACTAACTGTTACACCGGTAACACCTGGGACCCAACTTACTGTCCAGACGACGAAACTTGCG
CTCAAAACTGTGCCTTGGACGGTGCTGACTACGAAGGTACTTACGGTGTTACCTCCTCTGGTTC
TTCCTTGAAGTTGAACTTCGTCACTGGTTCTAACGTCGGTTCCAGATTGTATTTGTTGCAAGAT
GACTCCACTTACCAAATCTTCAAGTTGTTGAACAGAGAATTTTCTTTCGACGTCGATGTGTCCA
ACTTGCCTTGTGGTTTGAACGGTGCTCTATACTTCGTTGCTATGGACGCTGATGGTGGTGTTTC
CAAGTACCCAAACAACAAGGCTGGTGCCAAATACGGTACTGGTTACTGTGACTCTCAATGTCCA
CGTGACTTGAAGTTTATTGATGGTGAAGCTAATGTCGAAGGTTGGCAACCATCTTCTAACAACG
CTAACACTGGCATCGGTGACCACGGTTCTTGCTGTGCCGAAATGGACGTTTGGGAAGCCAACTC
CATTTCCAACGCCGTCACTCCACACCCATGTGACACTCCAGGTCAAACTATGTGTTCCGGCGAT
GACTGTGGTGGTACTTACTCTAACGATAGATACGCTGGTACCTGTGATCCAGACGGTTGCGACT
TCAATCCATACAGAATGGGTAACACTTCCTTTTACGGTCCAGGCAAGATCATCGACACTACTAA
GCCATTCACTGTTGTCACCCAATTCTTGACCGACGATGGTACTGATACCGGTACTTTGTCCGAA
ATCAAGAGATTCTACATCCAAAACTCTAACGTCATCCCACAACCAAATTCCGACATCTCTGGTG
TCACTGGTAACTCCATTACCACCGAATTTTGTACCGCCCAAAAGCAAGCTTTCGGTGACACCGA
CGACTTCTCTCAACACGGTGGTTTGGCTAAGATGGGTGCTGCTATGCAACAAGGTATGGTTTTG
GTCATGTCTTTGTGGGACGACTACGCTGCTCAAATGTTGTGGTTGGACTCCGATTACCCAACCG
ATGCCGACCCAACCACCCCTGGTATCGCTAGAGGTACCTGTCCAACTGACTCTGGTGTTCCATC
TGACGTCGAATCCCAATCTCCAAACTCCTACGTCACTTACTCCAACATTAAATTCGGTCCAATC
AACTCCACTTTCACTGCTTCTAACCCTCCAGGTGGTAACAGAGGTACTACCACTACTCGTAGGC
CAGCTACTACAACTGGTTCTTCCCCAGGCCCAACCCAATCCCACTACGGTCAATGTGGTGGTAT
CGGTTACTCTGGTCCAACCGTCTGTGCTTCTGGTACTACCTGTCAAGTTTTAAACCCATACTAC
TCTCAATGTTTG

FIG. 2B (SEQ ID NO: 2)

MLRRALLLSSSAILAVKAQQAGTATAENHPPLTWQECTAPGSCTTQNGAVVLDANWRWVHDVNG
YTNCYTGNTWDPTYCPDDETCAQNCALDGADYEGTYGVTSSGSSLKLNFVTGSNVGSRLYLLQD
DSTYQIFKLLNREFSFDVDVSNLPCGLNGALYFVAMDADGGVSKYPNNKAGAKYGTGYCDSQCP
RDLKFIDGEANVEGWQPSSNNANTGIGDHGSCCAEMDVWEANSISNAVTPHPCDTPGQTMCSGD
DCGGTYSNDRYAGTCDPDGCDFNPYRMGNTSFYGPGKIIDTTKPFTVVTQFLTDDGTDTGTLSE
IKRFYIQNSNVIPQPNSDISGVTGNSITTEFCTAQKQAFGDTDDFSQHGGLAKMGAAMQQGMVL
VMSLWDDYAAQMLWLDSDYPTDADPTTPGIARGTCPTDSGVPSDVESQSPNSYVTYSNIKFGPI
NSTFTASNPPGGNRGTTTTRRPATTTGSSPGPTQSHYGQCGGIGYSGPTVCASGTTCQVLNPYY
SQCL

FIG. 3A H1 (SEQ ID NO:3)

ATGCTAAGAAGAGCTTTACTATTGAGCTCTTCTGCTATCTTGGCCGTTAAGGCTCAACAAGCCGGTACCGCTACTAC
TGAAAACCACCCTCCATTGACCTGGCAAGAATGTACCGCTCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGACTACGAAGGTACTTACGGTG
TTACCTCCTCTGGTTCTTCCTTGAAGTTGAACTTCGTCACTGGTTCTAACGTCGGTTCCAGATTGTATTTGTTGCAAG
ATGACTCCACTTACCAAATCTTCAAGTTGTTGAACAGAGAATTTTCTTTCGACGTCGATGTGTCCAACTTGCCTTGT
GGTTTGAACGGTGCTCTATACTTCGTTGCTATGGACGCTGATGGTGGTGTTTCCAAGTACCCAAACAACAAGGCTG
GTGCCAAATACGGTACTGGTTACTGTGACTCTCAATGTCCACGTGACTTGAAGTTTATTGATGGTGAAGCTAATGT
CGAAGGTTGGCAACCATCTTCTAACAACGCTAACACTGGCATCGGTGACCACGGTTCTTGCTGTGCCGAAATGGAC
GTTTGGGAAGCCAACTCCATTTCCAACGCCGTCACTCCACACCCATGTGACACTCCAGGTCAAACTATGTGTTCCGG
CGATGACTGTGGTGGTACTTACTCTAACGATAGATACGCTGGTACCTGTGATCCAGACGGTTGCGACTTCAATCCA
TACAGAATGGGTAACACTTCCTTTTACGGTCCAGGCAAGATCATCGACACTACTAAGCCATTCACTGTTGTCACCCA
ATTCTTGACCGACGATGGTACTGATACCGGTACTTTGTCCGAAATCAAGAGATTCTACATCCAAAACTCTAACGTCA
TCCCACAACCAAATTCCGACATCTCTGGTGTCACTGGTAACTCCATTACCACCGAATTTTGTACCGCCCAAAAGCAA
GCTTTCGGTGACACCGACGACTTCTCTCAACACGGTGGTTTGGCTAAGATGGGTGCTGCTATGCAACAAGGTATG
GTTTTGGTCATGTCTTTGTGGGACGACTACGCTGCTCAAATGTTGTGGTTGGACTCCGATTACCCAACCGATGCCG
ACCCAACCACCCCTGGTATCGCTAGAGGTACCTGTCCAACTGACTCTGGTGTTCCATCGACGTCGAATCCCAATCT
CCAAACTCCTACGTCACTTACTCCAACATTAAATTCGGTCCAATCAACTCCACTTTCACTGCTTCTAACCCTCCAGGT
GGTAACAGAGGTACTACCACTACTCGTAGGCCAGCTACTACAACTGGTTCTTCCCCAGGCCCAACCCAATCCCACT
ACGGTCAATGTGGTGGTATCGGTTACTCTGGTCCAACCGTCTGTGCTTCTGGTACTACCTGTCAAGTTTTAAACCCA
TACTACTCTCAATGTTTGTAG

FIG. 3B H2 (SEQ ID NO: 4)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGCTCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGACTACGAAGGTACTTACGGTG
TTACCTCCTCTGGTTCTTCCTTGAAGTTGAACTTCGTCACTGGTTCTAACGTCGGTTCCAGATTGTATTTGTTGCAAG
ATGACTCCACTTACCAAATCTTCAAGTTGTTGAACAGAGAATTTTCTTTCGACGTCGATGTGTCCAACTTGCCTTGT
GGTTTGAACGGTGCTCTATACTTCGTTGCTATGGACGCTGATGGTGGTGTTTCCAAGTACCCAAACAACAAGGCTG
GTGCCAAATACGGTACTGGTTACTGTGACTCTCAATGTCCACGTGACTTGAAGTTTATTGATGGTGAAGCTAATGT
CGAAGGTTGGCAACCATCTTCTAACAACACTAACACTGGCATAGGTGACCACGGTTCTTGCTGTGCCGAAATGGAC
GTTTGGGAAGCCAACTCCATTTCCAACGCCGTCACTCCACACCCATGTGACACTCCAGGTCAAACTATGTGTTCCGG
CGATGACTGTGGTGGTACTTACTCTAACGATAGATACGCTGGTACCTGTGATCCAGACGGTTGCGACTTCAATCCA
TACAGAATGGGTAACACTTCCTTTTACGGTCCAGGCAAGATCATCGACACTACTAAGCCATTCACTGTTGTCACCCA
ATTCTTGACCGACGATGGTACTGATACCGGTACTTTGTCCGAAATCAAGAGATTCTACATCCAAAACTCTAACGTCA
TCCCACAACCAAATTCCGACATCTCTGGTGTCACTGGTAACTCCATTACCACCGAATTTTGTACCGCCCAAAAGCAA

FIG. 3B continued

GCTTTCGGTGACACCGACGACTTCTCTCAACACGGTGGTTTGGCTAAGATGGGTGCTGCTATGCAACAAGGTATG
GTTTTGGTCATGTCTTTGTGGGACGACTACGCTGCTCAAATGTTGTGGTTGGACTCCGATTACCCAACCGATGCCG
ACCCAACCACCCCTGGTATCGCTAGAGGTACTGTCCAACTGACTCTGGTGTTCCATCTGACGTCGAATCCCAATCTC
CAAACTCCTACGTCACTTACTCCAACATTAAATTCGGTCCAATCAACTCCACTTTCACTGCTTCTAACCCTCCAGGTG
GTAACAGAGGTACTACCACTACTCGTAGGCCAGCTACTACAACTGGTTCTTCCCCAGGCCCAACCCAATCCCACTAC
GGTCAATGTGGTGGTATCGGTTACTCTGGTCCAACCGTCTGTGCTTCTGGTACTACATGTCAAGTTTTAAACCCATA
CTACTCTCAATGTTTG

FIG. 3C H3 (SEQ ID NO: 5)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGCTCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGACTACGAAGGTACTTACGGTG
TTACCTCCTCTGGTTCTTCCTTGAAGTTGAACTTCATCACTGGTTCTAACGTCGGTTCCAGATTGTATTTGTTGCAAG
ATGACTCCACTTACCAAATCTTCAAGTTGTTGAACAGAGAATTTTCTTTCGACGTCGATGTGTCCAACTTGCCTTGT
GGTTTGAACGGTGCTCTATACTTCGTTGCTATGGACGCTGATGGTGGTGTTTCCAAGTACCCAAACAACAAGGCTG
GTGCCAAATACGGTACTGGTTACTGTGACTCTCAATGTCCACGTGACTTGAAGTTTATTGATGGTGTAGCTAATGTC
GAAGGTTGGCAACCATCTTCTAACAACGCTAACACTGGCATCGGTGACCACGGTTCTTGCTATGCCGAAATGGACG
TTTGGGAAGCCAACTCCATTTCCAACGCCGTCACTCCACACCCATGTGACACTCCAGGTCAAACTATGTGTTCCGGC
GATGACTGTGGTGGTACTTACTCTAACGATAGATACGCTGGTACCTGTGATCCAGACGGTTGCGACTTCAATCCAT
ACAGAATGGGTAACACTTCCTTTTACGGTCCAGGCAAGATCATCGACACTACTAAGCCATTCACTGTTGTCACCCAA
TTCTTGACCGACGATGGTACTGATACCGGTACTTTGTCCGAAATCAAGAGATTCTACATCCAAAACTCTAACGTCAT
CCCACAACCAAATTCCGACATCTCTGGTGTCACTGGTAACTCCATTACCACCGAATTTTGTACCGCCCAAAAGCAAG
CTTTCGGTGACACCGAAGACTTCTCTCAACACGGTGGTTTGGCTAAGATGGGTGCTGCTATGCAACAAGGTATGGT
TTTGGTCATGTCTTTGTGGGACGACTACGCTGCTCGAATGTTGTGGTTGGACTCCGATTACCCAACCGATGCCGAC
CCAACCACCCCTGGTATCGCTAGAGGTACCTGTCCAACTGACTCTGGTGTTCCATCTGACGTCGAATCCCAATCTCC
AGACTCCTACGTCACTTACTCCAACATTAAATTCGGTCCAATCAACTCCACTTTCACTGCTTCTAACCCTCCAGGTGG
TAACAGAGGTATTACCACTACTCGTAGGCCAGCTACTACAACTGGTTCTTCCCCAGGCCCAACCCAATCCCACTACG
GTCAATGTGGTGGTATCGGTTACTCTGGTCCAACCGTCTATGCTTCTGGTACTACCTATCAAGTTTTAAACCCATAC
TACTCTCAATGTTTG

FIG. 3D H4 (SEQ ID NO: 6)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAAGTACCGCTCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGACTACGAAGGTACTTACGGTG

FIG. 3D continued

TTACCTCCTCTGGTTCTTCCTTGAAGTTGAACTTCGTCACTGGTTCTAACGTCGGTTCCAGATTGTATTTGTTGCAAG
TTGACTCCACTTACCAAATCTTCAAGTTGTTGAACAGAGAATTTTCTTTCGACGTCGATATGTCCAACTTGCCTTGTG
GTTTGAACGGTGCACTATACTTCGTTGCTATGGACGCTGATGGTGGTGTTTCCAAGTACCCAAACAACAAGGCTGG
TGCCAAATACGGTACTGGTTACTGTGACTCTCAATGTCCACGTGACTTGAAGTTTATTGATGGTGAAGCTAATGTC
GAAGGTTGGCAACCATCTTCTAACAACGCTAACACTGGCATCGGTGACCACGGTCTTGCTGTGCCGAAATGGAC
GTTTGGGAAGCCAACTCCATTTCCAACGCCGTCACTCCACACCCATGTGACACTCCAGGTCAAACTATGTGTTCCGG
CGATGACTGTGGTGGTACTTACTCTAACGATAGATACGCTGGTACCTGTGATCCAGACGGTTGCGACTTCAATCCA
TACAGAATGGGTAACACTTACTTTTACGGTCCAGGCAAGATCATCGACACTACTAAGCCATTCACTGTTGTCACCCA
ATTCTTGACCGACTATGGTACTGATACCGGTACTTTGTCCGAAATCAAGAGATTCTACATCCAAAACTCTAACGTCA
TCCCACAACCAAATTCCGACATCTCTGGTGTCACTGGTAACTCCATTACCACCGAATTTTGTACCGCCCAAAAGCAA
GCTTTCGGTGACACCGACGACTTCTCTCAACACGGTGGTTTGGCTAAGATGGGTGCTGCTATGCAACAAGGTATG
GTTTTGGTCATGTCTTTGTGGGACGACTACGCTGCTCAAATGTTGTGGTTGGACTCCGATTACCCAACCGATGCCG
ACCCAACCACCCCTGGTATCGCTAGAGGTACCTGTCCAACTGACTCTGGTGTTCCATCTGACGTCGAATCCCAATCT
CCAAACTCCTACGTCACTTACTCCAACATTAAATTCGGTCCAATCAACTCCACTTTCACTGCTTCTAACCCTCCAGGT
GGTAACAGAGGTACTACCACTACTCGTAGGCCAGCTACTACAACTGGTTCTTCCCCAGGCCCAACCCAATCCCACT
ACGGTCAATGTGGTGGTATCGGTTACTCTGGTCCAACCGTCTGTGCTTCTGGTACTACCTGTCAAGTTTTAAACCCA
TACTACTCTCAATGTTTG

FIG. 3E H5 (SEQ ID NO: 7)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGCTCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGAATACGAAGGTACTTACGGT
GTTACCTCCTCTGGTTCTTCCTTGAAGTTGAACTTCGTCACTGGTTCTAACGTCGGTTCCAGATTGTATTTGTTGCAA
GATGACTCCACTTACCAAATCTTCAAGTTGTTGAACAGAGAATTTTCTTTCGACGTCGATGTGTCCAACTTGCCTTG
TGGTTTGAACGGTGCTCTATACTTCGTTGCTATGGACGCTGATGGTGGTGTTTCCAAGTACCCAAACAACAAGGCT
GGTGCCAAATACGGTACTGGTTACTGTGACTCTCAATGTCCACGTGACTTGAAGTTTATTGATGGTGAAGCTAATG
TCGAAGGTTGGCAACCATCTTCTAACAACGCTAACACTGGCATCGGTGACCACGGTCTTGCTGTGCCGAAATGGA
CGTTTGGGAAGCCAACTCCATTTCCAACGCCGTCACTCCACACCCATGTGACACTCCTGGTCAAACTATGTGTTCCG
GCGATGACTGTGGTGGTACTTACTCTAACGATAGATACGCTAGTACCTGTGATCCAGACGGTTGCGACATCAATCC
ATACAGAATGGGTAACACTTCCTTTTACGGTCCAGGCAAGATCATCGACACTACTAAGCCATTCACTGTTGTCACCC
AATTCTTGACCGACGATGGTATTGATACCGGTACTTTGTCCGACATCAAGAGATTCTACATCCAAAACTCTAACGTC
ATCCCACAACCAAATTCCGACATCTCTGGTGTCACTGGTAACTCCATTACCACCGAATTTTGTACCGCCCAAAAGCA
AGCTTTCGGTGACACCGACGACTTCTCTCAACACGGTGGTTTGGCTAAGATGGGTGCTGCTATGCAACAAGGTATG
GTTTTGGTCAAGTCTTTGTGGGACGACTACGCTGCTCAAATGTTGTGGTTGGACTCCATTACCCAACCGATGCCG
CCCCAATCACCCCTGGTATCACTAGAGATACCTGTCCAACTGACTATGGTGTTCCATCTGACGTCGAATCCCAATCT

FIG. 3E continued

CCAAACTCCTACGTCACTTACTCCAACATTAAATTCGGTCCAATCAACTCCACTATCACTGCTTCTATCCCTCCAGTT
GGTAACTGAGGTACTACCACTACTCGTAGGCCAGCTACTACTACTGGTTCTTCCCCAGGCCCAACCCAATCCCACTA
CTGTCAATGTGGTGGTATCGGTTACTCTGGTCCAACCGTCTGTGCTTCTGGTACTACCTGTCAAGTTTTAAACCCAT
ACTACTCTCAATGTTTG

FIG. 3F H6 (SEQ ID NO: 8)

ATGCTAAGAATAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGATCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGACTACGAAGGTACTTACGATG
TTACCTCCTCTGGTTCTTCCTTGAAGTTGAACTTCGTCACTGGTTCTAACGTCGGTTCCAGATTGTATTTGTTGCAAG
ATGACTCCACCTACCAAATCTTCAAGTTGTTGAACAGAGAATTTTCTTTCGACGTCGATGTGTCCAACTTGCCTTGT
GGTTTGAACGGTGCTCTATACTTCGTTGCTATGGACGCTGATGGTGGTGTTTCCAAGTACCCAAACAACAAGGCTG
GTGCCAAATACGGTACTGGTTACTGTGACTCTCAATGTCCACGTGACTTGAAGTTTATTGATGGTGAAGCTAATGT
CGAAGGTTGGCAACCATCTTCTAACAACGCTAACACTGGCATCGGTGACCACGGTTCTTGCTGTGCCGAAATGGAC
GTTTGGGAAGCCAACTCCATTTCCAACGCCGTCACTCCACACCCATGTGACACTCCAGGTCAAACTATATGTTCCGG
CGATGACTGTGGTGGTACTTACTCTAACGATAGATACGCTGGTACCTGTGATCCAGACGGTTGCGACTTCAATCCA
TACAGAATGGGTAACACTTCCTTTTACGGTCCAGGCAAGATCATCGACACTACTAAGCCATTCACTGTTGTCACCCA
ATTCTTGACCGACGATGGTACTGATACCGGTACTTTGTCCGAAATCAAGAGATTCTACATCCAAAACTCTAACGTCA
TCCCACAACCAAATTCCGACATCTCTGGTGTCACTGGTAACTCCATTACCACCGAATTTTGTACCGCCCAAAAGCAA
GCTTTCGGTGACACCGACGACTTCTCTCAACACGGTGGTTTGGCTAAGATGGGTACTGCTATGCAACAAGGTATGG
TTTTGGTCATGTCTTTGTGGGACGACTACGCTGCTCAAATGTTGTGGTTGGACTCCGATTACCCAACCGATGCCGAC
CCAACCACCCCTGGTATCGCTAGAGGTACCTGTCCAACTGACTCTGGTGTTCCATCTGACGTCGAATCCCAATCTCC
AAACTCCTACGTCACTTACTCCAACATTAAATTCGGTCCAATCAACTCCACTTTCACTGCTTCTAACCCTCCAGGTGG
TAACAGAGGTACTACCACTACTCGTAGGCCAGCTACTGCAACTGGTTCTTCCCCAGGCCCAACCCAATCCCACTAC
GGTCAATGTGGTGGTATCGGTTACTCTGGTCCAACCGTCTGTGCTTCTGGTACTACCTGTCAAGTTTTAAACCCATA
CTACTCTCAATGTTTG

FIG. 3G H8 (SEQ ID NO: 9)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGCTCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGACTACGAAGGTACTTACGGTG
TTACCTCCTCTGGTTCTTCCTTGAAGTTGAACTTCGTCACTGGTTCTAACGTCGGTTCCAGATTGTATTTGTTGCAAG
ATGACTCCACTTACCAAATCTTCAAGTTGTTGAACAGAGAATTTTCTTTCGACGTCGATGTGTCCAACTTGCCTTGT
GGTTTGAACGGTGCTCTATACTTCGTTGCTATGGACGCTGATGGTGGTGTTTCCAAGTACCCAAACAACAAGGCTG
GTGCCAAATACGGTACTGGTTACTGTGACTCTCAATGTCCACGTGACTTGAAGTTTATTGATGGTGAAGCTAATGT

FIG. 3G continued

CGAAGGTTGGCAACCATCATCTAACAACGCTAACACTGGCATCGGTGACCACGGTTCTTGCTGTGCCGAAATGGA
CGTTTGGGAAGCCAACTCCATTTCCAACGCCGTCACTCCACACCCATGTGACACTCCAGGTCAAACTATGTGTTCCG
GCGATGACTGTGGTGGTACTTACTCTAACGATAGATACGCTGGTACCTGTGATCCAGACGGTTGCGACTTCAATCC
ATACAGAATGGGTAACACTTCCTTTTACGGTCCAGGCAAGATCATCGACACTACTAAGCCATTCACTGTTGTCACCC
AATTCTTGACCGACGATGGTACTGATACCGGTACTTTGTCCGAAATCAAGAGATTCTACATCCAAAACTCTAACGTC
ATCCCACAACCAAATTCCGACATCTCTGGTGTCACTGGTAACTCCATTACCACCGAAATTTTGTACCGCCCAAAAGC
AAGCTTTCGGTGACACCGACGACTTCTCTCAACACGGTGGTTTGGCTAAGATGGGTGCTGCTATGCAACAAGGTAT
GGTTTTGGTCATGTCTTTGTGAGACGACTACGCTGCTCAAATGTTGTGGTTGGACTCTGATTACCCAACCGATGCC
GACCCAACCACCCCTGGTATCGCTAGAGGTACCTGTCCAACTGACTCTGGTGTTCCATCTGACGTCGAATCCCAATC
TCCAAACTCCTACGTCACTTACTCCAACATTAAATTCGGTCCAATCAACTCCACTTTCACTGCTCCTAACCATCCAGG
TGGTAACAGAGGTACTACCTCTACTCGTAGGCCAGCTACTACAACTGGTTCTTCCCCAGGCCCAACCCAAACCCACT
ACGGTCAATGTGGTGGTATCGGTTACTCTGGTCCAACCGTCGGTGCTTCTGGTACTACCTGTCAAGTTTTAAACCCA
TACTACTCTCAATGTTTG

FIG. 3H H10 (SEQ ID NO: 10)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGCTCCAGGTTCTTGTACCACCCAAAACGGTGTTGTCGTCT
TGGACGCTAACTGGAGATGGGTCCACGACGTCAACAGTTACACTAACTGTTACACCGGTAACACCTGGGACCCAA
CTTACTGTCCAGACGACGAAACTTGCGCTCAAAACTGTGCCTTGGACGGTGCTGACTACGAAGGTACTTACGGTGT
TACCTCCTCTGGTTCTTCCTTGAAGTTGAACTTCGTCACTGGTCTGACGTCGGTTCCAGATTGTATTTGTTGCAAGA
TGACTCCACTTACCAAATCTTCAAGTTGTTGAACAGAGAATTTTCTTTCGACGTCGATGTGTCCAACTTGCCTTGTG
GTTTGAACGGTGCTCTATACTTCGTTGCTATGGACGCTGATGGTGGTGTTTCCAAGTACCCAAACAACAAGGCTGG
TGCCAAATACGGTACTGGTTACAGTGACTCTCAATGTCCACGTGACTTGAAGTTTAATGATGGTGAAGCTAATGTC
GAAGGTTGGCAACCATATTCTAACAACGCTAACACTGGCATCGGTGACCACGGTTCTTACTGTGCCGAAATGGAC
GTTTGGGAAGCCAACTCCATTTCCAACGCCGTCACTCCACACCCATGTGACACTCCAGGTCAAACTATGTGTTCCGG
CGATGACTGTGGTGGTACTTACTCTAACGATAGATACGCTGGTACCTGTGATCCAGACGGTTGCGACTTCAATCCA
TACAGAATGGGTAACACTTCCTTTTACGGTCCAGGCAAGATCATCGACACTACTAAGCCATTCACTGTTGTCACCCA
ATTCTTGACCGACGATGGTACTGATACCGGTACTTTGTCCGAAATCAAGAGATTCTACATCCAAAACTCTAACGTCA
TCCCACAACCAAATTCCGACATCTCTGGTGTCACTGGTAACTCCATTACCACCGAATTTTGTACCGCCCAAAAGCAA
GCTTTCGGTGACACCGACAACTTCTCTCAACACGGTGGTTNGGCTAAGATGGGTGCTGCTATGCAACAAGGTATG
GTTTTGGTCATGTCTTTGTGGGACGACTACGCTGCTCAAATGTTGTGGTTGGACTCCGATTACCCAACCGATGCCG
ACCCAACCACCCCTGGTATCGCTAGAGGTACCTGTCCAACTGACTCTGGTGTTCCATCTGACGTCGAATCCCAATCT
CCAAACTCCTACGTCACTTACTCCAACATTAAATTCGGTCCAATCAACTCCACTTTCACTGCTTCTAACCCTCCAGGT
GGTAACAGAGGTACTACCACTACTCGTAGGCCAGCTACAACAACTGGTTCTTCCCCAGGCCCAACCCAATCCCACT
ACGGTCAATGTGGTGGTATCGGTTACTCTGGTCCAACCGTCTGTGCTTCTGGTACTACCTGTCAAGTTTTAAACCCA
TACTACTCTCAATGTTTG

FIG. 3I M1 (SEQ ID NO: 11)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGCTCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGACTACGAAGGTACTTACGGTG
TTACCTCCTCTGGTTCTTCCTTGAAGTTGAACTTCGTCACTGGTTCTAACGTCGGTTCCAGATTGTATTTGTTGCAAG
ATGACTCCACTTACCAAATCTTCAAGTTGTTGAACAGAGAATTTTCTTTCGACGTCGATGTGTCCAACTTGCCTTGT
GGTTTGAACGGTGCTCTATACTTCGTTGCTATGGACGCTGATGGTGGTGTTTCCAAGTACCCAAACAACAAGGCTG
GTGCCAAATACGGTACTGGTTACTGTGACTCTCAATGTCCACGTGACTTGAAGTTTATTGATGGTGAAGCTAATGT
CGAAGGTTGGCAACCATCTTCTAACAACGCTAACACTGGCATCGGTGACCACGGTTCTTGCTGTGCCGAAATGGAC
GTTTGGGAAGCCAACTCCATTTCCAACGCCGTCACTCCACACCCATGTGACACTCCAGGTCAAACTATGTGTTCCGG
CGATGACTGTGGTGGTACTTACTCTAACGATAGATACGCTGGTACCTGTGATCCAGACGGTTGCGACTTCAATCCA
TACAGAATGGGTAACACTTCCTTTTACGGTCCAGGCAAGATCATCGACACTACTAAGCCATTCACTGTTGTCACCCA
ATTCTTGACCGACGATGGTACTGATACCGGTACTTTGTCCGAAATCAAGAGATTCTACATCCAAAACTCTAACGTCA
TCCCACAACCAAATTCCGACATCTCTGGTGTCACTGGTAACTCCATTACCACCGGATTTTGTACCGCCCAAAAGCAA
GCTTTCGGTGACACCGACGACTTCTCTCAACACGGTGGTTTGGCTAAGATGGATGCTGCTATGCAACAAGGTATGG
TTTTGGTCATGTCTTTGTGGGATGACTACGCTGCTCAAATGTTGTGGTTGGACTCCGATTACCCAACCGATGCCGAC
CCAACCACCCCTGGTATCGCTAGAGGTACCTGTCCAACTGACTCTGGTGTTCCATCTGACGTCGAATCCCAATCTCC
AAACTCCTACGTCACTTACTCCAACATTAAATTCGGTCCAATCAACTCCACTTTCACTGCTTCTAACCCTCCAGGTGG
TAACAGAGGTACTACCACTACTCGTAGGCCAGCTACTACAACTGGTTCTTCCCCAGGCCCAATCCAATCCCACTACG
GTCAATGTGGTGGTATCGGTTACTCTGGTCCAACCGTCTGTGCTTCTGGTACTACCTGTCAAGTTTTAAACCCATAC
TACTCTCAATGTTTGTAG

FIG. 3J M3 (SEQ ID NO: 12)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGCTCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGACTACGAAGGTACTTACGGTG
TTACCTCCTCTGGTTCTTCCTTGAAGTTGAACTTCGTCACTGGTTCTAACGTCGGTTCCAGATTGTATTTGTTGCAAG
ATGACTCCACTTACCAAATCTTCAAGTTGTTGAACAGAGAATTTTCTTTCGACGTCGATGTGTCCAACTTGCCTTGT
GGTTTGAACGGTGCTCTATACTTCGTTGCTATGGACGCTGATGGTGGTGTTTCCAAGTACCCAAACAACAAGGCTG
GTGCCAAATACGGTACTGGTTACTGTGACTCTCAATGTCCACGTGACTTGAAGTTTATTGATGGTGAAGCTAATGT
CGAAGGTTGGCAACCATCTTCTAACAACGCTAACACTGGCATCGGTGACCACGGTTCTTGCTGTGCCGAAATGGAC
GTTTGGGAAGCCAACTCCATTTCCAACGCCGTCACTCCACACCCATGTGACACTCCAGGTCAAACTATGTGTTCCGG
CGATGACTGTGGTGGTACTTACTCTAACGATAGATACGCTGGTACCTGTGATCCAGACGGTTGCGACTTCAATCCA
TACAGAATGGGTAACACTTCCTTTTACGGTCCAGGCAAGATCATCGACACTACTAAGCCATTCACTGTTGTCACCCA
ATTCTTGACCGACGATGGTACTGATACCGGTACTTTGTCCGAAATCAAGAGATTCTACATCCAAAACTCTAACGTCA

FIG. 3J continued

TCCCACAACCAAATTCCGACATCTCTGGTGTCACTGGTAACTCCATTACCACCGAATTTTGTACCGCCCAAAAGCAA
GCTTTCGGTGACACCGACGACTTCTCTCAACACGGTGGTTTGGCTAAGATGGGTGCTGCTATGCAACAAGGTATG
GTTTTGGTCATGTCTTTGTGGGACGACTACGCTGCTCAAATGTTGTGGTTGGACTCCGATTACCCAACCGATGCCG
ACCCAACCACCCCTGGTATCGCTAGAGGTACCTGTCCAACTGACTCTGGTGTTCCATCTGACGTCGAATCCCAATCT
CCAAACTCCTACGTCACTTACTCCAACATTAAATTCGGTCCAATCAACTCCACTTTCACTGCTTCTAACCCTCCAGGT
GGTAACAGAGGTACTACCACTACTCGTAGGCCAGCTACTACAACTGGTTCTTCCCCAGGCCCAACCCAATCCCACT
ACGGTCAATGTGGTGGTATCGGTTACTCTGGTCCAACCGTCTGTGCTTCTGGTACTACCTGTCAAGTTTTAAACCCA
TACTACTCTCAATGTTTG

FIG. 3K M4 (SEQ ID NO: 13)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGCTCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGACTACGAAGGTACTTACGGTG
TTACCTCCTCTGGTTCTTCCTTGAAGTTGAACTTCGTCACTGGTTCTAACGTCGGTTCCAGATTGTATTTGTTGCAAG
ATGACTCCACTTACCAAATCTTCAAGTTGTTGAACAGAGAATTTTCTTTCGACGTCGATGTGTCCAACTTGCCTTGT
GGTTTGAACGGTGCTCTATACTTCGTTGCTATGGACGCTGATGGTGGTGTTTCCAAGTACCCAAACAACAAGGCTG
GTGCCAAATACGGTACTGGTTACTGTGACTCTCAATGTCCACGTGACTTGAAGTTTATTGATGGTGAAGCTAATGT
CGAAGGTTGGCAACCATCTTCTAACAACGCTAACACTGGCATCGGTGACCACGGTTCTTGCTGTGCCGAAATGGAC
GTTTGGGAAGCCAACTCCATTTCCAACGCCGTCACTCCACACCCATGTGACACTCCAGGTCAAACTATGTGTTCCGG
CGATGACTGTGGTGGTACTTACTCTAACGATAGATACGCTGGTACCTGTGATCCAGACGGTTGCGACTTCAATCCA
TACAGAATGGGTAACACTTCCTTTTACGGTCCAGGCAAGATCATCGACACTACTAAGCCATTCACTGTTGTCACCCA
ATTCTTGACCGACGATGGTACTGATACCGGTACTTTGTCCGAAATCAAGAGATTCTACATCCAAAACTCTAACGTCA
TCCCACAACCAAATTCCGACATCTCTGGTGTCACTGGTAACTCCATTACCACCGAATTTTGTACCGCCCAAAAGCAA
GCTTTCGGTGACACCGACGACTTCTCTCAACACGGTGGTTTGGCTAAGATGGGTGCTGCTATGCAACAAGGTATG
GTTTTGGTCATGTCTTTGTGGGACGACTACGCTGCTCAAATGTTGTGGTTGGACTCCGATTACCCAACCGATGCCG
ACCCAACCACCCCTGGTATCGCTAGAGGTACCTGTCCAACTGACTCTGGTGTTCCATCTGACGTCGAATCCCAATCT
CCAAACTCCTACGTCACTTACTCCAACATTAAATTCGGTCCAATCAACTCCACTTTCACTGCTTCTAACCCTCCAGGT
GGTAACAGAGGTACTACCACTACTCGTAGGCCAGCTACTACAACTGGTTCTTCCCCAGGCCCAACCCAATCCCACT
ACGGTCAATGTGGTGGTATCGGTTACTCTGGTCCAACCGTCTGTGCTTCTGGTACTACCTGTCAAGTTTTAAACCCA
TACTACTCTCAATGTTTG

FIG. 3L M5 (SEQ ID NO: 14)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGCTCCAGGTTCTTGTACCACCCAAAACGGTGCTGTCGTCT
TGGACGCTAACTGGAGATGGGTCCACGACGTCAACGGTTACACTAACTGTTACACCGGTAACACCTGGGACCCAA

FIG. 3L continued

CTTACTGTCCAGACGACGAAACTTGCGCTCAAAACTGTGCCTTGGACGGTGCTGACTACGAAGGTACTTACGGTGT
TACCTCCTCTGGTTCTTCCTTGAAGTTGAACTTCGTCACTGGTTCTAACGTCGGTTCCAGATTGTATTTGTTGCAAGA
TGACTCCACTTACCAAATCTTCAAGTTGTTGAACAGAGAATTTTCTTTCGACGTCGATGTGTCCAACTTGCCTTGTG
GTTTGAACGGTGCTCTATACTTCGTTGCTATGGACGCTGATGGTGGTGTTTCCAAGTACCCAAACAACAAGGCTGG
TGCCAAATACGGTACTGGTTACTGTGACTCTCAATGTCCACGTGACTTGAAGTTTATTGATGGTGAAGCTAATGTC
GAAGGTTGGCAACCATCTTCTAACAACGCTAACACTGGCATCGGTGACCACGGTTCTTGCTGTGCCGAAATGGAC
GTTTGGGAAGCCAACTCCATTTCCAACGCCGTCACTCCACACCCATGTGACACTCCAGGTCAAACTATGTGTTCCGG
CGATGACTGTGGTGGTACTTACTCTAACGATAGATACGCTGGTACCTGTGATCCAGACGGTTGCGACTTCAATCCA
TACAGAATGGGTAACACTTCCTTTTACGGTCCAGGCAAGATCATCGACACTACTAAGCCATTCACTGTTGTCACCCA
ATTCTTGACCGACGATGGTAATGATACCGGTACTTTGTCCGAAATCAAGAGATTCTACATCCAAAACTCTAACGTCA
TCCCACAACCAAATTCCGACATCTCTGGTGTCACTGGTAACTCCATTACCACCGAATTTTGTACCGCCCAAAAGCAA
GCTTTCGGTGACACCGACGACTTCTCTCAACACGGTGGTTTGGCTAAGATGGGTGCTGCTATGCAACAAGGTATG
GTTTTGGTCATGTCTTTGTGGGACGACTACGCTGCTCAAATGTTGTGGTTGGACTCCGATTACCCAACCGATGCCG
ACCCAACCACCCCTGGTATCGCTAGAGGTACCTGTCCAACTGACTCTGGTGTTCCATCTGACGTCGAATCCCAATCT
CCAAAACTCCTACGTCACTTACTCCAACATTAAATTCGGTCCAATCAACTCCACTTTCACTGCTTCTAACCCTCCAGGT
GGTAACAGAGGTACTACCACTACTCGTAGGCCAGCTACTACAACTGGTTCTTCCCCAGGCCCAACCCAATCCCACT
ACGGTCAATGTGGTGGTATCGGTTACTCTGGTCCAACCGTCTGTGCTTCTGGTACTACCTGTCAAGTTTTAAACCCA
TACTACTCTCAATGTTTG

FIG. 3M M6 (SEQ ID NO: 15)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGCTCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGACTACGAAGGTACTTACGGTG
TTACCTCCTCTGGTTCTTCCTTGAAGTTGAACTTCGTCACTGGTTCTAACGTCGGTTCCAGATTGTATTTGTTGCAAG
ATGACTCCACTTACCAAATCTTCAAGTTGTTGAACAGAGAATTTTCTTTCGACGTCGATGTGTCCAACTTGCCTTGT
GGTTTGAACGGTGCTCTATACTTCGTTGCTATGGACGCTGATGGTGGTGTTTCCAAGTACCCAAACAACAAGGCTG
GTGCCAAATACGGTACTGGTTACTGTGACTCTCAATGTCCACGTGACTTGAAGTTTATTGATGGTGAAGCTAATGT
CGAAGGTTGGCAACCATCTTCTAACAACGCTAACACTGGCATCGGTGACCACGGTTCTTGCTGTGCCGAAATGGAC
GTTTGGGAAGCCAACTCCATTTCCAACGCCGTCACTCCACACCCATGTGACACTCCAGGTCAAACTATGTGTTCCGG
CGATGACTGTGGTGGTACTTACTCTAACGATAGATACGCTGGTACCTGTGATCCAGACGGTTGCGACTTCAATCCA
TACAGAATGGGTAACACTTCCTTTTACGGTCCAGGCAAGATCATCGACACTACTAAGCCATTCACTGTTGTCACCCA
ATTCTTGACCGACGATGGTACTGATACCGGTACTTTGTCCGAAATCAAGAGATTCTACATCCAAAACTCTAACGTCA
TCCCACAACCAAATTCCGACATCTCTGGTGTCACTGGTAACTCCATTACCACCGAATTTTGTACCGCCCAAAAGCAA
GCTTTCGGTGACACCGACGACTTCTCTCAACACGGTGGTTTGGCTAAGATGGGTGCTGCTATGCAACAAGGTATG
GTTTTGGTCATGTCTTTGTGGGACGACTACGCTGCTCAAATGTTGTGGTTGGACTCCGATTACCCAACCGATGCCG

FIG. 3M continued

ACCCAACCACCCCTGGTATCGCTAGAGGTACCTGTCCAACTGACTCTGGTGTTCCATCTGACGTCGAATCCCAATCT
CCAAACTCCTACGTCACTTACTCCAACATTAAATTCGGTCCAATCAACTCCACTTTCACTGCTTCTAACCCTCCAGGT
GGTAACAGAGGTACTACCACTACTCGTAGGCCAGCTACTACAACTGGTTCTTCCCTAGGCCCAACCCAATCCCACTA
CGGTCAATGTGGTGGTATCGGTTACTCTGGTCCAACCGTCTGTGCTTCTGGTACTACCTGTCAAGTTTTAAACCCAT
ACTACTCTCAATGTTTG

FIG. 3N M7 (SEQ ID NO: 16)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGCTCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGACTACGAAGGTACTTACGGTG
TTACCTCCTCTGGTTCTTCCTTGAAGTTGAACTTCGTCACTGGTTCTAACGTCGGTTCCAGATTGTATTTGTTGCAAG
ATGACTCCACTTACCAAATCTTCAAGTTGTTGAACAGAGAATTTTCTTTCGACGTCGATGTGTCCAACTTGCCTTGT
GGTTTGAACGGTGCTCTATACTTCGTTGCTATGGACGCTGATGGTGGTGTTTCCAAGTACCCAAACAACAAGGCTG
GTGCCAAATACGGTACTGGTTACTGTGACTCTCAATGTCCACGTGACTTGAAGTTTATTGATGGTGAAGCTAATGT
CGAAGGTTGGCAACCATCTTCTAACAACGCTAACACTGGCATCGGTGACCACGGTTCTTGCTGTGCCGAAATGGAC
GTTTGGGAAGCCAACTCCATTTCCAACGCCGTCACTCCACACCCATGTGACACTCCAGGTCAAACTATGTGTTCCGG
CGATGACTGTGGTGGTACTTACTCTAACGATAGATACGCTGGTACCTGTGATCCAGACGGTTGCGACTTCAATCCA
TACAGAATGGGTAACACTTCCTTTTACGGTCCAGGCAAGATCATCGACACTACTAAGCCATTCACTGTTGTCACCCA
ATTCTTGACCGACGATGGTACTGATACCGGTACTTTGTCCGAAATCAAGAGATTCTACATCCAAAACTCTAACGTCA
TCCCACAACCAAATTCCGACATCTCTGGTGTCACTGGTAACTCCATTACCACCGAATTTTGTACCGCCCAAAAGCAA
GCTTTCGGTGACACCGACGACTTCTCTCAACACGGTGGTTTGGCTAAGATGGGTGCTGCTATGCAACAAGGTATG
GTTTTGGTCATGTCTTTGTGGGACGACTACGCTGCTCAAATGTTGTGGTTGGACTCCGATTACCCAACCGATGCCG
ACCCAACCACCCCTGGTATCGCTAGAGGTACCTGTCCAACTGACTCTGGTGTTCCATCTGACGTCGAATCCCAATCT
CCAAACTCCTACGTCACTTACTCCAACATTAAATTCGGTCCAATCAACTCCACTTTCACTGCTTCTAACCCTCCAGGT
GGTAACAGAGGTACTACCACTACTCGTAGGCCAGCTACTACAACTGGTTCTCCCCAGGCCCAACCCAATCCCACT
ACGGTCAATGTGGTGGTATCGGTTACTCTGGTCCAACCGTCTGTGCTTCTGGTACTACCTGTCAAGTTTTAAACCCA
TACTACTCTCAATGTTTG

FIG. 3O M8 (SEQ ID NO: 17)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGCTCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGACTACGAAGGTACTTACGGTG
TTACCTCCTCTGGTTCTTCCTTGAAGTTGAACTTCGTCACTGGTTCTAACGTCGGTTCCAGATTGTATTTGTTGCAAG
ATGACTCCACTTACCAAATCTTCAAGTTGTTGAACAGAGAATTTTCTTTCGACGTCGATGTGTCCAACTTGCCTTGT

FIG. 3O continued

GGTTTGAACGGTGCTCTATACTTCGTTGCTATGGACGCTGATGGTGGTGTTTCCAAGTACCCAAACAACAAGGCTG
GTGCCAAATACGGTACTGGTTACTGTGACTCTCAATGTCCACGTGACTTGAAGTTTATTGATGGTGAAGCTAATGT
CGAAGGTTGGCAACCATCTTCTAACAACGCTAACACTGGCATCGGTGACCACGGTTCTTGCTGTGCCGAAATGGAC
GTTTGGGAAGCCAACTCCATTTCCAACGCCGTCACTCCACACCCATGTGACACTCCAGGTCAAACTATGTGTTCCGG
CGATGACTGTGGTGGTACTTACTCTAACGATAGATACGCTGGTACCTGTGATCCAGACGGTTGCGACTTCAATCCA
TACAGAATGGGTAACACTTCCTTTTACGGTCCAGGCAAGATCATCGACACTACTAAGCCATTCACTGTTGTCACCCA
ATTCTTGACCGACGATGGTACTGATACCGGTACTTTGTCCGAAATCAAGAGATTCTACATCCAAAACTCTAACGTCA
TCCCACAACCAAATTCCGACATCTCTGGTGTCACTGGTAACTCCATTACCACCGAATTTTGTACCGCCCAAAAGCAA
GCTTTCGGTGACACCGACGACTTCTCTCAACACGGTGGTTTGGCTAAGATGGGTGCTGCTATGCAACAAGGTATG
GTTTTGGTCATGTCTTTGTGGGACGACTACGCTGCTCAAATGTTGTGGTTGGACTCCGATTACCCAACCGATGCCG
ACCCAACCACCCCTGGTATCGCTAGAGGTACCTGTCCAACTGACTCTGGTGTTCCATCTGACGTCGAATCCCAATCT
CCAAACTCCTACGTCACTTACTCCAACATTAAATTCGGTCCAATCAACTCCACTTTCACTGCTTCTAACCCTCCAGGT
GGTAACAGAGGTACTACCACTACTCGTAGGCCAGCTACTACAACTGGTTCTTCCCCAGGCCCAACCCAATCCCACT
ACGGTCAATGTGGTGGTATCGGTTACTCTGGTCCAACCGTCTGTGCTTCTGGTACTACCTGTCAAGTTTTAAACCCA
TACTACTCTCAATGTTTG

FIG. 3P M9 (SEQ ID NO: 18)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTACCGCTCCAGGTTCTTGTACCACCCAAAACGGTGCTGTCGTC
TTGGACGCTAACTGGAGATGGGTCCACGACGTCAACGGTTACACTAACTGTTACACCGGTAACACCTGGGACCCA
ACTTACTGTCCAGACGACGAAACTTGCGCTCAAAACTGTGCCTTGGACGGTGCTGACTACGAAGGTACTTACGGTG
TTACCTCCTCTGGTTCTTCCTTGAAGTTGAACTTCGTCACTGGTTCTAACGTCGGTTCCAGATTGTATTTGTTGCAAG
ATGACTCCACTTACCAAATCTTCAAGTTGTTGAACAGAGAATTTTCTTTCGACGTCGATGTGTCCAACTTGCCTTGT
GGTTTGAACGGTGCTCTATACTTCGTTGCTATGGACGCTGATGGTGGTGTTTCCAAGTACCCAAACAACAAGGCTG
GTGCCAAATACGGTACTGGTTACTGTGACTCTCAATGTCCACGTGACTTGAAGTTTATTGATGGTGAAGCTAATGT
CGAAGGTTGGCAACCATCTTCTAACAACGCTAACACTGGCATCGGTGACCACGGTTCTTGCTGTGCCGAAATGGAC
GTTTGGGAAGCCAACTCCATTTCCAACGCCGTCACTCCACACCCATGTGACACTCAAGGTCAAACTATGTGTTCCG
GCGATGACTGTGGTGGTACTTACTCTAACGATAGATACGCTGGTACCTGTGATCCAGACGGTTGCGACTTCAATCC
ATACAGAATGGGTAACACTTCCTTTTACGGTCCAGGCAAGATCATCGACACTACTAAGCCATTCACTGTTGTCACCC
AATTCTTGACCGACGATGGTACTGATACCGGTACTTTGTCCGAAATCAAGAGATTCTACATCCAAAACTCTAACGTC
ATCCCACAACCAAATTCCGACATCTCTGGTGTCACTGGTAACTCCATTACCACCGAATTTTGTACCGCCCAAAAGCA
AGCTTTCGGTGACACCGACGACTTCTCTCAACACGGTGGTTTGGCTAAGATGGGTGCTGCTATGCAACAAGGTATG
GTTTTGGTCATGTCTTTGTGGGACGACTACGCTGCTCAAATGTTGTGGTTGGACTCCGATTACCCAACCGATGCCG
ACCCAACCACCCCTGGTATCGCTAGAGGTACCTGTCCAACTGACTCTGGTGTTCCATCTGACGTCGAATCCCAATCT
CCAAACTCCTACGTCACTTACTCCAACATTAAATTCGGTCCAATCAACTCCACTTTCACTGCTTCTAACCCTCCAGGT

FIG. 3P continued

GGTAACAGAGGTACTACCACTACTCGTAGGCCAGCTACTACAACTGGTTCTTCCCCAGGCCCAACCCAATCCCACT
ACGGTCAATGTGGTGGTATCGGTTACTCTGGTCCAACCGTCTGTGCTTCTGGTACTACCTGTCAAGTTTTAAACCCA
TACTACTCTCAATGTTTG

FIG. 3Q M10 (SEQ ID NO: 19)

ATGCTAAGAAGAGCTTTACTATTGAGCTCTTCTGCTATCTTGGCCGTTAAGGCTCAACAAGCCGGTACCGCTACTGC
TGAAAACCACCCTCCATTGACCTGGCAAGAATGTATCGCTCCAGGTTCTTGTACCACCCAAAACGGTGCTGTCGTCT
TGGACGCTAACTGGAGATGGGTCCACGACGTCAACGGTTACACTAACTGTTACACCGGTAACACCTGGGACCCAA
CTTACTGTCCAGACGACGAAACTTGCGCTCAAAACTGTGCCTTGGACGGTGCTGACTACGAAGGTACTTACGGTGT
TACCTCCTCTGGTTCTTCCTTGAAGTTGAACTTCGTCACTGGTTCTAACGTCGGTTCCAGATTGTATTTGTTGCAAGA
TGACTCCACTTACCAAATCTTCAAGTTGTTGAACAGAGAATTTTCTTTCGACGTCGATGTGTCCAACTTGCCTTGTG
GTTTGAACGGTGCTCTATACTTCGTTGCTATGGACGCTGATGGTGGTGTTACCAAGTACCCAAACAACAAGGCTGG
TGCCAAATACGGTACTGGTTACTGTGACTCTCAATGTCCACGTGACTTGAAGTTTATTGATGGTGAAGCTAATGTC
GAAGGTTGGCAACCATCTTCTAACAACGCTAACACTGGCATCGGTGACCACGGTTCTTGCTGTCCCGAAATGGACG
TTTGGGAAGCCAACTCCATTTCCAACGCCGTCACTCCACACCCATGTGACACTCCAGGTCAAACTATGTGTTCCGGC
GATGACTGTGGTGGTACTTACTCTAACGATAGATACGCTGGTACCTGTGATCCAGACGGTTGCGACTTCAATCCAT
ACAGAATGGGTAACACTTCCTTTTACGGTCCAGGCAAGATCATCGACACTACTAAGCCATTCACTGTTGTCACCCAA
TTCTTGACCGACGATGATACTGATACCGGTACTTTGTCCGAAATCAAGAGATTCTACATCCAAAACTCTAACGTCAT
CCCACAACCAAATTCCGACATCTCTGGTGTCACTGGTAACTCCATTACCACCGAATTTTGTACCGCCCAAAAGCAAG
CTTTCGATGACACCGACGACTTCTCTCAACACGGTGGTTTGGCTAAGATGGGTGCTGCTATGCAACAAGGTATGGT
TTTGGTCATGTCTTTGTGGGACGACTACGCTGCTCAAATGTTGTGGTTGGACTCCGATTACCCAACCGATGCCGAC
CCAACCACCCCTGGTATCGCTAGAGGTACCTGTCCAACTGACTCTGGTGTTCCATCTGACGTCGAATCCCAATCTCC
AAACTCCTACGTCACTTACTCCAACATTAAATTCGGTCCAATCAACTCCACTTTCACTGCTTCTAACCCTCCAGGTGG
TAACAGAGGTACTACCACTACTCGTAGGCCAGCTACTACAACTGGTTCTTCCCCAGGCCCAACCCAATCCCACTACG
GTCAATGTGGTGGTATCGGTTACTCTGGTCCAACCGTCTGTGCTTCTGGTACTACCTGTCAAGTTTTAAACCCATAC
TACTCTCAATGTTTG

FIG. 4A H1 (SEQ ID NO: 20)

MLRRALLLSSSAILAVKAQQAGTATTENHPPLTWQECTAPGSCTTQNGAVVLDANWRWVHDVNGYTNCYTGNTWD
PTYCPDDETCAQNCALDGADYEGTYGVTSSGSSLKLNFVTGSNVGSRLYLLQDDSTYQIFKLLNREFSFDVDVSNLPCGL
NGALYFVAMDADGGVSKYPNNKAGAKYGTGYCDSQCPRDLKFIDGEANVEGWQPSSNNANTGIGDHGSCCAEMDV
WEANSISNAVTPHPCDTPGQTMCSGDDCGGTYSNDRYAGTCDPDGCDFNPYRMGNTSFYGPGKIIDTTKPFTVVTQF
LTDDGTDTGTLSEIKRFYIQNSNVIPQPNSDISGVTGNSITTEFCTAQKQAFGDTDDFSQHGGLAKMGAAMQQGMVL
VMSLWDDYAAQMLWLDSDYPTDADPTTPGIARGTCPTDSGVPSDVESQSPNSYVTYSNIKFGPINSTFTASNPPGGN
RGTTTTRRPATTTGSSPGPTQSHYGQCGGIGYSGPTVCASGTTCQVLNPYYSQCL

FIG. 4B H2 (SEQ ID NO: 21)

MLRRALLLSSSAILAVKAQQAGTATAENHPPLTWQECTAPGSCTTQNGAVVLDANWRWVHDVNGYTNCYTGNTWD
PTYCPDDETCAQNCALDGADYEGTYGVTSSGSSLKLNFVTGSNVGSRLYLLQDDSTYQIFKLLNREFSFDVDVSNLPCGL
NGALYFVAMDADGGVSKYPNNKAGAKYGTGYCDSQCPRDLKFIDGEANVEGWQPSSNNTNTGIGDHGSCCAEMDV
WEANSISNAVTPHPCDTPGQTMCSGDDCGGTYSNDRYAGTCDPDGCDFNPYRMGNTSFYGPGKIIDTTKPFTVVTQF
LTDDGTDTGTLSEIKRFYIQNSNVIPQPNSDISGVTGNSITTEFCTAQKQAFGDTDDFSQHGGLAKMGAAMQQGMVL
VMSLWDDYAAQMLWLDSDYPTDADPTTPGIARGTVQLTLVFHLTSNPNLQTPTSLTPTLNSVQSTPLSLLLTLQVVTEV
LPLLVGQLLQLVLPQAQPNPTTVNVVVSVTLVQPSVLLVLHVKF*THTTLNV

FIG. 4C H3 (SEQ ID NO: 22)

MLRRALLLSSSAILAVKAQQAGTATAENHPPLTWQECTAPGSCTTQNGAVVLDANWRWVHDVNGYTNCYTGNTWD
PTYCPDDETCAQNCALDGADYEGTYGVTSSGSSLKLNFITGSNVGSRLYLLQDDSTYQIFKLLNREFSFDVDVSNLPCGL
NGALYFVAMDADGGVSKYPNNKAGAKYGTGYCDSQCPRDLKFIDGVANVEGWQPSSNNANTGIGDHGSCYAEMDV
WEANSISNAVTPHPCDTPGQTMCSGDDCGGTYSNDRYAGTCDPDGCDFNPYRMGNTSFYGPGKIIDTTKPFTVVTQF
LTDDGTDTGTLSEIKRFYIQNSNVIPQPNSDISGVTGNSITTEFCTAQKQAFGDTEDFSQHGGLAKMGAAMQQGMVL
VMSLWDDYAARMLWLDSDYPTDADPTTPGIARGTCPTDSGVPSDVESQSPDSYVTYSNIKFGPINSTFTASNPPGGNR
GITTTRRPATTTGSSPGPTQSHYGQCGGIGYSGPTVYASGTTYQVLNPYYSQCL

FIG. 4D H4 (SEQ ID NO: 23)

MLRRALLLSSSAILAVKAQQAGTATAENHPPLTWQESTAPGSCTTQNGAVVLDANWRWVHDVNGYTNCYTGNTWD
PTYCPDDETCAQNCALDGADYEGTYGVTSSGSSLKLNFVTGSNVGSRLYLLQVDSTYQIFKLLNREFSFDVDMSNLPCGL
NGALYFVAMDADGGVSKYPNNKAGAKYGTGYCDSQCPRDLKFIDGEANVEGWQPSSNNANTGIGDHGSCCAEMDV
WEANSISNAVTPHPCDTPGQTMCSGDDCGGTYSNDRYAGTCDPDGCDFNPYRMGNTYFYGPGKIIDTTKPFTVVTQF
LTDYGTDTGTLSEIKRFYIQNSNVIPQPNSDISGVTGNSITTEFCTAQKQAFGDTDDFSQHGGLAKMGAAMQQGMVL
VMSLWDDYAAQMLWLDSDYPTDADPTTPGIARGTCPTDSGVPSDVESQSPNSYVTYSNIKFGPINSTFTASNPPGGN
RGTTTTRRPATTTGSSPGPTQSHYGQCGGIGYSGPTVCASGTTCQVLNPYYSQCL

FIG. 4E H5 (SEQ ID NO: 24)

MLRRALLLSSSAILAVKAQQAGTATAENHPPLTWQECTAPGSCTTQNGAVVLDANWRWVHDVNGYTNCYTGNTWD
PTYCPDDETCAQNCALDGAEYEGTYGVTSSGSSLKLNFVTGSNVGSRLYLLQDDSTYQIFKLLNREFSFDVDVSNLPCGL
NGALYFVAMDADGGVSKYPNNKAGAKYGTGYCDSQCPRDLKFIDGEANVEGWQPSSNNANTGIGDHGSCCAEMDV
WEANSISNAVTPHPCDTPGQTMCSGDDCGGTYSNDRYASTCDPDGCDINPYRMGNTSFYGPGKIIDTTKPFTVVTQFL
TDDGIDTGTLSDIKRFYIQNSNVIPQPNSDISGVTGNSITTEFCTAQKQAFGDTDDFSQHGGLAKMGAAMQQGMVLV
KSLWDDYAAQMLWLDSHYPTDAAPITPGITRDTCPTDYGVPSDVESQSPNSYVTYSNIKFGPINSTITASIPPVGN*GTT
TTRRPATTTGSSPGPTQSHYCQCGGIGYSGPTVCASGTTCQVLNPYYSQCL

FIG. 4F H6 (SEQ ID NO: 25)

MLRIALLLSSSAILAVKAQQAGTATAENHPPLTWQECTDPGSCTTQNGAVVLDANWRWVHDVNGYTNCYTGNTWD
PTYCPDDETCAQNCALDGADYEGTYDVTSSGSSLKLNFVTGSNVGSRLYLLQDDSTYQIFKLLNREFSFDVDVSNLPCGL
NGALYFVAMDADGGVSKYPNNKAGAKYGTGYCDSQCPRDLKFIDGEANVEGWQPSSNNANTGIGDHGSCCAEMDV
WEANSISNAVTPHPCDTPGQTICSGDDCGGTYSNDRYAGTCDPDGCDFNPYRMGNTSFYGPGKIIDTTKPFTVVTQFL
TDDGTDTGTLSEIKRFYIQNSNVIPQPNSDISGVTGNSITTEFCTAQKQAFGDTDDFSQHGGLAKMGTAMQQGMVLV
MSLWDDYAAQMLWLDSDYPTDADPTTPGIARGTCPTDSGVPSDVESQSPNSYVTYSNIKFGPINSTFTASNPPGGNR
GTTTTRRPATATGSSPGPTQSHYGQCGGIGYSGPTVCASGTTCQVLNPYYSQCL

FIG. 4G H8 (SEQ ID NO: 26)

MLRRALLLSSSAILAVKAQQAGTATAENHPPLTWQECTAPGSCTTQNGAVVLDANWRWVHDVNGYTNCYTGNTWD
PTYCPDDETCAQNCALDGADYEGTYGVTSSGSSLKLNFVTGSNVGSRLYLLQDDSTYQIFKLLNREFSFDVDVSNLPCGL
NGALYFVAMDADGGVSKYPNNKAGAKYGTGYCDSQCPRDLKFIDGEANVEGWQPSSNNANTGIGDHGSCCAEMDV
WEANSISNAVTPHPCDTPGQTMCSGDDCGGTYSNDRYAGTCDPDGCDFNPYRMGNTSFYGPGKIIDTTKPFTVVTQF
LTDDGTDTGTLSEIKRFYIQNSNVIPQPNSDISGVTGNSITTE<u>LYRPKASFR*HRRLLSTRWFG*DGCCYATRYGFGHVFV
RRLRCSNVVVGL*LPNRCRPNHPWYR*RYLSN*LWCSI*RRIPISKLLRHLLQH*IRSNQLHFHCS*PSRW*QRYYLYS*A
SYYNWFFPRPNPNPLRSMWWYRLLWSNRRCFWYYLSSFKPILLSMF</u>

FIG. 4H H10 (SEQ ID NO: 27)

MLRRALLLSSSAILAVKAQQAGTATAENHPPLTWQECTAPGSCTTQNGVVVLDANWRWVHDVNSYTNCYTGNTWD
PTYCPDDETCAQNCALDGADYEGTYGVTSSGSSLKLNFVTGSDVGSRLYLLQDDSTYQIFKLLNREFSFDVDVSNLPCGL
NGALYFVAMDADGGVSKYPNNKAGAKYGTGYSDSQCPRDLKFNDGEANVEGWQPYSNNANTGIGDHGSYCAEMD
VWEANSISNAVTPHPCDTPGQTMCSGDDCGGTYSNDRYAGTCDPDGCDFNPYRMGNTSFYGPGKIIDTTKPFTVVT
QFLTDDGTDTGTLSEIKRFYIQNSNVIPQPNSDISGVTGNSITTEFCTAQKQAFGDTDNFSQHGGXAKMGAAMQQGM
VLVMSLWDDYAAQMLWLDSDYPTDADPTTPGIARGTCPTDSGVPSDVESQSPNSYVTYSNIKFGPINSTFTASNPPGG
NRGTTTTRRPATTTGSSPGPTQSHYGQCGGIGYSGPTVCASGTTCQVLNPYYSQCL

FIG. 4I M1 (SEQ ID NO: 28)

MLRRALLLSSSAILAVKAQQAGTATAENHPPLTWQECTAPGSCTTQNGAVVLDANWRWVHDVNGYTNCYTGNTWD
PTYCPDDETCAQNCALDGADYEGTYGVTSSGSSLKLNFVTGSNVGSRLYLLQDDSTYQIFKLLNREFSFDVDVSNLPCGL
NGALYFVAMDADGGVSKYPNNKAGAKYGTGYCDSQCPRDLKFIDGEANVEGWQPSSNNANTGIGDHGSCCAEMDV
WEANSISNAVTPHPCDTPGQTMCSGDDCGGTYSNDRYAGTCDPDGCDFNPYRMGNTSFYGPGKIIDTTKPFTVVTQF
LTDDGTDTGTLSEIKRFYIQNSNVIPQPNSDISGVTGNSITTGFCTAQKQAFGDTDDFSQHGGLAKMDAAMQQGMVL
VMSLWDDYAAQMLWLDSDYPTDADPTTPGIARGTCPTDSGVPSDVESQSPNSYVTYSNIKFGPINSTFTASNPPGGN
RGTTTTRRPATTTGSSPGPIQSHYGQCGGIGYSGPTVCASGTTCQVLNPYYSQCL

FIG. 4J M3 (SEQ ID NO: 29)

MLRRALLLSSSAILAVKAQQAGTATAENHPPLTWQECTAPGSCTTQNGAVVLDANWRWVHDVNGYTNCYTGNTWD
PTYCPDDETCAQNCALDGADYEGTYGVTSSGSSLKLNFVTGSNVGSRLYLLQDDSTYQIFKLLNREFSFDVDVSNLPCGL
NGALYFVAMDADGGVSKYPNNKAGAKYGTGYCDSQCPRDLKFIDGEANVEGWQPSSNNANTGIGDHGSCCAEMDV
WEANSISNAVTPHPCDTPGQTMCSGDDCGGTYSNDRYAGTCDPDGCDFNPYRMGNTSFYGPGKIIDTTKPFTVVTQF
LTDDGTDTGTLSEIKRFYIQNSNVIPQPNSDISGVTGNSITTEFCTAQKQAFGDTDDFSQHGGLAKMGAAMQQGMVL
VMSLWDDYAAQMLWLDSDYPTDADPTTPGIARGTCPTDSGVPSDVESQSPNSYVTYSNIKFGPINSTFTASNPPGGN
RGTTTTRRPATTTGSSPGPTQSHYGQCGGIGYSGPTVCASGTTCQVLNPYYSQCL

FIG. 4K M4 (SEQ ID NO: 30)

MLRRALLLSSSAILAVKAQQAGTATAENHPPLTWQECTAPGSCTTQNGAVVLDANWRWVHDVNGYTNCYTGNTWD
PTYCPDDETCAQNCALDGADYEGTYGVTSSGSSLKLNFVTGSNVGSRLYLLQDDSTYQIFKLLNREFSFDVDVSNLPCGL
NGALYFVAMDADGGVSKYPNNKAGAKYGTGYCDSQCPRDLKFIDGEANVEGWQPSSNNANTGIGDHGSCCAEMDV
WEANSISNAVTPHPCDTPGQTMCSGDDCGGTYSNDRYAGTCDPDGCDFNPYRMGNTSFYGPGKIIDTTKPFTVVTQF
LTDDGTDTGTLSEIKRFYIQNSNVIPQPNSDISGVTGNSITTEFCTAQKQAFGDTDDFSQHGGLAKMGAAMQQGMVL
VMSLWDDYAAQMLWLDSDYPTDADPTTPGIARGTCPTDSGVPSDVESQSPNSYVTYSNIKFGPINSTFTASNPPGGN
RGTTTTRRPATTTGSSPGPTQSHYGQCGGIGYSGPTVCASGTTCQVLNPYYSQCL

FIG. 4L M5 (SEQ ID NO: 31)

MLRRALLLSSSAILAVKAQQAGTATAENHPPLTWQECTAPGSCTTQNSAVVLDANWRWVHDVNGYTNCYTGNTWD
PTYCPDDETCAQNCALDGADYEGTYGVTSSGSSLKLNFVTGSNVGSRLYLLQDDSTYQIFKLLNREFSFDVDVSNLPCGL
NGALYFVAMDADGGVSKYPNNKAGAKYGTGYCDSQCPRDLKFIDGEANVEGWQPSSNNANTGIGDHGSCCAEMDV
WEANSISNAVTPHPCDTPGQTMCSGDDCGGTYSNDRYAGTCDPDGCDFNPYRMGNTSFYGPGKIIDTTKPFTVVTQF
LTDDGNDTGTLSEIKRFYIQNSNVIPQPNSDISGVTGNSITTEFCTAQKQAFGDTDDFSQHGGLAKMGAAMQQGMVL
VMSLWDDYAAQMLWLDSDYPTDADPTTPGIARGTCPTDSGVPSDVESQSPNSYVTYSNIKFGPINSTFTASNPPGGN
RGTTTTRRPATTTGSSPGPTQSHYGQCGGIGYSGPTVCASGTTCQVLNPYYSQCL

FIG. 4M M6 (SEQ ID NO: 32)

MLRRALLLSSSAILAVKAQQAGTATAENHPPLTWQECTAPGSCTTQNGAVVLDANWRWVHDVNGYTNCYTGNTWD
PTYCPDDETCAQNCALDGADYEGTYGVTSSGSSLKLNFVTGSNVGSRLYLLQDDSTYQIFKLLNREFSFDVDVSNLPCGL
NGALYFVAMDADGGVSKYPNNKAGAKYGTGYCDSQCPRDLKFIDGEANVEGWQPSSNNANTGIGDHGSCCAEMDV
WEANSISNAVTPHPCDTPGQTMCSGDDCGGTYSNDRYAGTCDPDGCDFNPYRMGNTSFYGPGKIIDTTKPFTVVTQF
LTDDGTDTGTLSEIKRFYIQNSNVIPQPNSDISGVTGNSITTEFCTAQKQAFGDTDDFSQHGGLAKMGAAMQQGMVL
VMSLWDDYAAQMLWLDSDYPTDADPTTPGIARGTCPTDSGVPSDVESQSPNSYVTYSNIKFGPINSTFTASNPPGGN
RGTTTTRRPATTTGSSLGPTQSHYGQCGGIGYSGPTVCASGTTCQVLNPYYSQCL

FIG. 4N M7 (SEQ ID NO: 33)

MLRRALLLSSSAILAVKAQQAGTATAENHPPLTWQECTAPGSCTTQNGAVVLDANWRWVHDVNGYTNCYTGNTWD
PTYCPDDETCAQNCALDGADYEGTYGVTSSGSSLKLNFVTGSNVGSRLYLLQDDSTYQIFKLLNREFSFDVDVSNLPCGL
NGALYFVAMDADGGVSKYPNNKAGAKYGTGYCDSQCPRDLKFIDGEANVEGWQPSSNNANTGIGDHGSCCAEMDV
WEANSISNAVTPHPCDTPGQTMCSGDDCGGTYSNDRYAGTCDPDGCDFNPYRMGNTSFYGPGKIIDTTKPFTVVTQF
LTDDGTDTGTLSEIKRFYIQNSNVIPQPNSDISGVTGNSITTEFCTAQKQAFGDTDDFSQHGGLAKMGAAMQQGMVL
VMSLWDDYAAQMLWLDSDYPTDADPTTPGIARGTCPTDSGVPSDVESQSPNSYVTYSNIKFGPINSTFTASNPPGGN
RGTTTTRRPATTTGSPPGPTQSHYGQCGGIGYSGPTVCASGTTCQVLNPYYSQCL

FIG. 4O M8 (SEQ ID NO: 34)

MLRRALLLSSSAILAVKAQQAGTATAENHPPLTWQECTAPGSCTTQNGAVVLDANWRWVHDVNGYTNCYTGNTWD
PTYCPDDETCAQNCALDGADYEGTYGVTSSGSSLKLNFVTGSNVGSRLYLLQDDSTYQIFKLLNREFSFDVDVSNLPCGL
NGALYFVAMDADGGVSKYPNNKAGAKYGTGYCDSQCPRDLKFIDGEANVEGWQPSSNNANTGIGDHGSCCAEMDV
WEANSISNAVTPHPCDTPGQTMCSGDDCGGTYSNDRYAGTCDPDGCDFNPYRMGNTSFYGPGKIIDTTKPFTVVTQF
LTDDGTDTGTLSEIKRFYIQNSNVIPQPNSDISGVTGNSITTEFCTAQKQAFGDTDDFSQHGGLAKMGAAMQQGMVL
VMSLWDDYAAQMLWLDSDYPTDADPTTPGIARGTCPTDSGVPSDVESQSPNSYVTYSNIKFGPINSTFTASNPPGGN
RGTTTTRRPATTTGSSPGPTQSHYGQCGGIGYSGPTVCASGTTCQVLNPYYSQCL

FIG. 4P M9 (SEQ ID NO: 35)

MLRRALLLSSSAILAVKAQQAGTATAENHPPLTWQECTAPGSCTTQNGAVVLDANWRWVHDVNGYTNCYTGNTWD
PTYCPDDETCAQNCALDGADYEGTYGVTSSGSSLKLNFVTGSNVGSRLYLLQDDSTYQIFKLLNREFSFDVDVSNLPCGL
NGALYFVAMDADGGVSKYPNNKAGAKYGTGYCDSQCPRDLKFIDGEANVEGWQPSSNNANTGIGDHGSCCAEMDV
WEANSISNAVTPHPCDTQGQTMCSGDDCGGTYSNDRYAGTCDPDGCDFNPYRMGNTSFYGPGKIIDTTKPFTVVTQ
FLTDDGTDTGTLSEIKRFYIQNSNVIPQPNSDISGVTGNSITTEFCTAQKQAFGDTDDFSQHGGLAKMGAAMQQGMV
LVMSLWDDYAAQMLWLDSDYPTDADPTTPGIARGTCPTDSGVPSDVESQSPNSYVTYSNIKFGPINSTFTASNPPGGN
RGTTTTRRPATTTGSSPGPTQSHYGQCGGIGYSGPTVCASGTTCQVLNPYYSQCL

FIG. 4Q M10 (SEQ ID NO: 36)

MLRRALLLSSSAILAVKAQQAGTATAENHPPLTWQECIAPGSCTTQNGAVVLDANWRWVHDVNGYTNCYTGNTWD
PTYCPDDETCAQNCALDGADYEGTYGVTSSGSSLKLNFVTGSNVGSRLYLLQDDSTYQIFKLLNREFSFDVDVSNLPCGL
NGALYFVAMDADGGVTKYPNNKAGAKYGTGYCDSQCPRDLKFIDGEANVEGWQPSSNNANTGIGDHGSCCPEMDV
WEANSISNAVTPHPCDTPGQTMCSGDDCGGTYSNDRYAGTCDPDGCDFNPYRMGNTSFYGPGKIIDTTKPFTVVTQF
LTDDDTDTGTLSEIKRFYIQNSNVIPQPNSDISGVTGNSITTEFCTAQKQAFDDTDDFSQHGGLAKMGAAMQQGMVL
VMSLWDDYAAQMLWLDSDYPTDADPTTPGIARGTCPTDSGVPSDVESQSPNSYVTYSNIKFGPINSTFTASNPPGGN
RGTTTTRRPATTTGSSPGPTQSHYGQCGGIGYSGPTVCASGTTCQVLNPYYSQCL

```
             1        10        20        30        40        50        60
TrCel7A    QSACTLQSETHPPLTWQKCSSGGTCTQQTGSVVIDANWRWTHATNSSTNCYDGNTWSSTL
SDS3T      QSACTLQSETHPPLTWQKCSSGGTCTQQTGSVVIDANWRWTHATNSSTNCYDGNTWSSTL 70        80        90       100       110       120
TrCel7A    CPDNETCAKNCCLDGAAYASTYGVTTSGNSLSIGFVTQSACHVGARLYLMASDTTYQEF
SDS3T      CPDNETCAKNCCLDGAAYASTYGVTTSGNSLSIGFVTQ...HVGARLYLMASDTTYQEF 130       140       150       160       170       180
TrCel7A    TLLGNEFSFDVDVSQLPCGLNGALYFVSMDADGGVSKYPTNTAGAKYGTGYCDSQCPRDL
SDS3T      TLLGNEFSFDVDVSQLPCGLNGALYFVSMDADGGVSKYPTNTAGAKYGTGYCDSQCPRDL 190       200       210       220       230       240
TrCel7A    KFINGQANVEGWEPSSNNANTGIGGHGSCCSEMDIWEANSISEALTPHPCTTVGQEICEG
SDS3T      KFINGQANVEGWEPSSNNANTGIGGHGSCCSEMDIWEANSISEALTPHPCTTVGQEICEG 250       260       270       280       290       300
TrCel7A    DGCGGTYSDNRYGGTCDPDGCDWNPYRLGNTSFYGPGSSFTLDTTKKLTVVTQFETSGAI
SDS3T      DGCGGTYSDNRYGGTCDPDGCDWNPYRLGNTSFYGPGSSFTLDTTKKLTVVTQFETSGAI 310       320       330       340       350       360
TrCel7A    NRYYVQNGVTFQQPNAELGSYSGNELNDDYCTAEEAEFGGSSFSDKGGLTQFKKATSGGM
SDS3T      NRYYVQNGVTFQQPNAELGSYSGNELNDDYCTAEEAEFGGSSFSDKGGLTQFKKATSGGM 370       380       390       400       410       420
TrCel7A    VLVMSLWDDYYANMLWLDSTYPTNETSSTPGAVRGSCSTSSGVPAQVESQSPNAKVTFSN
SDS3T      VLVMSLWDDYYANMLWLDSTYPTNETSSTPGAVRGSCSTSSGVPAQVESQSPNAKVTFSN

430
TrCel7A    IKFGPIGSTGNPSG
SDS3T      IKFGPIGSTGNPSG
```

FIG. 10

|         | 1          10         20         30         40         50         60 |
|---------|---|
| TrCel7A | QACTLQSETHPPLTWQKCSSGGTCTQQTGSVVIDANWRWTHATNSSTNCYDGNTWSST |
| SDS4T   | QACTLQSETHPPLTWQKCSSGGTCTQQTGSVVIDANWRWTHATNSSTNCYDGNTWSST |

|         | 70         80         90        100        110        120 |
|---------|---|
| TrCel7A | CPDNETCAKNCCLDGAAYASTYGVTTSGNSLSIGFVTQSAQKNVGARLYLMASDTTYQE |
| SDS4T   | CPDNETCAKNCCLDGAAYASTYGVTTSGNSLSIGFVTQSAQKNVGARLYLMASDTTYQE |

|         | 130        140        150        160        170        180 |
|---------|---|
| TrCel7A | FTLLGNEFSFDVDVSQLPCGLNGALYFVSMDADGGVSKYPTNTAGAKYGTGYCDSQCPRDL |
| SDS4T   | FTLLGNEFSFDVDVSQLPCGLNGALYFVSMDADGGVSKYPTNTAGAKYGTGYCDSQCPRDL |

|         | 190        200        210        220        230        240 |
|---------|---|
| TrCel7A | KFINGQANVEGWEPSSNNANTGIGGHGSCCSEMDIWEANSISEALTPHPCTTVGQEICEG |
| SDS4T   | KFINGQANVEGWEPSSNNANTGIGGHGSCCSEMDIWEANSISEALTPHPCTTVGQEICEG |

|         | 250        260        270        280        290 |
|---------|---|
| TrCel7A | DGCGGTYSDNRYGGTCDPDGCDWNPYRLGNTSFYGPGSSFTLDTTKKLTVVTQFETSG |
| SDS4T   | DGCGGTYSDNRYGGTCDPDGCDWNPYRLGNTSFYGPGSSFTLDTTKKLTVVTQFETSG |

|         | 300        310        320        330        340        350 |
|---------|---|
| TrCel7A | .....AINRYYVQNGVTFQQPNAELGSYSGNELNDDYCTAEEAEFGGSSFSDKGGLTQ |
| SDS4T   | STDSLSAINRYYVQNGVTFQQPNAELGSYSGNELNDDYCTAEEAEFGGSSFSDKGGLTQ |

|         | 360        370        380        390        400        410 |
|---------|---|
| TrCel7A | FKKATSGGMVLVMSLWDDYYANMLWLDSTYPTNETSSTPGAVRGSCSTSSGVPAQVESQS |
| SDS4T   | FKKATSGGMVLVMSLWDDYYANMLWLDSTYPTNETSSTPGAVRGSCSTSSGVPAQVESQS |

|         | 420        430 |
|---------|---|
| TrCel7A | NAKVTFSNIKFGPIGSTGNPSG |
| SDS4T   | NAKVTFSNIKFGPIGSTGNPSG |

(SEQ ID NO: 37)

MYRKLAVISAFLATARAQSACTLQSETHPPLTWQKCSSGGTCTQQTGSVVIDANWRWT
HATNSSTNCYDGNTWSSTLCPDNETCAKNCCLDGAAYASTYGVTTSGNSLSIGFVTQSA
QKNVGARLYLMASDTTYQEFTLLGNEFSFDVDVSQLPCGLNGALYFVSMDADGGVSK
YPTNTAGAKYGTGYCDSQCPRDLKFINGQANVEGWEPSSNNANTGIGGHGSCCSEMDI
WEANSISEALTPHPCTTVGQEICEGDGCGGTYSDNRYGGTCDPDGCDWNPYRLGNTSF
YGPGSSFTLDTTKKLTVVTQFETSGAINRYYVQNGVTFQQPNAELGSYSGNELNDDYCT
AEEAEFGGSSFSDKGGLTQFKKATSGGMVLVMSLWDDYYANMLWLDSTYPTNETSST
PGAVRGSCSTSSGVPAQVESQSPNAKVTFSNIKFGPIGSTGNPSGGNPPGGNPPGTTTTRR
PATTTGSSPGPTQSHYGQCGGIGYSGPTVCASGTTCQVLNPYYSQCL

FIG. 19

SEQUENCE LISTING

```
<160> NUMBER OF SEQ ID NOS: 37

<210> SEQ ID NO 1
<211> LENGTH: 1548
<212> TYPE: DNA
<213> ORGANISM: Artificial Sequence
<220> FEATURE:
<223> OTHER INFORMATION: CBH1 sequence prior to mutagenesis

<400> SEQUENCE: 1
atgctaagaa gagctttact attgagctct tctgctatct tggccgttaa ggctcaacaa      60
gccggtaccg ctactgctga aaaccaccct ccattgacct ggcaagaatg taccgctcca     120
ggttcttgta ccacccaaaa cggtgctgtc gtcttggacg ctaactggag atgggtccac     180
gacgtcaacg gttacactaa ctgttacacc ggtaacacct gggacccaac ttactgtcca     240
gacgacgaaa cttgcgctca aaactgtgcc ttggacggtg ctgactacga aggtacttac     300
```

```
ggtgttacct cctctggttc ttccttgaag ttgaacttcg tcactggttc taacgtcggt    360
tccagattgt atttgttgca agatgactcc acttaccaaa tcttcaagtt gttgaacaga    420
gaattttctt tcgacgtcga tgtgtccaac ttgccttgtg gtttgaacgg tgctctatac    480
ttcgttgcta tggacgctga tggtggtgtt ccaagtacc caaacaacaa ggctggtgcc     540
aaatacggta ctggttactg tgactctcaa tgtccacgtg acttgaagtt tattgatggt    600
gaagctaatg tcgaaggttg gcaaccatct tctaacaacg ctaacactgg catcggtgac    660
cacggttctt gctgtgccga atggacgtt tgggaagcca actccatttc aacgccgtc     720 actccacacc catgtgacac tccaggtcaa actatgtgtt ccggcgatga ctgtggtggt    780
acttactcta acgatagata cgctggtacc tgtgatccag acggttgcga cttcaatcca    840
tacagaatgg gtaacacttc cttttacggt ccaggcaaga tcatcgacac tactaagcca    900
ttcactgttg tcacccaatt cttgaccgac gatggtactg ataccggtac tttgtccgaa    960
atcaagagat tctacatcca aaactctaac gtcatcccac aaccaaattc cgacatctct   1020
ggtgtcactg gtaactccat taccaccgaa ttttgtaccg cccaaaagca agctttcggt   1080
gacaccgacg acttctctca acacggtggt ttggctaaga tgggtgctgc tatgcaacaa   1140
ggtatggttt tggtcatgtc tttgtgggac gactacgctg ctcaaatgtt gtggttggac   1200
tccgattacc caaccgatgc cgacccaacc acccctggta tcgctagagg tacctgtcca   1260
actgactctg gtgttccatc tgacgtcgaa tcccaatctc caaactccta cgtcacttac   1320
tccaacatta aattcggtcc aatcaactcc actttcactg cttctaaccc tccaggtggt   1380
aacagaggta ctaccactac tcgtaggcca gctactacaa ctggttcttc cccaggccca   1440
acccaatccc actacggtca atgtggtggt atcggttact ctggtccaac cgtctgtgct   1500
tctggtacta cctgtcaagt tttaaaccca tactactctc aatgtttg                1548
```

<210> SEQ ID NO 2
<211> LENGTH: 516
<212> TYPE: PRT
<213> ORGANISM: Artificial Sequence
<220> FEATURE:
<223> OTHER INFORMATION: amino acid sequence of CBH1 before mutagenesis

<400> SEQUENCE: 2

```
Met Leu Arg Arg Ala Leu Leu Leu Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
    50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
    130                 135                 140
```

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
            165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
            195                 200                 205

Pro Ser Ser Asn Asn Ala Asn Thr Gly Ile Gly Asp His Gly Ser Cys
            210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
            275                 280                 285

Tyr Gly Pro Gly Lys Ile Ile Asp Thr Thr Lys Pro Phe Thr Val Val
290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Asp Phe Ser Gln His
            355                 360                 365

Gly Gly Leu Ala Lys Met Gly Ala Ala Met Gln Gln Gly Met Val Leu
            370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
            435                 440                 445

Asn Ser Thr Phe Thr Ala Ser Asn Pro Pro Gly Gly Asn Arg Gly Thr
            450                 455                 460

Thr Thr Thr Arg Arg Pro Ala Thr Thr Thr Gly Ser Ser Pro Gly Pro
465                 470                 475                 480

Thr Gln Ser His Tyr Gly Gln Cys Gly Gly Ile Gly Tyr Ser Gly Pro
            485                 490                 495

Thr Val Cys Ala Ser Gly Thr Thr Cys Gln Val Leu Asn Pro Tyr Tyr
            500                 505                 510

Ser Gln Cys Leu
        515

<210> SEQ ID NO 3
<211> LENGTH: 1551
<212> TYPE: DNA
<213> ORGANISM: Artificial Sequence
<220> FEATURE:

<223> OTHER INFORMATION: non-naturally occurring, mutant CBH sequence

<400> SEQUENCE: 3

| | | | | | |
|---|---|---|---|---|---|
| atgctaagaa | gagctttact | attgagctct | tctgctatct | tggccgttaa | ggctcaacaa | 60 |
| gccggtaccg | ctactactga | aaaccaccct | ccattgacct | ggcaagaatg | taccgctcca | 120 |
| ggttcttgta | ccacccaaaa | cggtgctgtc | gtcttggacg | ctaactggag | atgggtccac | 180 |
| gacgtcaacg | gttacactaa | ctgttacacc | ggtaacacct | gggacccaac | ttactgtcca | 240 |
| gacgacgaaa | cttgcgctca | aaactgtgcc | ttggacggtg | ctgactacga | aggtacttac | 300 |
| ggtgttacct | cctctggttc | ttccttgaag | ttgaacttcg | tcactggttc | taacgtcggt | 360 |
| tccagattgt | atttgttgca | agatgactcc | acttaccaaa | tcttcaagtt | gttgaacaga | 420 |
| gaattttctt | tcgacgtcga | tgtgtccaac | ttgccttgtg | gtttgaacgg | tgctctatac | 480 |
| ttcgttgcta | tggacgctga | tggtggtgtt | tccaagtacc | aaacaacaa | ggctggtgcc | 540 |
| aaatacggta | ctggttactg | tgactctcaa | tgtccacgtg | acttgaagtt | tattgatggt | 600 |
| gaagctaatg | tcgaaggttg | gcaaccatct | tctaacaacg | ctaacactgg | catcggtgac | 660 |
| cacggttctt | gctgtgccga | aatggacgtt | tgggaagcca | actccatttc | caacgccgtc | 720 |
| actccacacc | catgtgacac | tccaggtcaa | actatgtgtt | ccggcgatga | ctgtggtggt | 780 |
| acttactcta | cgatagata | cgctggtacc | tgtgatccag | acggttgcga | cttcaatcca | 840 |
| tacagaatgg | gtaacacttc | cttttacggt | ccaggcaaga | tcatcgacac | tactaagcca | 900 |
| ttcactgttg | tcacccaatt | cttgaccgac | gatggtactg | ataccggtac | tttgtccgaa | 960 |
| atcaagagat | tctacatcca | aaactctaac | gtcatcccac | aaccaaattc | cgacatctct | 1020 |
| ggtgtcactg | gtaactccat | taccaccgaa | ttttgtaccg | cccaaaagca | agctttcggt | 1080 |
| gacaccgacg | acttctctca | acacggtggt | ttggctaaga | tgggtgctgc | tatgcaacaa | 1140 |
| ggtatggttt | tggtcatgtc | tttgtgggac | gactacgctg | ctcaaatgtt | gtggttggac | 1200 |
| tccgattacc | caaccgatgc | cgacccaacc | accctggta | tcgctagagg | tacctgtcca | 1260 |
| actgactctg | gtgttccatc | tgacgtcgaa | tcccaatctc | caaactccta | cgtcacttac | 1320 |
| tccaacatta | aattcggtcc | aatcaactcc | acttcactg | cttctaaccc | tccaggtggt | 1380 |
| aacagaggta | ctaccactac | tcgtaggcca | gctactacaa | ctggttcttc | cccaggccca | 1440 |
| acccaatccc | actacggtca | atgtggtggt | atcggttact | ctggtccaac | cgtctgtgct | 1500 |
| tctggtacta | cctgtcaagt | tttaaaccca | tactactctc | aatgtttgta | g | 1551 |

<210> SEQ ID NO 4
<211> LENGTH: 1547
<212> TYPE: DNA
<213> ORGANISM: Artificial Sequence
<220> FEATURE:
<223> OTHER INFORMATION: non-naturally occurring mutated CBH sequence

<400> SEQUENCE: 4

| | | | | | |
|---|---|---|---|---|---|
| atgctaagaa | gagctttact | attgagctct | tctgctatct | tggccgttaa | ggctcaacaa | 60 |
| gccggtaccg | ctactgctga | aaaccaccct | ccattgacct | ggcaagaatg | taccgctcca | 120 |
| ggttcttgta | ccacccaaaa | cggtgctgtc | gtcttggacg | ctaactggag | atgggtccac | 180 |
| gacgtcaacg | gttacactaa | ctgttacacc | ggtaacacct | gggacccaac | ttactgtcca | 240 |
| gacgacgaaa | cttgcgctca | aaactgtgcc | ttggacggtg | ctgactacga | aggtacttac | 300 |
| ggtgttacct | cctctggttc | ttccttgaag | ttgaacttcg | tcactggttc | taacgtcggt | 360 |
| tccagattgt | atttgttgca | agatgactcc | acttaccaaa | tcttcaagtt | gttgaacaga | 420 |

```
gaattttctt tcgacgtcga tgtgtccaac ttgccttgtg gtttgaacgg tgctctatac    480
ttcgttgcta tggacgctga tggtggtgtt tccaagtacc caaacaacaa ggctggtgcc    540
aaatacggta ctggttactg tgactctcaa tgtccacgtg acttgaagtt tattgatggt    600
gaagctaatg tcgaaggttg gcaaccatct tctaacaaca ctaacactgg cataggtgac    660
cacggttctt gctgtgccga aatggacgtt tgggaagcca actccatttc caacgccgtc    720
actccacacc catgtgacac tccaggtcaa actatgtgtt ccggcgatga ctgtggtggt    780
acttactcta acgatagata cgctggtacc tgtgatccag acggttgcga cttcaatcca    840
tacagaatgg gtaacacttc cttttacggt ccaggcaaga tcatcgacac tactaagcca    900
ttcactgttg tcacccaatt cttgaccgac gatggtactg ataccggtac tttgtccgaa    960
atcaagagat ctacatcca aaactctaac gtcatccac aaccaaattc cgacatctct    1020
ggtgtcactg gtaactccat taccaccgaa ttttgtaccg cccaaaagca agctttcggt    1080
gacaccgacg acttctctca cacggtggt ttggctaaga tgggtgctgc tatgcaacaa    1140
ggtatggttt tggtcatgtc tttgtgggac gactacgctg ctcaaatgtt gtggttggac    1200
tccgattacc caaccgatgc cgacccaacc accctggta tcgctagagg tactgtccaa    1260
ctgactctgg tgttccatct gacgtcgaat cccaatctcc aaactcctac gtcacttact    1320
ccaacattaa attcggtcca atcaactcca ctttcactgc ttctaaccct ccaggtggta    1380
acagaggtac taccactact cgtaggccag ctactacaac tggttcttcc ccaggcccaa    1440
cccaatccca ctacggtcaa tgtggtggta tcggttactc tggtccaacc gtctgtgctt    1500
ctggtactac atgtcaagtt ttaaacccat actactctca atgtttg              1547

<210> SEQ ID NO 5
<211> LENGTH: 1548
<212> TYPE: DNA
<213> ORGANISM: Artificial Sequence
<220> FEATURE:
<223> OTHER INFORMATION: non-naturally occurring mutated CBH

<400> SEQUENCE: 5
atgctaagaa gagctttact attgagctct tctgctatct tggccgttaa ggctcaacaa     60
gccggtaccg ctactgctga aaaccaccct ccattgacct ggcaagaatg taccgctcca    120
ggttcttgta ccacccaaaa cggtgctgtc gtcttggacg ctaactggag atgggtccac    180
gacgtcaacg gttacactaa ctgttacacc ggtaacacct gggacccaac ttactgtcca    240
gacgacgaaa cttgcgctca aaactgtgcc ttggacggtg ctgactacga aggtacttac    300
ggtgttacct cctctggttc ttccttgaag ttgaacttca tcactggttc taacgtcggt    360
tccagattgt atttgttgca agatgactcc acttaccaaa tcttcaagtt gttgaacaga    420
gaattttctt tcgacgtcga tgtgtccaac ttgccttgtg gtttgaacgg tgctctatac    480
ttcgttgcta tggacgctga tggtggtgtt tccaagtacc caaacaacaa ggctggtgcc    540
aaatacggta ctggttactg tgactctcaa tgtccacgtg acttgaagtt tattgatggt    600
gtagctaatg tcgaaggttg gcaaccatct tctaacaacg ctaacactgg catcggtgac    660
cacggttctt gctatgccga aatggacgtt tgggaagcca actccatttc caacgccgtc    720
actccacacc catgtgacac tccaggtcaa actatgtgtt ccggcgatga ctgtggtggt    780
acttactcta acgatagata cgctggtacc tgtgatccag acggttgcga cttcaatcca    840
tacagaatgg gtaacacttc cttttacggt ccaggcaaga tcatcgacac tactaagcca    900
```

```
ttcactgttg tcacccaatt cttgaccgac gatggtactg ataccggtac tttgtccgaa    960
atcaagagat tctacatcca aaactctaac gtcatcccac aaccaaattc cgacatctct   1020
ggtgtcactg gtaactccat taccaccgaa ttttgtaccg cccaaaagca agctttcggt   1080
gacaccgaag acttctctca cacggtggt ttggctaaga tgggtgctgc tatgcaacaa    1140
ggtatggttt tggtcatgtc tttgtgggac gactacgctg ctcgaatgtt gtggttggac   1200
tccgattacc caaccgatgc cgacccaacc acccctggta tcgctagagg tacctgtcca   1260
actgactctg gtgttccatc tgacgtcgaa tcccaatctc cagactccta cgtcacttac   1320
tccaacatta aattcggtcc aatcaactcc actttcactg cttctaaccc tccaggtggt   1380
aacagaggta ttaccactac tcgtaggcca gctactacaa ctggttcttc cccaggccca   1440
acccaatccc actacggtca atgtggtggt atcggttact ctggtccaac cgtctatgct   1500
tctggtacta cctatcaagt tttaaaccca tactactctc aatgtttg               1548

<210> SEQ ID NO 6
<211> LENGTH: 1548
<212> TYPE: DNA
<213> ORGANISM: Artificial Sequence
<220> FEATURE:
<223> OTHER INFORMATION: non-naturally occuring mutated CBH sequence

<400> SEQUENCE: 6
atgctaagaa gagctttact attgagctct tctgctatct tggccgttaa ggctcaacaa     60
gccggtaccg ctactgctga aaaccaccct ccattgacct ggcaagaaag taccgctcca    120
ggttcttgta ccaccccaaaa cggtgctgtc gtccttgacg ctaactggag atgggtccac    180
gacgtcaacg gttacactaa ctgttacacc ggtaacacct gggacccaac ttactgtcca    240
gacgacgaaa cttgcgctca aaactgtgcc ttggacggtg ctgactacga aggtacttac    300
ggtgttacct cctctggttc ttccttgaag ttgaacttcg tcactggttc taacgtcggt    360
tccagattgt atttgttgca agttgactcc acttaccaaa tcttcaagtt gttgaacaga    420
gaattttctt tcgacgtcga tatgtccaac ttgccttgtg gtttgaacgg tgcactatac    480
ttcgttgcta tggacgctga tggtggtgtt tccaagtacc caaacaacaa ggctggtgcc    540
aaatacggta ctggttactg tgactctcaa tgtccacgtg acttgaagtt tattgatggt    600
gaagctaatg tcgaaggttg gcaaccatct tctaacaacg ctaacactgg catcggtgac    660
cacggttctt gctgtgccga aatggacgtt tgggaagcca actccatttc caacgccgtc    720
actccacacc catgtgacac tccaggtcaa actatgtgtt ccggcgatga ctgtggtggt    780
acttactcta acgatagata cgctggtacc tgtgatccag acggttgcga cttcaatcca    840
tacagaatgg gtaacactta cttttacggt ccaggcaaga tcatcgacac tactaagcca    900
ttcactgttg tcacccaatt cttgaccgac tatggtactg ataccggtac tttgtccgaa    960
atcaagagat tctacatcca aaactctaac gtcatcccac aaccaaattc cgacatctct   1020
ggtgtcactg gtaactccat taccaccgaa ttttgtaccg cccaaaagca agctttcggt   1080
gacaccgacg acttctctca cacggtggt ttggctaaga tgggtgctgc tatgcaacaa    1140
ggtatggttt tggtcatgtc tttgtgggac gactacgctg ctcaaatgtt gtggttggac   1200
tccgattacc caaccgatgc cgacccaacc acccctggta tcgctagagg tacctgtcca   1260
actgactctg gtgttccatc tgacgtcgaa tcccaatctc caaactccta cgtcacttac   1320
tccaacatta aattcggtcc aatcaactcc actttcactg cttctaaccc tccaggtggt   1380
aacagaggta ctaccactac tcgtaggcca gctactacaa ctggttcttc cccaggccca   1440
```

```
acccaatccc actacggtca atgtggtggt atcggttact ctggtccaac cgtctgtgct    1500
tctggtacta cctgtcaagt tttaaaccca tactactctc aatgtttg                 1548
```

<210> SEQ ID NO 7
<211> LENGTH: 1548
<212> TYPE: DNA
<213> ORGANISM: Artificial Sequence
<220> FEATURE:
<223> OTHER INFORMATION: non-naturally occurring mutated CBH sequence

<400> SEQUENCE: 7

```
atgctaagaa gagctttact attgagctct tctgctatct tggccgttaa ggctcaacaa     60
gccggtaccg ctactgctga aaaccaccct ccattgacct ggcaagaatg taccgctcca    120
ggttcttgta ccacccaaaa cggtgctgtc gtcttggacg ctaactggag atgggtccac    180
gacgtcaacg gttacactaa ctgttacacc ggtaacacct gggacccaac ttactgtcca    240
gacgacgaaa cttgcgctca aaactgtgcc ttggacggtg ctgaatacga aggtacttac    300
ggtgttacct cctctggttc ttccttgaag ttgaacttcg tcactggttc taacgtcggt    360
tccagattgt atttgttgca agatgactcc acttaccaaa tcttcaagtt gttgaacaga    420
gaattttctt tcgacgtcga tgtgtccaac ttgccttgtg gtttgaacgg tgctctatac    480
ttcgttgcta tggacgctga tggtggtgtt ccaagtacc caaacaacaa ggctggtgcc     540
aaatacggta ctggttactg tgactctcaa tgtccacgtg acttgaagtt tattgatggt    600
gaagctaatg tcgaaggttg gcaaccatct tctaacaacg ctaacactgg catcggtgac    660
cacggttctt gctgtgccga atggacgtt tgggaagcca actccatttc caacgccgtc    720
actccacacc catgtgacac tcctggtcaa actatgtgtt ccggcgatga ctgtggtggt    780
acttactcta cgatagata cgctagtacc tgtgatccag acggttgcga catcaatcca    840
tacagaatgg gtaacacttc cttttacggt ccaggcaaga tcatcgacac tactaagcca    900
ttcactgttg tcacccaatt cttgaccgac gatggtattg ataccggtac tttgtccgac    960
atcaagagat tctacatcca aaactctaac gtcatcccac aaccaaattc cgacatctct   1020
ggtgtcactg gtaactccat taccaccgaa ttttgtaccg cccaaaagca agctttcggt   1080
gacaccgacg acttctctca cacggtggt ttggctaaga tgggtgctgc tatgcaacaa    1140
ggtatggttt tggtcaagtc tttgtgggac gactacgctg ctcaaatgtt gtggttggac   1200
tcccattacc caaccgatgc cgccccaatc accctggta tcactagaga tacctgtcca    1260
actgactatg tgttccatc tgacgtcgaa tcccaatctc caaactccta cgtcacttac    1320
tccaacatta aattcggtcc aatcaactcc actatcactg cttctatccc tccagttggt   1380
aactgaggta ctaccactac tcgtaggcca gctactacta ctggttcttc cccaggccca   1440
acccaatccc actactgtca atgtggtggt atcggttact ctggtccaac cgtctgtgct   1500
tctggtacta cctgtcaagt tttaaaccca tactactctc aatgtttg                1548
```

<210> SEQ ID NO 8
<211> LENGTH: 1548
<212> TYPE: DNA
<213> ORGANISM: Artificial Sequence
<220> FEATURE:
<223> OTHER INFORMATION: non-naturally occurring mutated CBH sequence

<400> SEQUENCE: 8

```
atgctaagaa tagctttact attgagctct tctgctatct tggccgttaa ggctcaacaa     60
```

```
gccggtaccg ctactgctga aaaccaccct ccattgacct ggcaagaatg taccgatcca    120
ggttcttgta ccacccaaaa cggtgctgtc gtcttggacg ctaactggag atgggtccac    180
gacgtcaacg gttacactaa ctgttacacc ggtaacacct gggacccaac ttactgtcca    240
gacgacgaaa cttgcgctca aaactgtgcc ttggacggtg ctgactacga aggtacttac    300
gatgttacct cctctggttc ttccttgaag ttgaacttcg tcactggttc taacgtcggt    360
tccagattgt atttgttgca agatgactcc acctaccaaa tcttcaagtt gttgaacaga    420
gaatttcctt tcgacgtcga tgtgtccaac ttgccttgtg gtttgaacgg tgctctatac    480
ttcgttgcta tggacgctga tggtggtgtt ccaagtacc caaacaacaa ggctggtgcc    540
aaatacggta ctggttactg tgactctcaa tgtccacgtg acttgaagtt tattgatggt    600
gaagctaatg tcgaaggttg gcaaccatct ctaacaacg ctaacactgg catcggtgac    660
cacggttctt gctgtgccga aatggacgtt tgggaagcca actccatttc caacgccgtc    720
actccacacc catgtgacac tccaggtcaa actatatgtt ccggcgatga ctgtggtggt    780
acttactcta acgatagata cgctggtacc tgtgatccag acggttgcga cttcaatcca    840
tacagaatgg gtaacacttc cttttacggt ccaggcaaga tcatcgacac tactaagcca    900
ttcactgttg tcacccaatt cttgaccgac gatggtactg ataccggtac tttgtccgaa    960
atcaagagat tctacatcca aaactctaac gtcatcccac aaccaaattc cgacatctct    1020
ggtgtcactg gtaactccat taccaccgaa ttttgtaccg cccaaaagca agctttcggt    1080
gacaccgacg acttctctca acacggtggt ttggctaaga tgggtactgc tatgcaacaa    1140
ggtatggttt tggtcatgtc tttgtgggac gactacgctg ctcaaatgtt gtggttggac    1200
tccgattacc caaccgatgc cgacccaacc accctggta tcgctagagg tacctgtcca    1260
actgactctg tgttccatc tgacgtcgaa tcccaatctc caaactccta cgtcacttac    1320
tccaacatta aattcggtcc aatcaactcc actttcactg cttctaaccc tccaggtggt    1380
aacagaggta ctaccactac tcgtaggcca gctactgcaa ctggttcttc cccaggccca    1440
acccaatccc actacggtca atgtggtggt atcggttact ctggtccaac cgtctgtgct    1500
tctggtacta cctgtcaagt tttaaaccca tactactctc aatgtttg              1548
```

<210> SEQ ID NO 9
<211> LENGTH: 1549
<212> TYPE: DNA
<213> ORGANISM: Artificial Sequence
<220> FEATURE:
<223> OTHER INFORMATION: non-naturally occurring mutated CBH sequence

<400> SEQUENCE: 9

```
atgctaagaa gagctttact attgagctct tctgctatct tggccgttaa ggctcaacaa     60
gccggtaccg ctactgctga aaaccaccct ccattgacct ggcaagaatg taccgctcca    120
ggttcttgta ccacccaaaa cggtgctgtc gtcttggacg ctaactggag atgggtccac    180
gacgtcaacg gttacactaa ctgttacacc ggtaacacct gggacccaac ttactgtcca    240
gacgacgaaa cttgcgctca aaactgtgcc ttggacggtg ctgactacga aggtacttac    300
ggtgttacct cctctggttc ttccttgaag ttgaacttcg tcactggttc taacgtcggt    360
tccagattgt atttgttgca agatgactcc acttaccaaa tcttcaagtt gttgaacaga    420
gaatttcctt tcgacgtcga tgtgtccaac ttgccttgtg gtttgaacgg tgctctatac    480
ttcgttgcta tggacgctga tggtggtgtt ccaagtacc caaacaacaa ggctggtgcc    540
aaatacggta ctggttactg tgactctcaa tgtccacgtg acttgaagtt tattgatggt    600
```

```
gaagctaatg tcgaaggttg gcaaccatca tctaacaacg ctaacactgg catcggtgac      660
cacggttctt gctgtgccga aatggacgtt tgggaagcca actccatttc caacgccgtc      720
actccacacc catgtgacac tccaggtcaa actatgtgtt ccggcgatga ctgtggtggt      780
acttactcta acgatagata cgctggtacc tgtgatccag acggttgcga cttcaatcca      840
tacagaatgg gtaacacttc cttttacggt ccaggcaaga tcatcgacac tactaagcca      900
ttcactgttg tcacccaatt cttgaccgac gatggtactg ataccggtac tttgtccgaa      960
atcaagagat tctacatcca aaactctaac gtcatcccac aaccaaattc cgacatctct     1020
ggtgtcactg gtaactccat taccaccgaa attttgtacc gcccaaaagc aagctttcgg     1080
tgacaccgac gacttctctc aacacggtgg tttggctaag atgggtgctg ctatgcaaca     1140
aggtatggtt ttggtcatgt ctttgtgaga cgactacgct gctcaaatgt tgtggttgga     1200
ctctgattac ccaaccgatg ccgacccaac caccccctggt atcgctagag gtacctgtcc     1260
aactgactct ggtgttccat ctgacgtcga atcccaatct ccaaactcct acgtcactta     1320
ctccaacatt aaattcggtc caatcaactc cactttcact gctcctaacc atccaggtgg     1380
taacagaggt actacctcta ctcgtaggcc agctactaca actggttctt ccccaggccc     1440
aacccaaacc cactacggtc aatgtggtgg tatcggttac tctggtccaa ccgtcggtgc     1500
ttctggtact acctgtcaag ttttaaaccc atactactct caatgtttg                 1549
```

```
<210> SEQ ID NO 10
<211> LENGTH: 1548
<212> TYPE: DNA
<213> ORGANISM: Artificial Sequence
<220> FEATURE:
<223> OTHER INFORMATION: non-naturally occurring mutated CBH sequence
<220> FEATURE:
<221> NAME/KEY: misc_feature
<222> LOCATION: (1112)..(1112)
<223> OTHER INFORMATION: n is a, c, g, or t

<400> SEQUENCE: 10
```

```
atgctaagaa gagctttact attgagctct tctgctatct tggccgttaa ggctcaacaa      60
gccggtaccg ctactgctga aaaccaccct ccattgacct ggcaagaatg taccgctcca     120
ggttcttgta ccacccaaaa cggtgttgtc gtcttggacg ctaactggag atgggtccac     180
gacgtcaaca gttacactaa ctgttacacc ggtaacacct gggacccaac ttactgtcca     240
gacgacgaaa cttgcgctca aaactgtgcc ttggacggtg ctgactacga aggtacttac     300
ggtgttacct cctctggttc ttccttgaag ttgaacttcg tcactggttc tgacgtcggt     360
tccagattgt atttgttgca agatgactcc acttaccaaa tcttcaagtt gttgaacaga     420
gaatttctct tcgacgtcga tgtgtccaac ttgccttgtg gtttgaacgg tgctctatac     480
ttcgttgcta tggacgctga tggtggtgtt ccaagtacc caaacaacaa ggctggtgcc     540
aaatacggta ctggttacag tgactctcaa tgtccacgtg acttgaagtt taatgatggt     600
gaagctaatg tcgaaggttg gcaaccatat tctaacaacg ctaacactgg catcggtgac     660
cacggttctt actgtgccga aatggacgtt tgggaagcca actccatttc caacgccgtc     720
actccacacc catgtgacac tccaggtcaa actatgtgtt ccggcgatga ctgtggtggt     780
acttactcta acgatagata cgctggtacc tgtgatccag acggttgcga cttcaatcca     840
tacagaatgg gtaacacttc cttttacggt ccaggcaaga tcatcgacac tactaagcca     900
ttcactgttg tcacccaatt cttgaccgac gatggtactg ataccggtac tttgtccgaa     960
```

```
atcaagagat tctacatcca aaactctaac gtcatcccac aaccaaattc cgacatctct    1020
ggtgtcactg gtaactccat taccaccgaa ttttgtaccg cccaaaagca agctttcggt    1080
gacaccgaca acttctctca acacggtggt tnggctaaga tgggtgctgc tatgcaacaa    1140
ggtatggttt tggtcatgtc tttgtgggac gactacgctg ctcaaatgtt gtggttggac    1200
tccgattacc caaccgatgc cgacccaacc accctggta tcgctagagg tacctgtcca     1260
actgactctg gtgttccatc tgacgtcgaa tcccaatctc caaactccta cgtcacttac    1320
tccaacatta aattcggtcc aatcaactcc actttcactg cttctaaccc tccaggtggt    1380
aacagaggta ctaccactac tcgtaggcca gctacaacaa ctggttcttc cccaggccca    1440
acccaatccc actacggtca atgtggtggt atcggttact ctggtccaac cgtctgtgct    1500
tctggtacta cctgtcaagt tttaaaccca tactactctc aatgtttg                1548

<210> SEQ ID NO 11
<211> LENGTH: 1551
<212> TYPE: DNA
<213> ORGANISM: Artificial Sequence
<220> FEATURE:
<223> OTHER INFORMATION: non-naturally occurring mutated CBH sequence

<400> SEQUENCE: 11
atgctaagaa gagctttact attgagctct tctgctatct tggccgttaa ggctcaacaa    60
gccggtaccg ctactgctga aaaccaccct ccattgacct ggcaagaatg taccgctcca    120
ggttcttgta ccacccaaaa cggtgctgtc gtcttggacg ctaactggag atgggtccac    180
gacgtcaacg gttacactaa ctgttacacc ggtaacacct gggacccaac ttactgtcca    240
gacgacgaaa cttgcgctca aaactgtgcc ttggacggtg ctgactacga aggtacttac    300
ggtgttacct cctctggttc ttccttgaag ttgaacttcg tcactggttc taacgtcggt    360
tccagattgt atttgttgca agatgactcc acttaccaaa tcttcaagtt gttgaacaga    420
gaattttctt tcgacgtcga tgtgtccaac ttgccttgtg gtttgaacgg tgctctatac    480
ttcgttgcta tggacgctga tggtggtgtt tccaagtacc caaacaacaa ggctggtgcc    540
aaatacggta ctggttactg tgactctcaa tgtccacgtg acttgaagtt tattgatggt    600
gaagctaatg tcgaaggttg gcaaccatct tctaacaacg ctaacactgg catcggtgac    660
cacggttctt gctgtgccga atggacgtt tgggaagcca actccatttc caacgccgtc    720
actccacacc catgtgacac tccaggtcaa actatgtgtt ccggcgatga ctgtggtggt    780
acttactcta acgatagata cgctggtacc tgtgatccag acggttgcga cttcaatcca    840
tacagaatgg gtaacacttc ctttacggt ccaggcaaga tcatcgacac tactaagcca    900
ttcactgttg tcacccaatt cttgaccgac gatggtactg ataccggtac tttgtccgaa    960
atcaagagat tctacatcca aaactctaac gtcatcccac aaccaaattc cgacatctct    1020
ggtgtcactg gtaactccat taccaccgga ttttgtaccg cccaaaagca agctttcggt    1080
gacaccgacg acttctctca acacggtggt ttggctaaga tggatgctgc tatgcaacaa    1140
ggtatggttt tggtcatgtc tttgtgggat gactacgctg ctcaaatgtt gtggttggac    1200
tccgattacc caaccgatgc cgacccaacc accctggta tcgctagagg tacctgtcca    1260
actgactctg gtgttccatc tgacgtcgaa tcccaatctc caaactccta cgtcacttac    1320
tccaacatta aattcggtcc aatcaactcc actttcactg cttctaaccc tccaggtggt    1380
aacagaggta ctaccactac tcgtaggcca gctactacaa ctggttcttc cccaggccca    1440
atccaatccc actacggtca atgtggtggt atcggttact ctggtccaac cgtctgtgct    1500
```

```
tctggtacta cctgtcaagt tttaaaccca tactactctc aatgtttgta g        1551
```

<210> SEQ ID NO 12
<211> LENGTH: 1548
<212> TYPE: DNA
<213> ORGANISM: Artificial Sequence
<220> FEATURE:
<223> OTHER INFORMATION: non-naturally occurring CBH sequence

<400> SEQUENCE: 12

```
atgctaagaa gagctttact attgagctct tctgctatct tggccgttaa ggctcaacaa    60
gccggtaccg ctactgctga aaaccaccct ccattgacct ggcaagaatg taccgctcca   120
ggttcttgta ccacccaaaa cggtgctgtc gtcttggacg ctaactggag atgggtccac   180
gacgtcaacg gttacactaa ctgttacacc ggtaacacct gggacccaac ttactgtcca   240
gacgacgaaa cttgcgctca aaactgtgcc ttggacggtg ctgactacga aggtacttac   300
ggtgttacct cctctggttc ttccttgaag ttgaacttcg tcactggttc taacgtcggt   360
tccagattgt atttgttgca agatgactcc acttaccaaa tcttcaagtt gttgaacaga   420
gaattttctt cgacgtcga tgtgtccaac ttgccttgtg gtttgaacgg tgctctatac   480
ttcgttgcta tggacgctga tggtggtgtt ccaagtacc aaacaacaa ggctggtgcc   540
aaatacggta ctggttactg tgactctcaa tgtccacgtg acttgaagtt tattgatggt   600
gaagctaatg tcgaaggttg gcaaccatct tctaacaacg ctaacactgg catcggtgac   660
cacggttctt gctgtgccga atggacgtt tgggaagcca actccatttc caacgccgtc   720
actccacacc catgtgacac tccaggtcaa actatgtgtt ccggcgatga ctgtggtggt   780
acttactcta cgatagata cgctggtacc tgtgatccag acggttgcga cttcaatcca   840
tacagaatgg gtaacacttc cttttacggt ccaggcaaga tcatcgacac tactaagcca   900
ttcactgttg tcacccaatt cttgaccgac gatggtactg ataccggtac tttgtccgaa   960
atcaagagat tctacatcca aaactctaac gtcatcccac aaccaaattc cgacatctct  1020
ggtgtcactg gtaactccat taccaccgaa ttttgtaccg cccaaaagca agctttcggt  1080
gacaccgacg acttctctca acacggtggt ttggctaaga tgggtgctgc tatgcaacaa  1140
ggtatggttt tggtcatgtc tttgtgggac gactacgctg ctcaaatgtt gtggttggac  1200
tccgattacc caaccgatgc cgacccaacc accctggta tcgctagagg tacctgtcca  1260
actgactctg tgttccatc tgacgtcgaa tcccaatctc caaactccta cgtcacttac  1320
tccaacatta aattcggtcc aatcaactcc actttcactg cttctaaccc tccaggtggt  1380
aacagaggta ctaccactac tcgtaggcca gctactacaa ctggttcttc cccaggccca  1440
acccaatccc actacggtca atgtggtggt atcggttact ctggtccaac cgtctgtgct  1500
tctggtacta cctgtcaagt tttaaaccca tactactctc aatgtttg            1548
```

<210> SEQ ID NO 13
<211> LENGTH: 1548
<212> TYPE: DNA
<213> ORGANISM: Artificial Sequence
<220> FEATURE:
<223> OTHER INFORMATION: non-naturally occurring mutated CBH sequence

<400> SEQUENCE: 13

```
atgctaagaa gagctttact attgagctct tctgctatct tggccgttaa ggctcaacaa    60
gccggtaccg ctactgctga aaaccaccct ccattgacct ggcaagaatg taccgctcca   120
```

```
ggttcttgta ccacccaaaa cggtgctgtc gtcttggacg ctaactggag atgggtccac    180
gacgtcaacg gttacactaa ctgttacacc ggtaacacct gggacccaac ttactgtcca    240
gacgacgaaa cttgcgctca aaactgtgcc ttggacggtg ctgactacga aggtacttac    300
ggtgttacct cctctggttc ttccttgaag ttgaacttcg tcactggttc taacgtcggt    360
tccagattgt atttgttgca agatgactcc acttaccaaa tcttcaagtt gttgaacaga    420
gaattttctt tcgacgtcga tgtgtccaac ttgccttgtg gtttgaacgg tgctctatac    480
ttcgttgcta tggacgctga tggtggtgtt ccaagtacc caaacaacaa ggctggtgcc    540
aaatacggta ctggttactg tgactctcaa tgtccacgtg acttgaagtt tattgatggt    600
gaagctaatg tcgaaggttg gcaaccatct tctaacaacg ctaacactgg catcggtgac    660
cacggttctt gctgtgccga atggacgtt tgggaagcca actccatttc caacgccgtc    720
actccacacc catgtgacac tccaggtcaa actatgtgtt ccggcgatga ctgtggtggt    780
acttactcta acgatagata cgctggtacc tgtgatccag acggttgcga cttcaatcca    840
tacagaatgg gtaacacttc cttttacggt ccaggcaaga tcatcgacac tactaagcca    900
ttcactgttg tcacccaatt cttgaccgac gatggtactg ataccggtac tttgtccgaa    960
atcaagagat tctacatcca aaactctaac gtcatcccac aaccaaattc cgacatctct   1020
ggtgtcactg gtaactccat taccaccgaa ttttgtaccg cccaaaagca agctttcggt   1080
gacaccgacg acttctctca acacggtggt ttggctaaga tgggtgctgc tatgcaacaa   1140
ggtatggttt tggtcatgtc tttgtgggac gactacgctg ctcaaatgtt gtggttggac   1200
tccgattacc caaccgatgc cgacccaacc accctggta tcgctagagg tacctgtcca   1260
actgactctg gtgttccatc tgacgtcgaa tcccaatctc caaactccta cgtcacttac   1320
tccaacatta aattcggtcc aatcaactcc actttcactg cttctaaccc tccaggtgg   1380
aacagaggta ctaccactac tcgtaggcca gctactacaa ctggttcttc cccaggccca   1440
acccaatccc actacggtca atgtggtggt atcggttact ctggtccaac cgtctgtgct   1500
tctggtacta cctgtcaagt tttaaaccca tactactctc aatgtttg              1548

<210> SEQ ID NO 14
<211> LENGTH: 1548
<212> TYPE: DNA
<213> ORGANISM: Artificial Sequence
<220> FEATURE:
<223> OTHER INFORMATION: non-naturally occurring mutated CBH sequence

<400> SEQUENCE: 14
atgctaagaa gagctttact attgagctct tctgctatct tggccgttaa ggctcaacaa     60
gccggtaccg ctactgctga aaaccaccct ccattgacct ggcaagaatg taccgctcca    120
ggttcttgta ccacccaaaa cagtgctgtc gtcttggacg ctaactggag atgggtccac    180
gacgtcaacg gttacactaa ctgttacacc ggtaacacct gggacccaac ttactgtcca    240
gacgacgaaa cttgcgctca aaactgtgcc ttggacggtg ctgactacga aggtacttac    300
ggtgttacct cctctggttc ttccttgaag ttgaacttcg tcactggttc taacgtcggt    360
tccagattgt atttgttgca agatgactcc acttaccaaa tcttcaagtt gttgaacaga    420
gaattttctt tcgacgtcga tgtgtccaac ttgccttgtg gtttgaacgg tgctctatac    480
ttcgttgcta tggacgctga tggtggtgtt ccaagtacc caaacaacaa ggctggtgcc    540
aaatacggta ctggttactg tgactctcaa tgtccacgtg acttgaagtt tattgatggt    600
gaagctaatg tcgaaggttg gcaaccatct tctaacaacg ctaacactgg catcggtgac    660
```

```
cacggttctt gctgtgccga aatggacgtt tgggaagcca actccatttc caacgccgtc      720
actccacacc catgtgacac tccaggtcaa actatgtgtt ccggcgatga ctgtggtggt      780
acttactcta acgatagata cgctggtacc tgtgatccag acggttgcga cttcaatcca      840
tacagaatgg gtaacacttc cttttacggt ccaggcaaga tcatcgacac tactaagcca      900
ttcactgttg tcacccaatt cttgaccgac gatggtaatg ataccggtac tttgtccgaa      960
atcaagagat tctacatcca aaactctaac gtcatccac aaccaaattc cgacatctct     1020
ggtgtcactg gtaactccat taccaccgaa ttttgtaccg cccaaaagca agctttcggt     1080
gacaccgacg acttctctca acacggtggt ttggctaaga tgggtgctgc tatgcaacaa     1140
ggtatggttt tggtcatgtc tttgtgggac gactacgctg ctcaaatgtt gtggttggac     1200
tccgattacc caaccgatgc cgacccaacc accctggta tcgctagagg tacctgtcca      1260
actgactctg tgttccatc tgacgtcgaa tcccaatctc caaactccta cgtcacttac      1320
tccaacatta aattcggtcc aatcaactcc actttcactg cttctaaccc tccaggtggt     1380
aacagaggta ctaccactac tcgtaggcca gctactacaa ctggttcttc cccaggccca     1440
acccaatccc actacggtca atgtggtggt atcggttact ctggtccaac cgtctgtgct     1500
tctggtacta cctgtcaagt tttaaaccca tactactctc aatgtttg                 1548

<210> SEQ ID NO 15
<211> LENGTH: 1548
<212> TYPE: DNA
<213> ORGANISM: Artificial Sequence
<220> FEATURE:
<223> OTHER INFORMATION: non-naturally occurring mutated CBH sequence

<400> SEQUENCE: 15
atgctaagaa gagctttact attgagctct tctgctatct tggccgttaa ggctcaacaa       60
gccggtaccg ctactgctga aaaccaccct ccattgacct ggcaagaatg taccgctcca      120
ggttcttgta ccacccaaaa cggtgctgtc gtcttggacg ctaactggag atgggtccac      180
gacgtcaacg ttacactaa ctgttacacc ggtaacacct gggacccaac ttactgtcca      240
gacgacgaaa cttgcgctca aaactgtgcc ttgacggtg ctgactacga aggtacttac      300
ggtgttacct cctctggttc ttccttgaag ttgaacttcg tcactggttc taacgtcggt      360
tccagattgt atttgttgca agatgactcc acttaccaaa tcttcaagtt gttgaacaga      420
gaattttctt tcgacgtcga tgtgtccaac ttgccttgtg gtttgaacgg tgctctatac      480
ttcgttgcta tggacgctga tggtggtgtt ccaagtacc caaacaacaa ggctggtgcc      540
aaatacggta ctggttactg tgactctcaa tgtccacgtg acttgaagtt tattgatggt      600
gaagctaatg tcgaaggttg gcaaccatct tctaacaacg ctaacactgg catcggtgac      660
cacggttctt gctgtgccga aatggacgtt tgggaagcca actccatttc caacgccgtc      720
actccacacc catgtgacac tccaggtcaa actatgtgtt ccggcgatga ctgtggtggt      780
acttactcta acgatagata cgctggtacc tgtgatccag acggttgcga cttcaatcca      840
tacagaatgg gtaacacttc cttttacggt ccaggcaaga tcatcgacac tactaagcca      900
ttcactgttg tcacccaatt cttgaccgac gatggtactg ataccggtac tttgtccgaa      960
atcaagagat tctacatcca aaactctaac gtcatccac aaccaaattc cgacatctct     1020
ggtgtcactg gtaactccat taccaccgaa ttttgtaccg cccaaaagca agctttcggt     1080
gacaccgacg acttctctca acacggtggt ttggctaaga tgggtgctgc tatgcaacaa     1140
```

-continued

```
ggtatggttt tggtcatgtc tttgtgggac gactacgctg ctcaaatgtt gtggttggac    1200
tccgattacc caaccgatgc cgacccaacc accccctggta tcgctagagg tacctgtcca    1260
actgactctg gtgttccatc tgacgtcgaa tcccaatctc caaactccta cgtcacttac    1320
tccaacatta aattcggtcc aatcaactcc actttcactg cttctaaccc tccaggtggt    1380
aacagaggta ctaccactac tcgtaggcca gctactacaa ctggttcttc cctaggccca    1440
acccaatccc actacggtca atgtggtggt atcggttact ctggtccaac cgtctgtgct    1500
tctggtacta cctgtcaagt tttaaaccca tactactctc aatgtttg                 1548
```

<210> SEQ ID NO 16
<211> LENGTH: 1548
<212> TYPE: DNA
<213> ORGANISM: Artificial Sequence
<220> FEATURE:
<223> OTHER INFORMATION: non-naturally occurring mutated CBH sequence

<400> SEQUENCE: 16

```
atgctaagaa gagctttact attgagctct tctgctatct tggccgttaa ggctcaacaa     60
gccggtaccg ctactgctga aaaccaccct ccattgacct ggcaagaatg taccgctcca    120
ggttcttgta ccaccccaaaa cggtgctgtc gtccttgacg ctaactggag atgggtccac    180
gacgtcaacg gttacactaa ctgttacacc ggtaacacct gggacccaac ttactgtcca    240
gacgacgaaa cttgcgctca aaactgtgcc ttggacggtg ctgactacga aggtacttac    300
ggtgttacct cctctggttc ttcccttgaag ttgaacttcg tcactggttc taacgtcggt    360
tccagattgt atttgttgca agatgactcc acttaccaaa tcttcaagtt gttgaacaga    420
gaattttctt tcgacgtcga tgtgtccaac ttgccttgtg gtttgaacgg tgctctatac    480
ttcgttgcta tggacgctga tggtggtgtt tccaagtacc caaacaacaa ggctggtgcc    540
aaatacggta ctggttactg tgactctcaa tgtccacgtg acttgaagtt tattgatggt    600
gaagctaatg tcgaaggttg gcaaccatct tctaacaacg ctaacactgg catcggtgac    660
cacggttctt gctgtgccga aatggacgtt tgggaagcca actccatttc caacgccgtc    720
actccacacc catgtgacac tccaggtcaa actatgtgtt ccggcgatga ctgtggtggt    780
acttactcta acgatagata cgctggtacc tgtgatccag acggttgcga cttcaatcca    840
tacagaatgg gtaacacttc cttttacggt ccaggcaaga tcatcgacac tactaagcca    900
ttcactgttg tcacccaatt cttgaccgac gatggtactg ataccggtac tttgtccgaa    960
atcaagagat tctacatcca aaactctaac gtcatccacc aaccaaattc cgacatctct    1020
ggtgtcactg gtaactccat taccaccgaa ttttgtaccg cccaaaagca agctttcggt    1080
gacaccgacg acttctctca cacggtggg ttggctaaga tgggtgctgc tatgcaacaa    1140
ggtatggttt tggtcatgtc tttgtgggac gactacgctg ctcaaatgtt gtggttggac    1200
tccgattacc caaccgatgc cgacccaacc accccctggta tcgctagagg tacctgtcca    1260
actgactctg gtgttccatc tgacgtcgaa tcccaatctc caaactccta cgtcacttac    1320
tccaacatta aattcggtcc aatcaactcc actttcactg cttctaaccc tccaggtggt    1380
aacagaggta ctaccactac tcgtaggcca gctactacaa ctggttctcc cccaggccca    1440
acccaatccc actacggtca atgtggtggt atcggttact ctggtccaac cgtctgtgct    1500
tctggtacta cctgtcaagt tttaaaccca tactactctc aatgtttg                 1548
```

<210> SEQ ID NO 17
<211> LENGTH: 1548

```
<212> TYPE: DNA
<213> ORGANISM: Artificial Sequence
<220> FEATURE:
<223> OTHER INFORMATION: non-naturally occurring mutated CBH sequence

<400> SEQUENCE: 17
atgctaagaa gagctttact attgagctct tctgctatct tggccgttaa ggctcaacaa      60
gccggtaccg ctactgctga aaaccaccct ccattgacct ggcaagaatg taccgctcca     120
ggttcttgta ccacccaaaa cggtgctgtc gtcttggacg ctaactggag atgggtccac     180
gacgtcaacg gttacactaa ctgttacacc ggtaacacct gggacccaac ttactgtcca     240
gacgacgaaa cttgcgctca aaactgtgcc ttggacggtg ctgactacga aggtacttac     300
ggtgttacct cctctggttc ttccttgaag ttgaacttcg tcactggttc taacgtcggt     360
tccagattgt atttgttgca agatgactcc acttaccaaa tcttcaagtt gttgaacaga     420
gaattttctt tcgacgtcga tgtgtccaac ttgccttgtg gtttgaacgg tgctctatac     480
ttcgttgcta tggacgctga tggtggtgtt tccaagtacc caaacaacaa ggctggtgcc     540
aaatacggta ctggttactg tgactctcaa tgtccacgtg acttgaagtt tattgatggt     600
gaagctaatg tcgaaggttg gcaaccatct tctaacaacg ctaacactgg catcggtgac     660
cacggttctt gctgtgccga atggacgtt tgggaagcca actccatttc caacgccgtc     720
actccacacc catgtgacac tccaggtcaa actatgtgtt ccggcgatga ctgtggtggt     780
acttactcta cgatagata cgctggtacc tgtgatccag acggttgcga cttcaatcca     840
tacagaatgg gtaacacttc cttttacggt ccaggcaaga tcatcgacac tactaagcca     900
ttcactgttg tcacccaatt cttgaccgac gatggtactg ataccggtac tttgtccgaa     960
atcaagagat ctacatcca aaactctaac gtcatcccac aaccaaattc cgacatctct    1020
ggtgtcactg gtaactccat taccaccgaa ttttgtaccg cccaaaagca agctttcggt    1080
gacaccgacg acttctctca cacggtggt ttggctaaga tgggtgctgc tatgcaacaa    1140
ggtatggttt tggtcatgtc tttgtgggac gactacgctg ctcaaatgtt gtggttggac    1200
tccgattacc caaccgatgc cgacccaacc acccctggta tcgctagagg tacctgtcca    1260
actgactctg tgttccatc tgacgtcgaa tcccaatctc caaactccta cgtcacttac    1320
tccaacatta aattcggtcc aatcaactcc actttcactg cttctaaccc tccaggtggt    1380
aacagaggta ctaccactac tcgtaggcca gctactacaa ctggttcttc cccaggccca    1440
acccaatccc actacggtca atgtggtggt atcggttact ctggtccaac cgtctgtgct    1500
tctggtacta cctgtcaagt tttaaaccca tactactctc aatgtttg              1548

<210> SEQ ID NO 18
<211> LENGTH: 1548
<212> TYPE: DNA
<213> ORGANISM: Artificial Sequence
<220> FEATURE:
<223> OTHER INFORMATION: non-naturally occurring mutated CBH sequence

<400> SEQUENCE: 18
atgctaagaa gagctttact attgagctct tctgctatct tggccgttaa ggctcaacaa      60
gccggtaccg ctactgctga aaaccaccct ccattgacct ggcaagaatg taccgctcca     120
ggttcttgta ccacccaaaa cggtgctgtc gtcttggacg ctaactggag atgggtccac     180
gacgtcaacg gttacactaa ctgttacacc ggtaacacct gggacccaac ttactgtcca     240
gacgacgaaa cttgcgctca aaactgtgcc ttggacggtg ctgactacga aggtacttac     300
```

```
ggtgttacct cctctggttc ttccttgaag ttgaacttcg tcactggttc taacgtcggt    360
tccagattgt atttgttgca agatgactcc acttaccaaa tcttcaagtt gttgaacaga    420
gaattttctt tcgacgtcga tgtgtccaac ttgccttgtg gtttgaacgg tgctctatac    480
ttcgttgcta tggacgctga tggtggtgtt ccaagtacc caaacaacaa ggctggtgcc     540
aaatacggta ctggttactg tgactctcaa tgtccacgtg acttgaagtt tattgatggt    600
gaagctaatg tcgaaggttg gcaaccatct tctaacaacg ctaacactgg catcggtgac    660
cacggttctt gctgtgccga aatggacgtt tgggaagcca actccatttc caacgccgtc    720
actccacacc catgtgacac tcaaggtcaa actatgtgtt ccggcgatga ctgtggtggt    780
acttactcta acgatagata cgctggtacc tgtgatccag acggttgcga cttcaatcca    840
tacagaatgg gtaacacttc cttttacggt ccaggcaaga tcatcgacac tactaagcca    900
ttcactgttg tcacccaatt cttgaccgac gatggtactg ataccggtac tttgtccgaa    960
atcaagagat tctacatcca aaactctaac gtcatcccac aaccaaattc cgacatctct   1020
ggtgtcactg gtaactccat taccaccgaa ttttgtaccg cccaaaagca agctttcggt   1080
gacaccgacg acttctctca acacggtggt ttggctaaga tgggtgctgc tatgcaacaa   1140
ggtatggttt tggtcatgtc tttgtgggac gactacgctg ctcaaatgtt gtggttggac   1200
tccgattacc caaccgatgc cgacccaacc acccctggta tcgctagagg tacctgtcca   1260
actgactctg tgttccatc tgacgtcgaa tcccaatctc caaactccta cgtcacttac   1320
tccaacatta aattcggtcc aatcaactcc actttcactg cttctaaccc tccaggtggt   1380
aacagaggta ctaccactac tcgtaggcca gctactacaa ctggttcttc cccaggccca   1440
acccaatccc actacggtca atgtggtggt atcggttact ctggtccaac cgtctgtgct   1500
tctggtacta cctgtcaagt tttaaaccca tactactctc aatgtttg                1548

<210> SEQ ID NO 19
<211> LENGTH: 1548
<212> TYPE: DNA
<213> ORGANISM: Artificial Sequence
<220> FEATURE:
<223> OTHER INFORMATION: non-naturally occurring mutated CBH sequence

<400> SEQUENCE: 19
atgctaagaa gagctttact attgagctct tctgctatct tggccgttaa ggctcaacaa     60
gccggtaccg ctactgctga aaaccaccct ccattgacct ggcaagaatg tatcgctcca    120
ggttcttgta ccacccaaaa cggtgctgtc gtcttggacg ctaactggag atgggtccac    180
gacgtcaacg gttacactaa ctgttacacc ggtaacacct gggacccaac ttactgtcca    240
gacgacgaaa cttgcgctca aaactgtgcc ttggacggtg ctgactacga aggtacttac    300
ggtgttacct cctctggttc ttccttgaag ttgaacttcg tcactggttc taacgtcggt    360
tccagattgt atttgttgca agatgactcc acttaccaaa tcttcaagtt gttgaacaga    420
gaattttctt tcgacgtcga tgtgtccaac ttgccttgtg gtttgaacgg tgctctatac    480
ttcgttgcta tggacgctga tggtggtgtt accaagtacc caaacaacaa ggctggtgcc    540
aaatacggta ctggttactg tgactctcaa tgtccacgtg acttgaagtt tattgatggt    600
gaagctaatg tcgaaggttg gcaaccatct tctaacaacg ctaacactgg catcggtgac    660
cacggttctt gctgtcccga aatggacgtt tgggaagcca actccatttc caacgccgtc    720
actccacacc catgtgacac tcaaggtcaa actatgtgtt ccggcgatga ctgtggtggt    780
acttactcta acgatagata cgctggtacc tgtgatccag acggttgcga cttcaatcca    840
```

```
tacagaatgg gtaacacttc cttttacggt ccaggcaaga tcatcgacac tactaagcca    900
ttcactgttg tcacccaatt cttgaccgac gatgatactg ataccggtac tttgtccgaa    960
atcaagagat tctacatcca aaactctaac gtcatcccac aaccaaattc cgacatctct   1020
ggtgtcactg gtaactccat taccaccgaa ttttgtaccg cccaaaagca agctttcgat   1080
gacaccgacg acttctctca acacggtggt ttggctaaga tgggtgctgc tatgcaacaa   1140
ggtatggttt tggtcatgtc tttgtgggac gactacgctg ctcaaatgtt gtggttggac   1200
tccgattacc caaccgatgc cgacccaacc acccctggta tcgctagagg tacctgtcca   1260
actgactctg tgttccatc tgacgtcgaa tcccaatctc caaactccta cgtcacttac   1320
tccaacatta aattcggtcc aatcaactcc actttcactg cttctaaccc tccaggtggt   1380
aacagaggta ctaccactac tcgtaggcca gctactacaa ctggttcttc cccaggccca   1440
acccaatccc actacggtca atgtggtggt atcggttact ctggtccaac cgtctgtgct   1500
tctggtacta cctgtcaagt tttaaaccca tactactctc aatgtttg               1548

<210> SEQ ID NO 20
<211> LENGTH: 516
<212> TYPE: PRT
<213> ORGANISM: Artificial Sequence
<220> FEATURE:
<223> OTHER INFORMATION: non-naturally occurring mutated CBH sequence

<400> SEQUENCE: 20

Met Leu Arg Arg Ala Leu Leu Ser Ser Ala Ile Leu Ala Val
1               5                   10                  15

Lys Ala Gln Gln Ala Gly Thr Ala Thr Thr Glu Asn His Pro Pro Leu
                20                  25                  30

Thr Trp Gln Glu Cys Thr Ala Pro Gly Ser Cys Thr Thr Gln Asn Gly
            35                  40                  45

Ala Val Val Leu Asp Ala Asn Trp Arg Trp Val His Asp Val Asn Gly
        50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240
```

```
Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
        435                 440                 445

Asn Ser Thr Phe Thr Ala Ser Asn Pro Pro Gly Gly Asn Arg Gly Thr
    450                 455                 460

Thr Thr Thr Arg Arg Pro Ala Thr Thr Thr Gly Ser Ser Pro Gly Pro
465                 470                 475                 480

Thr Gln Ser His Tyr Gly Gln Cys Gly Gly Ile Gly Tyr Ser Gly Pro
                485                 490                 495

Thr Val Cys Ala Ser Gly Thr Thr Cys Gln Val Leu Asn Pro Tyr Tyr
            500                 505                 510

Ser Gln Cys Leu
        515

<210> SEQ ID NO 21
<211> LENGTH: 514
<212> TYPE: PRT
<213> ORGANISM: Artificial Sequence
<220> FEATURE:
<223> OTHER INFORMATION: non-naturally occurring mutated CBH sequence

<400> SEQUENCE: 21

Met Leu Arg Arg Ala Leu Leu Leu Ser Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
    50                  55                  60

Tyr Thr Asn Cys Tyr Thr Gly Asn Thr Trp Asp Pro Thr Tyr Cys Pro
65                  70                  75                  80
```

```
Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Thr Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Val Gln Leu Thr Leu Val Phe His Leu Thr Ser Asn Pro Asn
            420                 425                 430

Leu Gln Thr Pro Thr Ser Leu Thr Pro Thr Leu Asn Ser Val Gln Ser
        435                 440                 445

Thr Pro Leu Ser Leu Leu Leu Thr Leu Gln Val Val Thr Glu Val Leu
    450                 455                 460

Pro Leu Leu Val Gly Gln Leu Leu Gln Leu Val Leu Pro Gln Ala Gln
465                 470                 475                 480

Pro Asn Pro Thr Thr Val Asn Val Val Val Ser Val Thr Leu Val Gln
                485                 490                 495
```

```
Pro Ser Val Leu Leu Val Leu His Val Lys Phe Thr His Thr Thr Leu
        500                 505                 510
Asn Val

<210> SEQ ID NO 22
<211> LENGTH: 516
<212> TYPE: PRT
<213> ORGANISM: Artificial Sequence
<220> FEATURE:
<223> OTHER INFORMATION: non-naturally occurring mutated CBH sequence

<400> SEQUENCE: 22

Met Leu Arg Arg Ala Leu Leu Leu Ser Ser Ala Ile Leu Ala Val
1               5                   10                  15

Lys Ala Gln Gln Ala Gly Thr Ala Thr Ala Glu Asn His Pro Pro Leu
                20                  25                  30

Thr Trp Gln Glu Cys Thr Ala Pro Gly Ser Cys Thr Thr Gln Asn Gly
            35                  40                  45

Ala Val Val Leu Asp Ala Asn Trp Arg Trp Val His Asp Val Asn Gly
        50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Ile Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Val Ala Asn Val Glu Gly Trp Gln
        195                 200                 205

Pro Ser Ser Asn Asn Ala Asn Thr Gly Ile Gly Asp His Gly Ser Cys
        210                 215                 220

Tyr Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
```

```
                    340                 345                 350
Thr Ala Gln Lys Gln Ala Phe Gly Asp Thr Glu Asp Phe Ser Gln His
                355                 360                 365
Gly Gly Leu Ala Lys Met Gly Ala Ala Met Gln Gln Gly Met Val Leu
            370                 375                 380
Val Met Ser Leu Trp Asp Asp Tyr Ala Ala Arg Met Leu Trp Leu Asp
385                 390                 395                 400
Ser Asp Tyr Pro Thr Asp Ala Asp Pro Thr Thr Pro Gly Ile Ala Arg
                405                 410                 415
Gly Thr Cys Pro Thr Asp Ser Gly Val Pro Ser Asp Val Glu Ser Gln
            420                 425                 430
Ser Pro Asp Ser Tyr Val Thr Tyr Ser Asn Ile Lys Phe Gly Pro Ile
                435                 440                 445
Asn Ser Thr Phe Thr Ala Ser Asn Pro Gly Gly Asn Arg Gly Ile
            450                 455                 460
Thr Thr Thr Arg Arg Pro Ala Thr Thr Thr Gly Ser Ser Pro Gly Pro
465                 470                 475                 480
Thr Gln Ser His Tyr Gly Gln Cys Gly Gly Ile Gly Tyr Ser Gly Pro
                485                 490                 495
Thr Val Tyr Ala Ser Gly Thr Thr Tyr Gln Val Leu Asn Pro Tyr Tyr
            500                 505                 510
Ser Gln Cys Leu
        515

<210> SEQ ID NO 23
<211> LENGTH: 516
<212> TYPE: PRT
<213> ORGANISM: Artificial Sequence
<220> FEATURE:
<223> OTHER INFORMATION: non-naturally occurring mutated CBH sequence

<400> SEQUENCE: 23

Met Leu Arg Arg Ala Leu Leu Leu Ser Ser Ser Ala Ile Leu Ala Val
1               5                   10                  15
Lys Ala Gln Gln Ala Gly Thr Ala Thr Ala Glu Asn His Pro Pro Leu
            20                  25                  30
Thr Trp Gln Glu Ser Thr Ala Pro Gly Ser Cys Thr Thr Gln Asn Gly
        35                  40                  45
Ala Val Val Leu Asp Ala Asn Trp Arg Trp Val His Asp Val Asn Gly
    50                  55                  60
Tyr Thr Asn Cys Tyr Thr Gly Asn Thr Trp Asp Pro Thr Tyr Cys Pro
65                  70                  75                  80
Asp Asp Glu Thr Cys Ala Gln Asn Cys Ala Leu Asp Gly Ala Asp Tyr
                85                  90                  95
Glu Gly Thr Tyr Gly Val Thr Ser Ser Gly Ser Ser Leu Lys Leu Asn
            100                 105                 110
Phe Val Thr Gly Ser Asn Val Gly Ser Arg Leu Tyr Leu Leu Gln Val
        115                 120                 125
Asp Ser Thr Tyr Gln Ile Phe Lys Leu Leu Asn Arg Glu Phe Ser Phe
    130                 135                 140
Asp Val Asp Met Ser Asn Leu Pro Cys Gly Leu Asn Gly Ala Leu Tyr
145                 150                 155                 160
Phe Val Ala Met Asp Ala Asp Gly Gly Val Ser Lys Tyr Pro Asn Asn
                165                 170                 175
Lys Ala Gly Ala Lys Tyr Gly Thr Gly Tyr Cys Asp Ser Gln Cys Pro
```

```
            180                 185                 190
Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Tyr Phe
        275                 280                 285

Tyr Gly Pro Gly Lys Ile Ile Asp Thr Thr Lys Pro Phe Thr Val Val
    290                 295                 300

Thr Gln Phe Leu Thr Asp Tyr Gly Thr Asp Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
        435                 440                 445

Asn Ser Thr Phe Thr Ala Ser Asn Pro Pro Gly Gly Asn Arg Gly Thr
    450                 455                 460

Thr Thr Thr Arg Arg Pro Ala Thr Thr Thr Gly Ser Ser Pro Gly Pro
465                 470                 475                 480

Thr Gln Ser His Tyr Gly Gln Cys Gly Gly Ile Gly Tyr Ser Gly Pro
                485                 490                 495

Thr Val Cys Ala Ser Gly Thr Thr Cys Gln Val Leu Asn Pro Tyr Tyr
            500                 505                 510

Ser Gln Cys Leu
        515

<210> SEQ ID NO 24
<211> LENGTH: 515
<212> TYPE: PRT
<213> ORGANISM: Artificial Sequence
<220> FEATURE:
<223> OTHER INFORMATION: non-naturally occurring mutated CBH sequence

<400> SEQUENCE: 24

Met Leu Arg Arg Ala Leu Leu Leu Ser Ser Ala Ile Leu Ala Val
1               5                   10                  15

Lys Ala Gln Gln Ala Gly Thr Ala Thr Ala Glu Asn His Pro Pro Leu
```

```
            20                  25                  30
Thr Trp Gln Glu Cys Thr Ala Pro Gly Ser Cys Thr Thr Gln Asn Gly
         35                  40                  45

Ala Val Val Leu Asp Ala Asn Trp Arg Trp Val His Asp Val Asn Gly
 50                  55                  60

Tyr Thr Asn Cys Tyr Thr Gly Asn Thr Trp Asp Pro Thr Tyr Cys Pro
 65                  70                  75                  80

Asp Asp Glu Thr Cys Ala Gln Asn Cys Ala Leu Asp Gly Ala Glu Tyr
                 85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
            115                 120                 125

Asp Ser Thr Tyr Gln Ile Phe Lys Leu Leu Asn Arg Glu Phe Ser Phe
            130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
            195                 200                 205

Pro Ser Ser Asn Asn Ala Asn Thr Gly Ile Gly Asp His Gly Ser Cys
            210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Ser Thr Cys Asp
            260                 265                 270

Pro Asp Gly Cys Asp Ile Asn Pro Tyr Arg Met Gly Asn Thr Ser Phe
            275                 280                 285

Tyr Gly Pro Gly Lys Ile Ile Asp Thr Thr Lys Pro Phe Thr Val Val
            290                 295                 300

Thr Gln Phe Leu Thr Asp Asp Gly Ile Asp Thr Gly Thr Leu Ser Asp
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Phe Ser Gln His
            355                 360                 365

Gly Gly Leu Ala Lys Met Gly Ala Ala Met Gln Gln Gly Met Val Leu
            370                 375                 380

Val Lys Ser Leu Trp Asp Asp Tyr Ala Ala Gln Met Leu Trp Leu Asp
385                 390                 395                 400

Ser His Tyr Pro Thr Asp Ala Ala Pro Ile Thr Pro Gly Ile Thr Arg
                405                 410                 415

Asp Thr Cys Pro Thr Asp Tyr Gly Val Pro Ser Asp Val Glu Ser Gln
            420                 425                 430

Ser Pro Asn Ser Tyr Val Thr Tyr Ser Asn Ile Lys Phe Gly Pro Ile
            435                 440                 445
```

```
Asn Ser Thr Ile Thr Ala Ser Ile Pro Pro Val Gly Asn Gly Thr Thr
    450                 455                 460

Thr Thr Arg Arg Pro Ala Thr Thr Gly Ser Ser Pro Gly Pro Thr
465                 470                 475                 480

Gln Ser His Tyr Cys Gln Cys Gly Gly Ile Gly Tyr Ser Gly Pro Thr
                485                 490                 495

Val Cys Ala Ser Gly Thr Thr Cys Gln Val Leu Asn Pro Tyr Tyr Ser
                500                 505                 510

Gln Cys Leu
        515

<210> SEQ ID NO 25
<211> LENGTH: 516
<212> TYPE: PRT
<213> ORGANISM: Artificial Sequence
<220> FEATURE:
<223> OTHER INFORMATION: non-naturally occurring mutated CBH sequence

<400> SEQUENCE: 25

Met Leu Arg Ile Ala Leu Leu Ser Ser Ala Ile Leu Ala Val
1               5                   10                  15

Lys Ala Gln Gln Ala Gly Thr Ala Thr Ala Glu Asn His Pro Pro Leu
                20                  25                  30

Thr Trp Gln Glu Cys Thr Asp Pro Gly Ser Cys Thr Thr Gln Asn Gly
            35                  40                  45

Ala Val Val Leu Asp Ala Asn Trp Arg Trp Val His Asp Val Asn Gly
        50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Asp Val Thr Ser Ser Gly Ser Ser Leu Lys Leu Asn
                100                 105                 110

Phe Val Thr Gly Ser Asn Val Gly Ser Arg Leu Tyr Leu Leu Gln Asp
            115                 120                 125

Asp Ser Thr Tyr Gln Ile Phe Lys Leu Leu Asn Arg Glu Phe Ser Phe
        130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
                180                 185                 190

Arg Asp Leu Lys Phe Ile Asp Gly Glu Ala Asn Val Glu Gly Trp Gln
            195                 200                 205

Pro Ser Ser Asn Asn Ala Asn Thr Gly Ile Gly Asp His Gly Ser Cys
        210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Ile Cys Ser Gly Asp
                245                 250                 255

Asp Cys Gly Gly Thr Tyr Ser Asn Asp Arg Tyr Ala Gly Thr Cys Asp
                260                 265                 270

Pro Asp Gly Cys Asp Phe Asn Pro Tyr Arg Met Gly Asn Thr Ser Phe
            275                 280                 285
```

```
Tyr Gly Pro Gly Lys Ile Ile Asp Thr Thr Lys Pro Phe Thr Val Val
            290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Phe Ser Gln His
            355                 360                 365

Gly Gly Leu Ala Lys Met Gly Thr Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
            435                 440                 445

Asn Ser Thr Phe Thr Ala Ser Asn Pro Pro Gly Gly Asn Arg Gly Thr
            450                 455                 460

Thr Thr Thr Arg Arg Pro Ala Thr Ala Thr Gly Ser Ser Pro Gly Pro
465                 470                 475                 480

Thr Gln Ser His Tyr Gly Gln Cys Gly Gly Ile Gly Tyr Ser Gly Pro
                485                 490                 495

Thr Val Cys Ala Ser Gly Thr Thr Cys Gln Val Leu Asn Pro Tyr Tyr
            500                 505                 510

Ser Gln Cys Leu
            515

<210> SEQ ID NO 26
<211> LENGTH: 506
<212> TYPE: PRT
<213> ORGANISM: Artificial Sequence
<220> FEATURE:
<223> OTHER INFORMATION: non-naturally occurring mutated CBH sequence

<400> SEQUENCE: 26

Met Leu Arg Arg Ala Leu Leu Leu Ser Ser Ser Ala Ile Leu Ala Val
1               5                   10                  15

Lys Ala Gln Gln Ala Gly Thr Ala Thr Ala Glu Asn His Pro Pro Leu
                20                  25                  30

Thr Trp Gln Glu Cys Thr Ala Pro Gly Ser Cys Thr Thr Gln Asn Gly
            35                  40                  45

Ala Val Val Leu Asp Ala Asn Trp Arg Trp Val His Asp Val Asn Gly
        50                  55                  60

Tyr Thr Asn Cys Tyr Thr Gly Asn Thr Trp Asp Pro Thr Tyr Cys Pro
65              70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
            115                 120                 125
```

Asp Ser Thr Tyr Gln Ile Phe Lys Leu Leu Asn Arg Glu Phe Ser Phe
            130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Ile Leu
            340                 345                 350

Tyr Arg Pro Lys Ala Ser Phe Arg His Arg Leu Leu Ser Thr Arg
        355                 360                 365

Trp Phe Gly Asp Gly Cys Cys Tyr Ala Thr Arg Tyr Gly Phe Gly His
370                 375                 380

Val Phe Val Arg Leu Arg Cys Ser Asn Val Val Val Gly Leu Leu
385                 390                 395                 400

Pro Asn Arg Cys Arg Pro Asn His Pro Trp Tyr Arg Arg Tyr Leu Ser
                405                 410                 415

Asn Leu Trp Cys Ser Ile Arg Arg Ile Pro Ile Ser Lys Leu Leu Arg
            420                 425                 430

His Leu Leu Gln His Ile Arg Ser Asn Gln Leu His Phe His Cys Ser
        435                 440                 445

Pro Ser Arg Trp Gln Arg Tyr Tyr Leu Tyr Ser Ala Ser Tyr Tyr Asn
450                 455                 460

Trp Phe Phe Pro Arg Pro Asn Pro Asn Pro Leu Arg Ser Met Trp Trp
465                 470                 475                 480

Tyr Arg Leu Leu Trp Ser Asn Arg Arg Cys Phe Trp Tyr Tyr Leu Ser
                485                 490                 495

Ser Phe Lys Pro Ile Leu Leu Ser Met Phe
            500                 505

<210> SEQ ID NO 27
<211> LENGTH: 516
<212> TYPE: PRT
<213> ORGANISM: Artificial Sequence
<220> FEATURE:

<223> OTHER INFORMATION: non-naturally occurring mutated CBH sequence
<220> FEATURE:
<221> NAME/KEY: misc_feature
<222> LOCATION: (371)..(371)
<223> OTHER INFORMATION: Xaa can be any naturally occurring amino acid

<400> SEQUENCE: 27

```
Met Leu Arg Arg Ala Leu Leu Leu Ser Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Val Val Val Leu Asp Ala Asn Trp Arg Trp Val His Asp Val Asn Ser
    50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Gly Ser Ser Leu Lys Leu Asn
            100                 105                 110

Phe Val Thr Gly Ser Asp Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Ser Asp Ser Gln Cys Pro
            180                 185                 190

Arg Asp Leu Lys Phe Asn Asp Gly Glu Ala Asn Val Glu Gly Trp Gln
        195                 200                 205

Pro Tyr Ser Asn Asn Ala Asn Thr Gly Ile Gly Asp His Gly Ser Tyr
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Asn Phe Ser Gln His
        355                 360                 365

Gly Gly Xaa Ala Lys Met Gly Ala Ala Met Gln Gln Gly Met Val Leu
    370                 375                 380
```

```
Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
            435                 440                 445

Asn Ser Thr Phe Thr Ala Ser Asn Pro Pro Gly Gly Asn Arg Gly Thr
            450                 455                 460

Thr Thr Thr Arg Arg Pro Ala Thr Thr Thr Gly Ser Ser Pro Gly Pro
465                 470                 475                 480

Thr Gln Ser His Tyr Gly Gln Cys Gly Gly Ile Gly Tyr Ser Gly Pro
                485                 490                 495

Thr Val Cys Ala Ser Gly Thr Thr Cys Gln Val Leu Asn Pro Tyr Tyr
                500                 505                 510

Ser Gln Cys Leu
            515

<210> SEQ ID NO 28
<211> LENGTH: 516
<212> TYPE: PRT
<213> ORGANISM: Artificial Sequence
<220> FEATURE:
<223> OTHER INFORMATION: non-naturally occurring mutated CBH sequence

<400> SEQUENCE: 28

Met Leu Arg Arg Ala Leu Leu Leu Ser Ser Ser Ala Ile Leu Ala Val
1               5                   10                  15

Lys Ala Gln Gln Ala Gly Thr Ala Thr Ala Glu Asn His Pro Pro Leu
                20                  25                  30

Thr Trp Gln Glu Cys Thr Ala Pro Gly Ser Cys Thr Thr Gln Asn Gly
            35                  40                  45

Ala Val Val Leu Asp Ala Asn Trp Arg Trp Val His Asp Val Asn Gly
50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
            115                 120                 125

Asp Ser Thr Tyr Gln Ile Phe Lys Leu Leu Asn Arg Glu Phe Ser Phe
            130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
                180                 185                 190

Arg Asp Leu Lys Phe Ile Asp Gly Glu Ala Asn Val Glu Gly Trp Gln
            195                 200                 205

Pro Ser Ser Asn Asn Ala Asn Thr Gly Ile Gly Asp His Gly Ser Cys
            210                 215                 220
```

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
            245                 250                 255

Asp Cys Gly Gly Thr Tyr Ser Asn Asp Arg Tyr Ala Gly Thr Cys Asp
        260                 265                 270

Pro Asp Gly Cys Asp Phe Asn Pro Tyr Arg Met Gly Asn Thr Ser Phe
    275                 280                 285

Tyr Gly Pro Gly Lys Ile Ile Asp Thr Thr Lys Pro Phe Thr Val Val
290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Gly Phe Cys
            340                 345                 350

Thr Ala Gln Lys Gln Ala Phe Gly Asp Thr Asp Asp Phe Ser Gln His
        355                 360                 365

Gly Gly Leu Ala Lys Met Asp Ala Ala Met Gln Gly Met Val Leu
370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
        435                 440                 445

Asn Ser Thr Phe Thr Ala Ser Asn Pro Pro Gly Gly Asn Arg Gly Thr
450                 455                 460

Thr Thr Thr Arg Arg Pro Ala Thr Thr Thr Gly Ser Ser Pro Gly Pro
465                 470                 475                 480

Ile Gln Ser His Tyr Gly Gln Cys Gly Gly Ile Gly Tyr Ser Gly Pro
                485                 490                 495

Thr Val Cys Ala Ser Gly Thr Thr Cys Gln Val Leu Asn Pro Tyr Tyr
            500                 505                 510

Ser Gln Cys Leu
    515

<210> SEQ ID NO 29
<211> LENGTH: 516
<212> TYPE: PRT
<213> ORGANISM: Artificial Sequence
<220> FEATURE:
<223> OTHER INFORMATION: non-naturally occurring mutated CBH sequence

<400> SEQUENCE: 29

Met Leu Arg Arg Ala Leu Leu Ser Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
    50                  55                  60

-continued

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
            85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
            115                 120                 125

Asp Ser Thr Tyr Gln Ile Phe Lys Leu Leu Asn Arg Glu Phe Ser Phe
130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
            165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
            195                 200                 205

Pro Ser Ser Asn Ala Asn Thr Gly Ile Gly Asp His Gly Ser Cys
            210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
            245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
            275                 280                 285

Tyr Gly Pro Gly Lys Ile Ile Asp Thr Thr Lys Pro Phe Thr Val Val
            290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
            325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Phe Ser Gln His
            355                 360                 365

Gly Gly Leu Ala Lys Met Gly Ala Ala Met Gln Gln Gly Met Val Leu
            370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
            405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
            435                 440                 445

Asn Ser Thr Phe Thr Ala Ser Asn Pro Pro Gly Gly Asn Arg Gly Thr
            450                 455                 460

Thr Thr Thr Arg Arg Pro Ala Thr Thr Thr Gly Ser Ser Pro Gly Pro
465                 470                 475                 480

```
Thr Gln Ser His Tyr Gly Gln Cys Gly Gly Ile Gly Tyr Ser Gly Pro
            485                 490                 495

Thr Val Cys Ala Ser Gly Thr Thr Cys Gln Val Leu Asn Pro Tyr Tyr
        500                 505                 510

Ser Gln Cys Leu
        515

<210> SEQ ID NO 30
<211> LENGTH: 516
<212> TYPE: PRT
<213> ORGANISM: Artificial Sequence
<220> FEATURE:
<223> OTHER INFORMATION: non-naturally occurring mutated CBH sequence

<400> SEQUENCE: 30

Met Leu Arg Arg Ala Leu Leu Ser Ser Ala Ile Leu Ala Val
1               5                   10                  15

Lys Ala Gln Gln Ala Gly Thr Ala Thr Ala Glu Asn His Pro Pro Leu
                20                  25                  30

Thr Trp Gln Glu Cys Thr Ala Pro Gly Ser Cys Thr Thr Gln Asn Gly
            35                  40                  45

Ala Val Val Leu Asp Ala Asn Trp Arg Trp Val His Asp Val Asn Gly
        50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320
```

Ile Lys Arg Phe Tyr Ile Gln Asn Ser Asn Val Ile Pro Gln Pro Asn
            325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Phe Ser Gln His
            355                 360                 365

Gly Gly Leu Ala Lys Met Gly Ala Ala Met Gln Gln Gly Met Val Leu
            370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
            405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
            435                 440                 445

Asn Ser Thr Phe Thr Ala Ser Asn Pro Pro Gly Gly Asn Arg Gly Thr
            450                 455                 460

Thr Thr Thr Arg Arg Pro Ala Thr Thr Thr Gly Ser Ser Pro Gly Pro
465                 470                 475                 480

Thr Gln Ser His Tyr Gly Gln Cys Gly Gly Ile Gly Tyr Ser Gly Pro
            485                 490                 495

Thr Val Cys Ala Ser Gly Thr Thr Cys Gln Val Leu Asn Pro Tyr Tyr
            500                 505                 510

Ser Gln Cys Leu
        515

<210> SEQ ID NO 31
<211> LENGTH: 516
<212> TYPE: PRT
<213> ORGANISM: Artificial Sequence
<220> FEATURE:
<223> OTHER INFORMATION: non-naturally occurring mutated CBH sequence

<400> SEQUENCE: 31

Met Leu Arg Arg Ala Leu Leu Leu Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Ser
            35                  40                  45

Ala Val Val Leu Asp Ala Asn Trp Arg Trp Val His Asp Val Asn Gly
        50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
            85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
            115                 120                 125

Asp Ser Thr Tyr Gln Ile Phe Lys Leu Leu Asn Arg Glu Phe Ser Phe
            130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
            165                 170                 175

Lys Ala Gly Ala Lys Tyr Gly Thr Gly Tyr Cys Asp Ser Gln Cys Pro
        180                 185                 190

Arg Asp Leu Lys Phe Ile Asp Gly Glu Ala Asn Val Glu Gly Trp Gln
    195                 200                 205

Pro Ser Ser Asn Asn Ala Asn Thr Gly Ile Gly Asp His Gly Ser Cys
210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Asn Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
        435                 440                 445

Asn Ser Thr Phe Thr Ala Ser Asn Pro Pro Gly Gly Asn Arg Gly Thr
    450                 455                 460

Thr Thr Thr Arg Arg Pro Ala Thr Thr Thr Gly Ser Ser Pro Gly Pro
465                 470                 475                 480

Thr Gln Ser His Tyr Gly Gln Cys Gly Gly Ile Gly Tyr Ser Gly Pro
                485                 490                 495

Thr Val Cys Ala Ser Gly Thr Thr Cys Gln Val Leu Asn Pro Tyr Tyr
            500                 505                 510

Ser Gln Cys Leu
        515

<210> SEQ ID NO 32
<211> LENGTH: 516
<212> TYPE: PRT
<213> ORGANISM: Artificial Sequence
<220> FEATURE:
<223> OTHER INFORMATION: non-naturally occurring mutated CBH sequence

<400> SEQUENCE: 32

```
Met Leu Arg Arg Ala Leu Leu Leu Ser Ser Ala Ile Leu Ala Val
1               5                   10                  15

Lys Ala Gln Gln Ala Gly Thr Ala Thr Ala Glu Asn His Pro Pro Leu
        20                  25                  30

Thr Trp Gln Glu Cys Thr Ala Pro Gly Ser Cys Thr Thr Gln Asn Gly
            35                  40                  45

Ala Val Val Leu Asp Ala Asn Trp Arg Trp Val His Asp Val Asn Gly
50                  55                  60

Tyr Thr Asn Cys Tyr Thr Gly Asn Thr Trp Asp Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
            115                 120                 125

Asp Ser Thr Tyr Gln Ile Phe Lys Leu Leu Asn Arg Glu Phe Ser Phe
        130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
            165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
        210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
        290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
            325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Phe Ser Gln His
        355                 360                 365

Gly Gly Leu Ala Lys Met Gly Ala Ala Met Gln Gln Gly Met Val Leu
        370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
            405                 410                 415

Gly Thr Cys Pro Thr Asp Ser Gly Val Pro Ser Asp Val Glu Ser Gln
```

```
                 420                 425                 430
Ser Pro Asn Ser Tyr Val Thr Tyr Ser Asn Ile Lys Phe Gly Pro Ile
                435                 440                 445

Asn Ser Thr Phe Thr Ala Ser Asn Pro Pro Gly Gly Asn Arg Gly Thr
            450                 455                 460

Thr Thr Thr Arg Arg Pro Ala Thr Thr Thr Gly Ser Ser Leu Gly Pro
465                 470                 475                 480

Thr Gln Ser His Tyr Gly Gln Cys Gly Gly Ile Gly Tyr Ser Gly Pro
                485                 490                 495

Thr Val Cys Ala Ser Gly Thr Thr Cys Gln Val Leu Asn Pro Tyr Tyr
            500                 505                 510

Ser Gln Cys Leu
            515

<210> SEQ ID NO 33
<211> LENGTH: 516
<212> TYPE: PRT
<213> ORGANISM: Artificial Sequence
<220> FEATURE:
<223> OTHER INFORMATION: non-naturally occurring mutated CBH sequence

<400> SEQUENCE: 33

Met Leu Arg Arg Ala Leu Leu Leu Ser Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
    50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
```

```
                    260                 265                 270
        Pro Asp Gly Cys Asp Phe Asn Pro Tyr Arg Met Gly Asn Thr Ser Phe
                    275                 280                 285
        Tyr Gly Pro Gly Lys Ile Ile Asp Thr Thr Lys Pro Phe Thr Val Val
                    290                 295                 300
        Thr Gln Phe Leu Thr Asp Asp Gly Thr Asp Thr Gly Thr Leu Ser Glu
        305                 310                 315                 320
        Ile Lys Arg Phe Tyr Ile Gln Asn Ser Asn Val Ile Pro Gln Pro Asn
                        325                 330                 335
        Ser Asp Ile Ser Gly Val Thr Gly Asn Ser Ile Thr Thr Glu Phe Cys
                    340                 345                 350
        Thr Ala Gln Lys Gln Ala Phe Gly Asp Thr Asp Phe Ser Gln His
                355                 360                 365
        Gly Gly Leu Ala Lys Met Gly Ala Ala Met Gln Gln Gly Met Val Leu
                370                 375                 380
        Val Met Ser Leu Trp Asp Asp Tyr Ala Ala Gln Met Leu Trp Leu Asp
        385                 390                 395                 400
        Ser Asp Tyr Pro Thr Asp Ala Asp Pro Thr Thr Pro Gly Ile Ala Arg
                        405                 410                 415
        Gly Thr Cys Pro Thr Asp Ser Gly Val Pro Ser Asp Val Glu Ser Gln
                        420                 425                 430
        Ser Pro Asn Ser Tyr Val Thr Tyr Ser Asn Ile Lys Phe Gly Pro Ile
                    435                 440                 445
        Asn Ser Thr Phe Thr Ala Ser Asn Pro Pro Gly Gly Asn Arg Gly Thr
                    450                 455                 460
        Thr Thr Thr Arg Arg Pro Ala Thr Thr Thr Gly Ser Pro Pro Gly Pro
        465                 470                 475                 480
        Thr Gln Ser His Tyr Gly Gln Cys Gly Gly Ile Gly Tyr Ser Gly Pro
                        485                 490                 495
        Thr Val Cys Ala Ser Gly Thr Thr Cys Gln Val Leu Asn Pro Tyr Tyr
                    500                 505                 510
        Ser Gln Cys Leu
                    515

<210> SEQ ID NO 34
<211> LENGTH: 516
<212> TYPE: PRT
<213> ORGANISM: Artificial Sequence
<220> FEATURE:
<223> OTHER INFORMATION: non-naturally occurring mutated CBH sequence

<400> SEQUENCE: 34

Met Leu Arg Arg Ala Leu Leu Leu Ser Ser Ser Ala Ile Leu Ala Val
        1               5                   10                  15
        Lys Ala Gln Gln Ala Gly Thr Ala Thr Ala Glu Asn His Pro Pro Leu
                        20                  25                  30
        Thr Trp Gln Glu Cys Thr Ala Pro Gly Ser Cys Thr Thr Gln Asn Gly
                        35                  40                  45
        Ala Val Val Leu Asp Ala Asn Trp Arg Trp Val His Asp Val Asn Gly
                        50                  55                  60
        Tyr Thr Asn Cys Tyr Thr Gly Asn Thr Trp Asp Pro Thr Tyr Cys Pro
        65                  70                  75                  80
        Asp Asp Glu Thr Cys Ala Gln Asn Cys Ala Leu Asp Gly Ala Asp Tyr
                        85                  90                  95
        Glu Gly Thr Tyr Gly Val Thr Ser Ser Gly Ser Ser Leu Lys Leu Asn
```

```
            100             105             110
Phe Val Thr Gly Ser Asn Val Gly Ser Arg Leu Tyr Leu Leu Gln Asp
            115             120             125

Asp Ser Thr Tyr Gln Ile Phe Lys Leu Leu Asn Arg Glu Phe Ser Phe
            130             135             140

Asp Val Asp Val Ser Asn Leu Pro Cys Gly Leu Asn Gly Ala Leu Tyr
145             150             155             160

Phe Val Ala Met Asp Ala Asp Gly Gly Val Ser Lys Tyr Pro Asn Asn
            165             170             175

Lys Ala Gly Ala Lys Tyr Gly Thr Gly Tyr Cys Asp Ser Gln Cys Pro
            180             185             190

Arg Asp Leu Lys Phe Ile Asp Gly Glu Ala Asn Val Glu Gly Trp Gln
            195             200             205

Pro Ser Ser Asn Asn Ala Asn Thr Gly Ile Gly Asp His Gly Ser Cys
            210             215             220

Cys Ala Glu Met Asp Val Trp Glu Ala Asn Ser Ile Ser Asn Ala Val
225             230             235             240

Thr Pro His Pro Cys Asp Thr Pro Gly Gln Thr Met Cys Ser Gly Asp
            245             250             255

Asp Cys Gly Gly Thr Tyr Ser Asn Asp Arg Tyr Ala Gly Thr Cys Asp
            260             265             270

Pro Asp Gly Cys Asp Phe Asn Pro Tyr Arg Met Gly Asn Thr Ser Phe
            275             280             285

Tyr Gly Pro Gly Lys Ile Ile Asp Thr Thr Lys Pro Phe Thr Val Val
            290             295             300

Thr Gln Phe Leu Thr Asp Asp Gly Thr Asp Thr Gly Thr Leu Ser Glu
305             310             315             320

Ile Lys Arg Phe Tyr Ile Gln Asn Ser Asn Val Ile Pro Gln Pro Asn
            325             330             335

Ser Asp Ile Ser Gly Val Thr Gly Asn Ser Ile Thr Thr Glu Phe Cys
            340             345             350

Thr Ala Gln Lys Gln Ala Phe Gly Asp Thr Asp Asp Phe Ser Gln His
            355             360             365

Gly Gly Leu Ala Lys Met Gly Ala Ala Met Gln Gln Gly Met Val Leu
            370             375             380

Val Met Ser Leu Trp Asp Asp Tyr Ala Ala Gln Met Leu Trp Leu Asp
385             390             395             400

Ser Asp Tyr Pro Thr Asp Ala Asp Pro Thr Thr Pro Gly Ile Ala Arg
            405             410             415

Gly Thr Cys Pro Thr Asp Ser Gly Val Pro Ser Asp Val Glu Ser Gln
            420             425             430

Ser Pro Asn Ser Tyr Val Thr Tyr Ser Asn Ile Lys Phe Gly Pro Ile
            435             440             445

Asn Ser Thr Phe Thr Ala Ser Asn Pro Pro Gly Gly Asn Arg Gly Thr
            450             455             460

Thr Thr Thr Arg Arg Pro Ala Thr Thr Thr Gly Ser Ser Pro Gly Pro
465             470             475             480

Thr Gln Ser His Tyr Gly Gln Cys Gly Gly Ile Gly Tyr Ser Gly Pro
            485             490             495

Thr Val Cys Ala Ser Gly Thr Thr Cys Gln Val Leu Asn Pro Tyr Tyr
            500             505             510

Ser Gln Cys Leu
            515
```

<210> SEQ ID NO 35
<211> LENGTH: 516
<212> TYPE: PRT
<213> ORGANISM: Artificial Sequence
<220> FEATURE:
<223> OTHER INFORMATION: non-naturally occurring mutated CBH sequence

<400> SEQUENCE: 35

```
Met Leu Arg Arg Ala Leu Leu Leu Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
                35                  40                  45

Ala Val Val Leu Asp Ala Asn Trp Arg Trp Val His Asp Val Asn Gly
        50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
            115                 120                 125

Asp Ser Thr Tyr Gln Ile Phe Lys Leu Leu Asn Arg Glu Phe Ser Phe
        130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Gln Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Asp Phe Ser Gln His
        355                 360                 365
```

Gly Gly Leu Ala Lys Met Gly Ala Ala Met Gln Gln Gly Met Val Leu
            370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
            435                 440                 445

Asn Ser Thr Phe Thr Ala Ser Asn Pro Pro Gly Gly Asn Arg Gly Thr
        450                 455                 460

Thr Thr Thr Arg Arg Pro Ala Thr Thr Thr Gly Ser Ser Pro Gly Pro
465                 470                 475                 480

Thr Gln Ser His Tyr Gly Gln Cys Gly Gly Ile Gly Tyr Ser Gly Pro
                485                 490                 495

Thr Val Cys Ala Ser Gly Thr Thr Cys Gln Val Leu Asn Pro Tyr Tyr
            500                 505                 510

Ser Gln Cys Leu
            515

<210> SEQ ID NO 36
<211> LENGTH: 516
<212> TYPE: PRT
<213> ORGANISM: Artificial Sequence
<220> FEATURE:
<223> OTHER INFORMATION: non-naturally occurring mutated CBH sequence

<400> SEQUENCE: 36

Met Leu Arg Arg Ala Leu Leu Leu Ser Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Ile Ala Pro Gly Ser Cys Thr Thr Gln Asn Gly
        35                  40                  45

Ala Val Val Leu Asp Ala Asn Trp Arg Trp Val His Asp Val Asn Gly
    50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Thr Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
            210                 215                 220

Cys Pro Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
            245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
            275                 280                 285

Tyr Gly Pro Gly Lys Ile Ile Asp Thr Thr Lys Pro Phe Thr Val Val
            290                 295                 300

Thr Gln Phe Leu Thr Asp Asp Thr Asp Thr Gly Thr Leu Ser Glu
305                 310                 315                 320

Ile Lys Arg Phe Tyr Ile Gln Asn Ser Asn Val Ile Pro Gln Pro Asn
            325                 330                 335

Ser Asp Ile Ser Gly Val Thr Gly Asn Ser Ile Thr Glu Phe Cys
            340                 345                 350

Thr Ala Gln Lys Gln Ala Phe Asp Asp Thr Asp Phe Ser Gln His
            355                 360                 365

Gly Gly Leu Ala Lys Met Gly Ala Ala Met Gln Gln Gly Met Val Leu
            370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
            405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
            435                 440                 445

Asn Ser Thr Phe Thr Ala Ser Asn Pro Pro Gly Gly Asn Arg Gly Thr
            450                 455                 460

Thr Thr Thr Arg Arg Pro Ala Thr Thr Thr Gly Ser Ser Pro Gly Pro
465                 470                 475                 480

Thr Gln Ser His Tyr Gly Gln Cys Gly Gly Ile Gly Tyr Ser Gly Pro
            485                 490                 495

Thr Val Cys Ala Ser Gly Thr Thr Cys Gln Val Leu Asn Pro Tyr Tyr
            500                 505                 510

Ser Gln Cys Leu
            515

<210> SEQ ID NO 37
<211> LENGTH: 514
<212> TYPE: PRT
<213> ORGANISM: Trichoderma reesei

<400> SEQUENCE: 37

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
            35                  40                  45

Val Val Ile Asp Ala Asn Trp Arg Trp Thr His Ala Thr Asn Ser Ser

```
            50                  55                  60
Thr Asn Cys Tyr Asp Gly Asn Thr Trp Ser Ser Thr Leu Cys Pro Asp
 65                  70                  75                  80

Asn Glu Thr Cys Ala Lys Asn Cys Cys Leu Asp Gly Ala Ala Tyr Ala
                     85                  90                  95

Ser Thr Tyr Gly Val Thr Thr Ser Gly Asn Ser Leu Ser Ile Gly Phe
                100                 105                 110

Val Thr Gln Ser Ala Gln Lys Asn Val Gly Ala Arg Leu Tyr Leu Met
                115                 120                 125

Ala Ser Asp Thr Thr Tyr Gln Glu Phe Thr Leu Leu Gly Asn Glu Phe
                130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
                180                 185                 190

Cys Pro Arg Asp Leu Lys Phe Ile Asn Gly Gln Ala Asn Val Glu Gly
                195                 200                 205

Trp Glu Pro Ser Ser Asn Asn Ala Asn Thr Gly Ile Gly Gly His Gly
                210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
                260                 265                 270

Cys Asp Pro Asp Gly Cys Asp Trp Asn Pro Tyr Arg Leu Gly Asn Thr
                275                 280                 285

Ser Phe Tyr Gly Pro Gly Ser Ser Phe Thr Leu Asp Thr Thr Lys Lys
                290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
                340                 345                 350

Ala Glu Phe Gly Gly Ser Ser Phe Ser Asp Lys Gly Gly Leu Thr Gln
                355                 360                 365

Phe Lys Lys Ala Thr Ser Gly Gly Met Val Leu Val Met Ser Leu Trp
                370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
                420                 425                 430

Val Thr Phe Ser Asn Ile Lys Phe Gly Pro Ile Gly Ser Thr Gly Asn
                435                 440                 445

Pro Ser Gly Gly Asn Pro Pro Gly Gly Asn Pro Pro Gly Thr Thr Thr
                450                 455                 460

Thr Arg Arg Pro Ala Thr Thr Thr Gly Ser Ser Pro Gly Pro Thr Gln
465                 470                 475                 480
```

```
Ser His Tyr Gly Gln Cys Gly Gly Ile Gly Tyr Ser Gly Pro Thr Val
                485                 490                 495
Cys Ala Ser Gly Thr Thr Cys Gln Val Leu Asn Pro Tyr Tyr Ser Gln
            500                 505                 510
Cys Leu
```

FUNGAL CELLOBIOHYDROLASES

CROSS-REFERENCE TO RELATED APPLICATIONS

This application claims priority under 35 U.S.C. § 119 to U.S. Provisional Patent Application No. 62/518,754 filed on Jun. 13, 2017, the contents of which are hereby incorporated by reference in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

BACKGROUND

The rate-limiting step in the enzymatic hydrolysis of lignocellulose is generally considered to be the breakdown of crystalline cellulose by cellobiohydrolases (CBHs). Among the non-complexed fungal cellulose systems, glycosyl hydrolase family 7 cellobiohydrolases are the most well studied glycosyl hydrolase enzymes and have dominated the industrial applications of cellulases. However, owing to their extremely slow rate of catalysis, industrial application of these enzymes would benefit greatly from improvements in their hydrolytic capabilities.

SUMMARY

In an aspect, disclosed herein is a non-naturally occurring, mutated Cel7A polypeptide having increased cellulose or lignocellulosic degrading activity when compared to the naturally occurring Cel7A polypeptide from which the non-naturally occurring mutated Cel7A polypeptide was derived. In an embodiment, the non-naturally occurring mutated Cel7A polypeptide is disclosed wherein the non-naturally occurring mutated Cel7A polypeptide comprises a L371M mutation of SEQ ID NO: 2. In another embodiment, the non-naturally occurring mutated Cel7A polypeptide is disclosed wherein the non-naturally occurring mutated Cel7A polypeptide comprises a D92E mutation of SEQ ID NO: 2. In another embodiment, the non-naturally occurring mutated Cel7A polypeptide is disclosed wherein the non-naturally occurring mutated Cel7A polypeptide comprises a C43S, Y78Y, C79S, and a 99-stop mutation of SEQ ID NO: 2. In an embodiment, the non-naturally occurring mutated Cel7A polypeptide is disclosed wherein the non-naturally occurring mutated Cel7A polypeptide comprises a A239V mutation of SEQ ID NO: 2. In an embodiment, the non-naturally occurring mutated Cel7A polypeptide is disclosed wherein the non-naturally occurring mutated Cel7A polypeptide comprises a T481I mutation of SEQ ID NO: 2. In another embodiment, the non-naturally occurring mutated Cel7A polypeptide is disclosed and has up to 2.3 times the cellulose or lignocellulosic degrading activity when compared to the naturally occurring Cel7A polypeptide from which the non-naturally occurring mutated Cel7A polypeptide was derived. In an embodiment, the non-naturally occurring mutated Cel7A polypeptide is disclosed and has up to 2.3 times the cellulose or lignocellulosic degrading activity when compared to the naturally occurring Cel7A polypeptide from which the non-naturally occurring mutated Cel7A polypeptide was derived wherein the non-naturally occurring Cel7A polypeptide comprises a L371M mutation of SEQ ID NO: 2. In an embodiment, the non-naturally occurring mutated Cel7A polypeptide is disclosed and has up to 2.3 times the cellulose or lignocellulosic degrading activity when compared to the naturally occurring Cel7A polypeptide from which the non-naturally occurring mutated Cel7A polypeptide was derived wherein the non-naturally occurring Cel7A polypeptide comprises a D92E mutation of SEQ ID NO: 2. In an embodiment, the non-naturally occurring mutated Cel7A polypeptide is disclosed and has up to 2.3 times the cellulose or lignocellulosic degrading activity when compared to the naturally occurring Cel7A polypeptide from which the non-naturally occurring mutated Cel7A polypeptide was derived wherein the non-naturally occurring Cel7A polypeptide comprises a C43S, Y78Y, C79S, and a 99-stop mutation of SEQ ID NO: 2. In an embodiment, the non-naturally occurring mutated Cel7A polypeptide is disclosed and has up to 2.3 times the cellulose or lignocellulosic degrading activity when compared to the naturally occurring Cel7A polypeptide from which the non-naturally occurring mutated Cel7A polypeptide was derived wherein the non-naturally occurring Cel7A polypeptide comprises a A239V mutation of SEQ ID NO: 2. In another embodiment, the non-naturally occurring mutated Cel7A polypeptide is disclosed and has up to 2.3 times the cellulose or lignocellulosic degrading activity when compared to the naturally occurring Cel7A polypeptide from which the non-naturally occurring mutated Cel7A polypeptide was derived wherein the non-naturally occurring Cel7A polypeptide comprises a T481I mutation of SEQ ID NO: 2.

In an aspect, an isolated nucleic acid molecule encoding the non-naturally occurring mutated Cel7A polypeptide. In an embodiment, the isolated nucleic acid molecule, further comprises a promoter operably linked to the nucleic acid molecule. In another embodiment, the isolated nucleic acid molecule has a promoter that allows expression of the nucleic acid in a filamentous fungal host cell. In another embodiment, the isolated nucleic acid molecule contains a nucleic acid is within an expression vector. In an embodiment, a host cell comprising the expression vector is disclosed that also expresses a recombinant polypeptide encoded by the nucleic acid molecule. In an embodiment, the host cell is a fungal cell.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIGS. 2A and 2B depict the nucleotide (A) (SEQ ID NO: 1) and amino acid (B) (SEQ ID NO: 2) sequences of for the fusion CBH1 sequence prior to mutagenesis.

FIGS. 3A through 3Q depict the nucleotide sequences (SEQ ID NOs: 3-19, respectively) of mutant library clones of the nucleotide sequence for the fusion CBH1 sequence (SEQ ID NO: 1), with the mutation sites highlighted.

FIGS. 4A through 4Q depict the amino acid sequences (SEQ ID NOs: 20-36, respectively) of mutant library clones of the amino acid sequence for the fusion CBH1 sequence (SEQ ID NO: 2), with the mutated residues highlighted and the frame-shifted sequences underlined.

Figure 8:
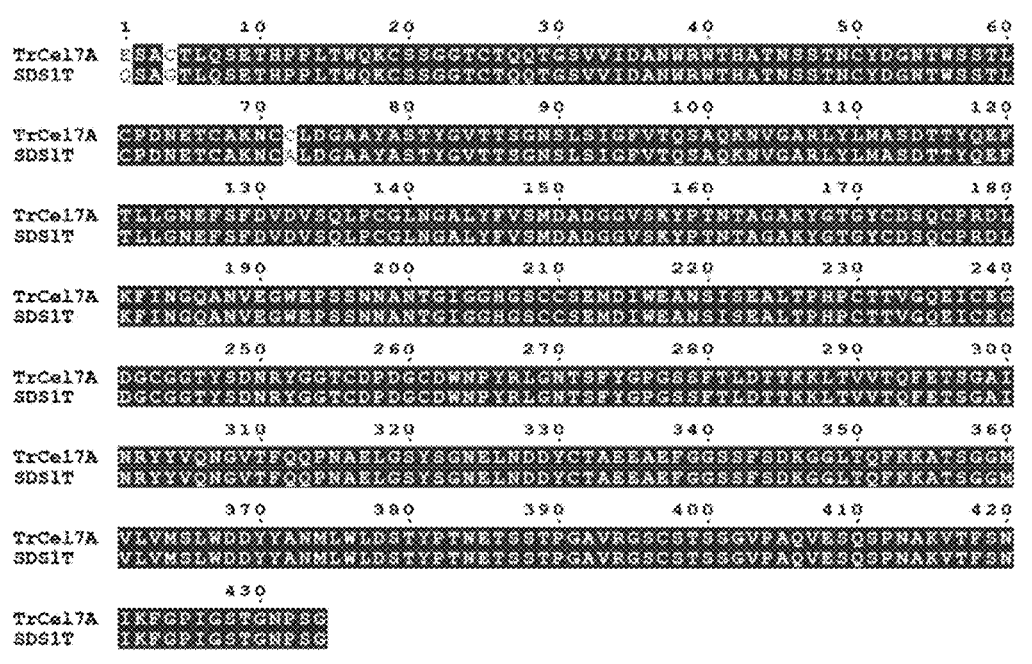

FIG. 8 depicts a portion of the amino acid sequence of the SDS1T mutant Cel7A compared to a portion of the full amino acid sequence of the wildtype *T. reesei* Cel7A parent (TrCel7A) SEQ ID NO: 37 as depicted in FIG. 19.

Figure 9:
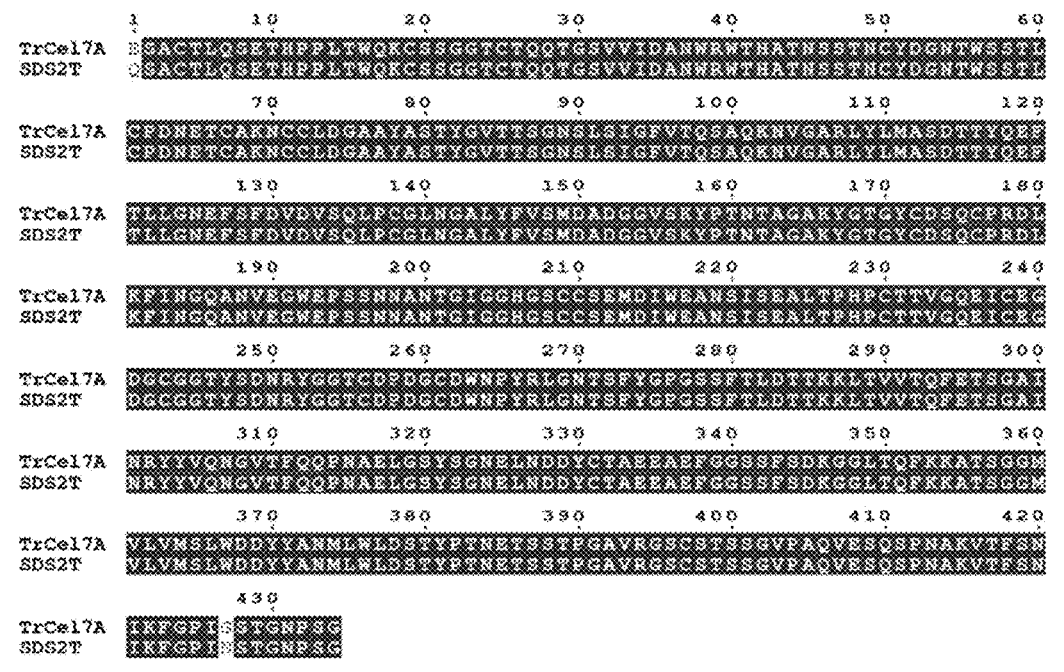

FIG. 9 depicts a portion of the amino acid sequence of the SDS2T mutant Cel7A compared to a portion of the full amino acid sequence of the wildtype *T. reesei* Cel7A parent (TrCel7A) SEQ ID NO: 37 as depicted in FIG. 19.

FIG. 10 depicts a portion of the amino acid sequence of the SDS3T mutant Cel7A compared to a portion of the full amino acid sequence of the wildtype *T. reesei* Cel7A parent (TrCel7A) SEQ ID NO: 37 as depicted in FIG. 19.

FIG. 11 depicts a portion of the amino acid sequence of the SDS4T mutant Cel7A compared to a portion of the full amino acid sequence of the wildtype *T. reesei* Cel7A parent (TrCel7A) SEQ ID NO: 37 as depicted in FIG. 19.

Figure 12:
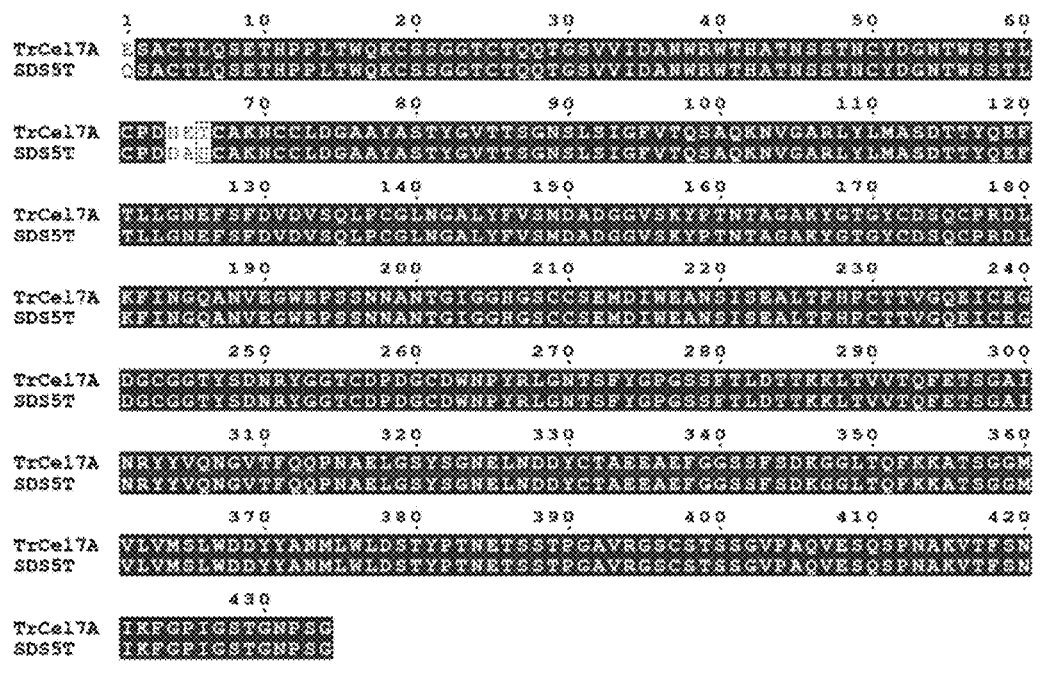

FIG. 12 depicts a portion of the amino acid sequence of the SDS5T mutant Cel7A compared to a portion of the full amino acid sequence of the wildtype *T. reesei* Cel7A parent (TrCel7A) SEQ ID NO: 37 as depicted in FIG. 19.

Figure 13:
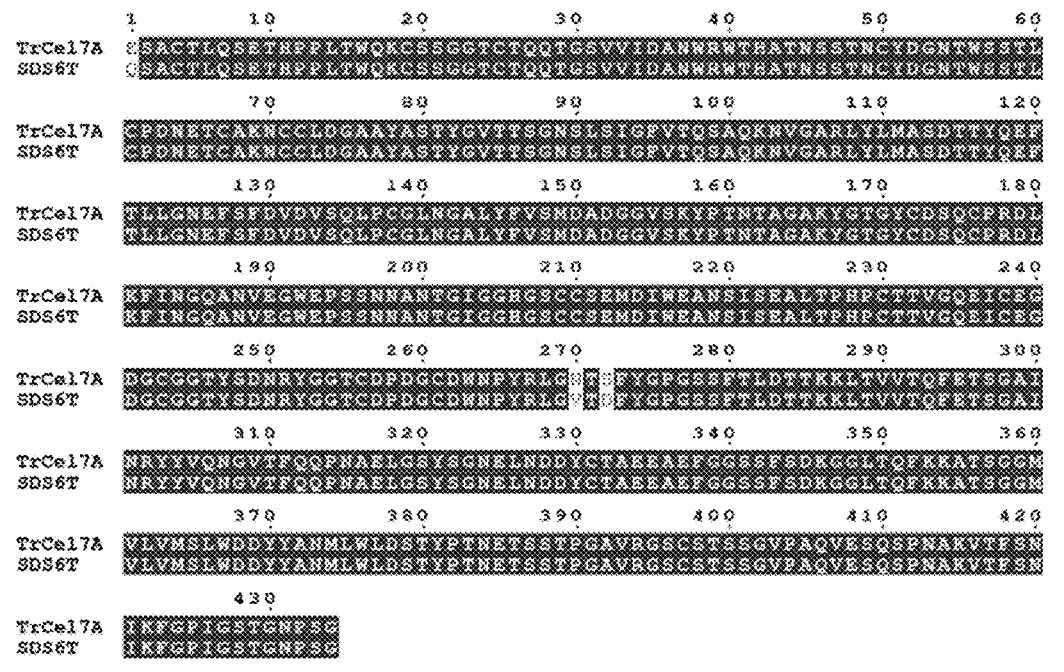

FIG. 13 depicts a portion of the amino acid sequence of the SDS6T mutant Cel7A compared to a portion of the full amino acid sequence of the wildtype *T. reesei* Cel7A parent (TrCel7A) SEQ ID NO: 37 as depicted in FIG. 19.

Figure 14:
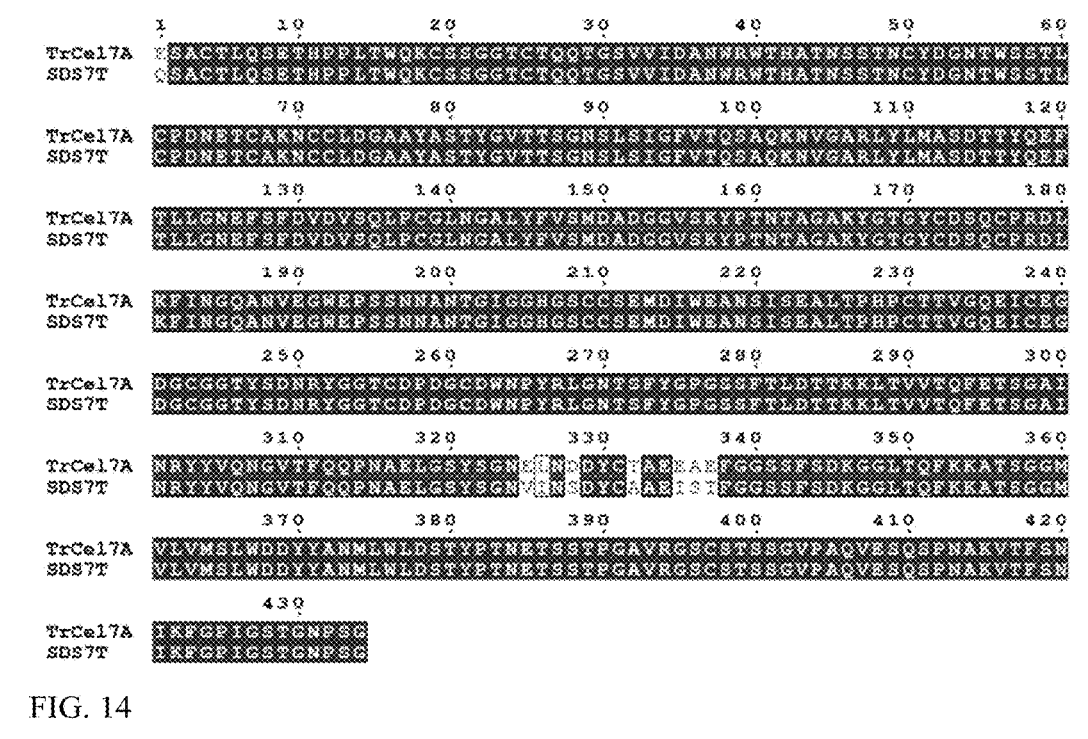

FIG. 14 depicts a portion of the amino acid sequence of the SDS7T mutant Cel7A compared to a portion of the full amino acid sequence of the wildtype *T. reesei* Cel7A parent (TrCel7A) SEQ ID NO: 37 as depicted in FIG. 19.

FIG. 15A depicts a front view. FIG. 15B depicts a back view. FIG. 15C depicts SDS1. FIG. 15D depicts SDS3.

FIG. 19 depicts the parent amino acid sequence (SEQ ID NO: 37) of Cel7A (TrCel7A) from *Trichoderma reesei* from which sequences of mutants depicted in part in FIGS. 8-14 were compared to.

DETAILED DESCRIPTION

Disclosed herein are Cel7A mutants that exhibit higher cellulase activities on a range of cellulose-containing substrates. Also disclosed are methods for degrading cellulose in cellulose-containing materials such as biomass by contacting the cellulases described herein with the cellulose-containing materials. Further disclosed are methods for generating mutant Cel7A polypeptides and assays for determining cellulase activities. In an embodiment, the native protein sequence of *T. reesei* Cel7A is SEQ ID NO: 37 as depicted in FIG. 19.

Figure 1:
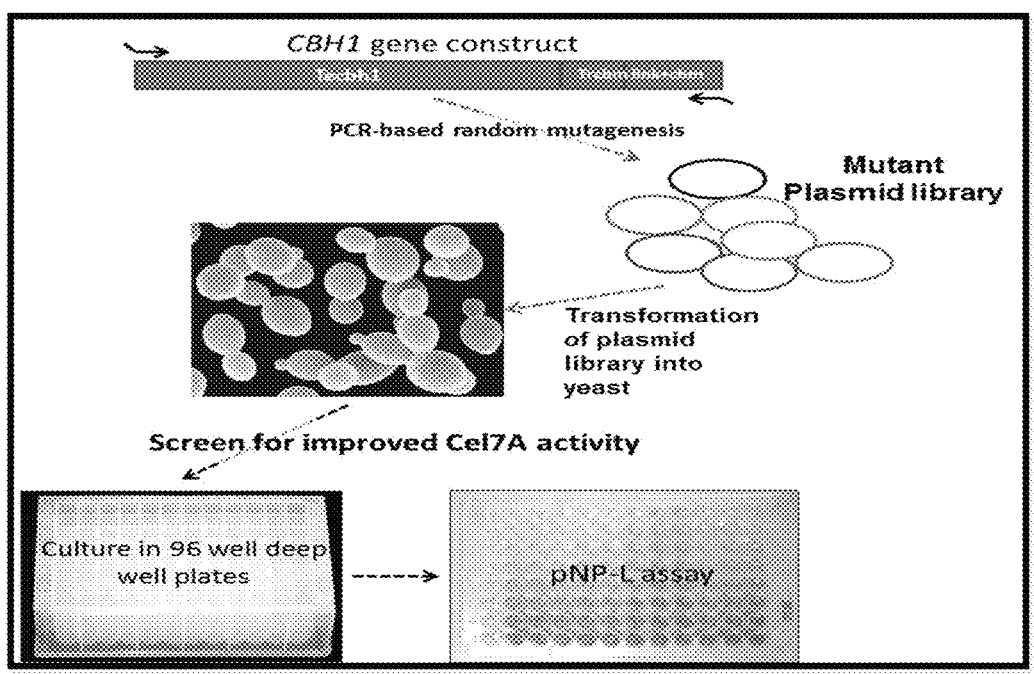
FIG. 1 depicts the experimental approach for screening mutants for pNP-L activity.

A random evolution approach was used to screen and identify Cel7A mutants with improved cellulase activities. Point mutations were introduced into the fusion CBH1 gene (SEQ ID NO: 1) (*Talaromyces emersonii* cat and *Trichoderma reesei* linker-cbm) using error-prone mutagenesis. The mutagenesis library was transformed into a yeast strain followed by selection on cellulosic substrates, as shown in FIG. 1. Transformants were screened using 4-nitrophenyl β-D-lactopyranoside (pNP-L) conversion assay as a measure of cellobiohydrolase activity.

*S. cerevisiae* cells were transformed with different β-glucosidase constructs and were grown on cellobiose containing medium. Differences in size of the colonies indicate the relative β-glucosidase activities of the individual β-glucosidase enzyme. Two high expressing β-glucosidases were identified from four tested different β-glucosidase genes. β-glucosidase from *Aspergillus aculeatus* was found to be most actively expressed one in the tested yeast strains. Higher activity of the *A. aculeatus* β-glucosidase directly correlated with the levels of expression in the two yeast strains tested.

Exemplary Mutations

Two random mutagenesis libraries (high and medium mutation frequency), originating from 8000 clones was generated using the GeneMorph II kit. In one experiment, mutations ranging from 1-19 mutations were observed in the 17 clones suggesting successful Tecbh1-Trcbm1 library synthesis. Of the 17 clones, 12 of them had one/more mutations in the Tecbh1 domain.

In another analysis, 600 yeast transformants were screened by pNP-L activity assay, of which 14 colonies showed significantly higher pNP-L activity, in comparison to the vector-only transformants. Three library clones were sequenced, and clone 1-11, which exhibited the highest pNP-L activity contains a L371M mutation. Clone 1-51 is a truncated Cel7A protein and Clone 1-59 has a single D92E mutation. The L371M mutation is located at the junction of the two catalytic arms of the fusion cbh protein, suggesting a possible important functional implication for the Cel7A enzyme.

Mutant clones were identified that conferred high pNP-L activity to the extracellular yeast medium. The specific mutations were identified and were transferred to *T. reesei* (also called *H. jecorina*) Cel7A at the corresponding positions and were further studied for their ability to improve pNP-L activity of this protein. As discussed further in the Examples below, certain mutants exhibit higher pNP-L activity (e.g., up to 2.3-fold) when compared against native *T. reesei* Cel7A. Additionally, the mutants' activity towards cellulosic substrate was also assayed, which showed that some mutants exhibited higher substrate conversion efficiency, in comparison to the wild-type (WT) Cel7A.

Figure 18:
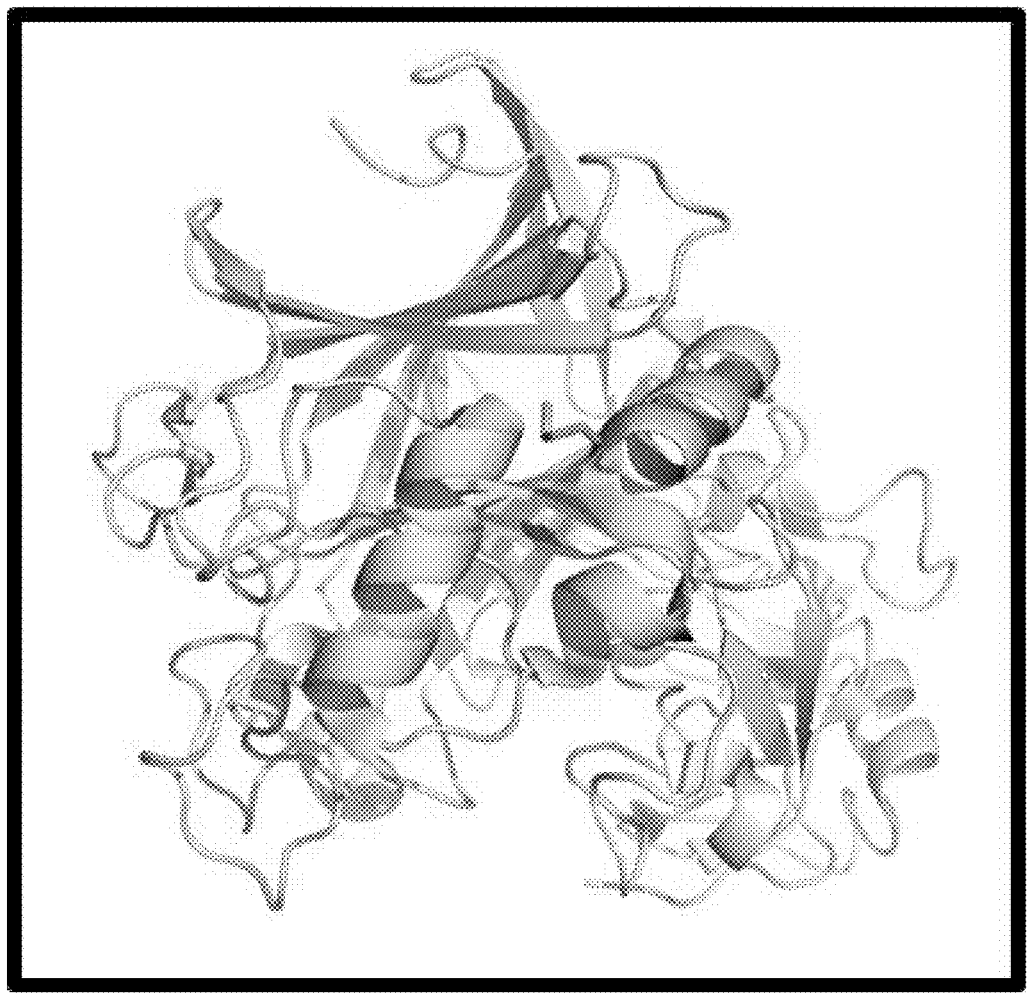
FIG. 18 depicts the location of the L371M mutation of Tr 1-11, also known as clone 1-11.

Clone 1-11 (also known as Tr 1-11) had one mutation (from the parent sequence SEQ ID NO: 2) L371M with the Tecbh1 catalytic domain being affected. The location of the L371M mutation is depicted in FIG. 18. Clone 1-51 had fifteen mutations; C43S, Y78Y, C79S, 99-stop, and 11 downstream mutations from SEQ ID NO: 2 with the Tecbh1 catalytic domain being affected. Clone 1-59 had one mutation (from SEQ ID NO: 2) D92E with the Tecbh1 catalytic domain being affected.

Additional mutations were made and are described in the Examples below. Also included are sub-domain mutants in TrCel7A.

SDS1—removal of disulfide present in TrCel7A via two mutations: C4G and C72A.

SDS2—G427N mutation to add N-glycan attachment site present in PfCel7A.

SDS3—three, point deletions shorten the A1 loop as it is in PfCel7A: A100, Q101, K102.

SDS4—add extra loop into TrCel7A that is present in PfCel7A: insert sequence GTSTGSLS following residue G298 in TrCel7A.

SDS5—three, point mutations remove N-glycan attachment site: N64D, E65A, T66S.

SDS6—three, point mutations remove N-glycan attachment site: N270V, T271T, S272D.

SDS7—several point mutations made near the product sites to match the motif(s) found in PfCel7A. TrCel7A numbering, the string of mutations begins at residue 325 and at residue 337. ELNDDYCTAEEAE is changed to VINSDYCAAEIST.

Yeast cells may be grown in any rich media (e.g., YPD) or minimum media conventionally used in the field. YPD medium contains about 1% yeast extract, 2% peptone and 2% dextrose. Yeast minimum media typically contains 0.67% of yeast nitrogen base ("YNB") without amino acids supplemented with appropriate amino acids or purine or pyrimidine bases. An amount of sugar, typically 2% unless otherwise indicated, may be used as carbon source, including glucose (dextrose), xylose, galactose, maltose or L-arabinose, among others.

In certain embodiments, a nucleic acid may be identical to the sequence represented herein. In other embodiments, the nucleic acids may be least about 80%, 81%, 82%, 83%, 84%, 85%, 86%, 87%, 88%, 89%, 90%, 91%, 92%, 93%, 94%, 95%, 96%, 97%, 98% or 99% identical to a nucleic acid sequence presented herein, or 80%, 81%, 82%, 83%, 84%, 85%, 86%, 87%, 88%, 89%, 90%, 91%, 92%, 93%, 94%, 95%, 96%, 97%, 98% or 99% identical to a nucleic acid sequence presented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

The nucleic acid molecules exemplified herein encode polypeptides with amino acid sequences represented herein. In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the reference amino acid sequence while possessing the function. The present disclosure encompasses yeast cells such as S. cerevisiae cells that contain the nucleic acid molecules described herein, have genetic modifications to the nucleic acid molecules, or express the polypeptides described herein.

Suitable vectors for gene expression may include (or may be derived from) plasmid vectors that are well known in the art, such as those commonly available from commercial sources. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including algal, bacterial, yeast, and mammalian vectors, have been described for replication and/or expression in various host cells or cell-free systems, and may be used with genes encoding the enzymes described herein for simple cloning or protein expression.

Certain embodiments may employ promoters or regulatory operons. The efficiency of expression may be enhanced by the inclusion of enhancers that are appropriate for the particular cell system that is used, such as those described in the literature. Suitable promoters also include inducible promoters. Expression systems for constitutive expression in yeast cells are available from commercial sources. Inducible expression systems are also suitable for use.

In exemplary embodiments, the host cell may be a microbial cell, such as a yeast cell or an algal cell, and may be from any genera or species of algae that is known to produce lipids or is genetically manipulable. Exemplary microorganisms include, but are not limited to, bacteria; fungi; archaea; protists; eukaryotes, such as algae; and animals such as plankton, planarian, and amoeba.

Host cells may be cultured in an appropriate fermentation medium. An appropriate, or effective, fermentation medium refers to any medium in which a host cell, including a genetically modified microorganism, when cultured, is capable of growing and/or expressing recombinant proteins. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors or photobioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing yeast cells, for example, are available from ATCC.

Example 1: Generation of Random Mutagenesis Library

In order to generate a random mutagenesis library of our chimeric CBH protein, the GeneMorph II kit from Agilent Technologies was used. Two independent libraries were generated targeting different mutation frequencies: (1) a medium mutation frequency library (~4.5-9 mutations per kb) and (2) a high mutation frequency library (>9 mutations per kb). To generate the medium and high frequency libraries, 100 ng and 0.1 ng of template DNA, respectively, was PCR amplified using primers SV-Tecbh1-EcoRI-F (CACTAAATCAAAGAATTCATGC) and SV-Trcbm1-XhoI-R (CTCTCGAGGGCGCGCCTA). Plasmid pMI529 was amplified with primers SV-pMI529-XhoI-F (CCCTC-GAGAGCTTTTGAT) and SV-pMI529-EcoRI-R (TGAAT-TCTTTGATTTAGTGTTTGTG). Both the library and the plasmid backbone PCRs were digested with XhoI and EcoRI restriction enzymes and gel purified (Zymo Research, Zymoclean Gel DNA Recovery Kit). Both libraries were ligated into vector pMI529 using T4 DNA Ligase (NEB, Inc.). Ligations were diluted 1:5 in H2O and 2 µL was electroporated into DH5α electromax cells (ThermoFisher), four times for each library. Transformations were plated onto LB-carbenicillin (100 µg/mL) agar plates and approximately 4,000 colonies arose from each library (~8,000 colonies total). Importantly, only ~80 colonies formed on the "no-insert ligation" control suggesting a low background present in the library. Colonies from both libraries were harvested and pooled collectively by spreading LB broth atop the plates and pipetting into 250 mL of LB in a 1 L shake flask. Cells were allowed to grow for 2 hours at which point freezer aliquots were made and the remaining plasmid library was purified using a Maxiprep Kit (Qiagen).

Example 2: Mutation Rate Determination in the Mutagenesis Library

In order to determine the rate of mutation introduced by this mutagenesis technique, 17 bacterial clones were selected (9 from the high mutation library and 8 from the medium mutation library) for sequencing. DNA sequencing revealed that 15 of the 18 clones had mutations ranging from 1-19 mutations. Three clones from the medium mutation library did not contain any mutations. The mutations ranged from 1-5 in numbers in this library. The types of mutations included missense (13) and silent (1) mutations. Clones M1, M5, M9 and M10 had mutations in the Tecbh1 domains, M6 and M7 had a single mutation in the Trcbh1 linker region, and M1 had a point mutation in the Trcbm domain. Conversely, mutations in the high mutation library ranged from 1-19 mutations. The types of mutations in this library included missense (47), silent (6) and nonsense (1) mutations. In addition, one clone had an insertion (clone H8) and a deletion (clone H2) mutation leading to a frame-shift downstream of the mutation. The nucleotide and the amino acid sequences of the unmutated sequences are presented in FIG. 2, while the mutant clones are presented in FIGS. 3 and 4, respectively. The nucleotide changes in each mutant clone, their respective position and the corresponding amino acid change resulting from the mutation and their respective positions are presented in Table 1.

TABLE 1

Details of mutations and their respective locations in the nucleotide and the amino acid sequences in the representative E. coli mutant library clones.

| Library clone # | Change in nucleotides | Nucleotide position altered | AA change at the respective nucleotide position | AA position altered |
|---|---|---|---|---|
| H1 (SEQ ID NOs: 3, 20) | G-A | 76 | A-T | 26 |
| H2 (SEQ ID NOs: 4, 21) | G-A | 640 | A-T | 214 |
| | C-A | 654 | I-I | 218 |
| | C | 1254 | Deletion | 419 |
| | C-A | 1512 | NA (frame shift) | NA (frame shift) |
| H3 (SEQ ID NOs: 5, 22) | G-A | 340 | V-I | 114 |
| | A-T | 602 | E-V | 201 |
| | G-A | 674 | C-Y | 225 |
| | C-A | 1089 | D-E | 363 |
| | A-G | 1184 | Q-R | 395 |
| | A-G | 1303 | N-D | 435 |
| | C-T | 1391 | T-I | 464 |
| | G-A | 1496 | C-Y | 499 |
| | G-A | 1514 | C-Y | 505 |
| H4 (SEQ ID NOs: 6, 23) | T-A | 109 | C-S | 37 |
| | A-T | 383 | D-V | 128 |
| | G-A | 442 | V-M | 148 |
| | T-A | 474 | A-A | 158 |
| | C-A | 860 | S-Y | 287 |
| | G-T | 931 | D-Y | 311 |
| H5 (SEQ ID NOs: 7, 24) | C-A | 285 | D-E | 96 |
| | A-T | 744 | P-P | 247 |
| | G-A | 805 | G-S | 269 |
| | T-A | 832 | F-I | 278 |
| | C-T | 938 | T-I | 313 |
| | A-C | 960 | E-D | 320 |
| | T-A | 1157 | M-K | 386 |
| | G-C | 1204 | D-H | 402 |
| | A-C | 1223 | D-A | 408 |
| | C-T | 1229 | T-I | 410 |
| | G-A | 1243 | A-T | 415 |
| | G-A | 1250 | G-D | 417 |
| | C-A | 1268 | S-Y | 423 |
| | T-A | 1354 | F-I | 452 |
| | A-T | 1367 | N-I | 456 |
| | G-T | 1376 | G-V | 459 |
| | A-T | 1384 | R-stop | 462 |
| | A-T | 1419 | T-T | 473 |
| | G-T | 1456 | G-C | 486 |
| H6 (SEQ ID NO: 8) | G-T | 11 | R-I | 4 |
| | C-A | 116 | A-D | 39 |
| | G-A | 302 | G-D | 101 |
| | T-C | 393 | T-T | 131 |
| | G-A | 756 | M-I | 252 |
| | G-A | 1126 | A-T | 376 |
| | A-G | 1417 | T-A | 473 |

TABLE 1-continued

Details of mutations and their respective locations in the nucleotide and the amino acid sequences in the representative *E. coli* mutant library clones.

| Library clone # | Change in nucleotides | Nucleotide position altered | AA change at the respective nucleotide position | AA position altered |
|---|---|---|---|---|
| H8 (SEQ ID NOs: 9, 25) | T-A | 630 | S-S | 210 |
| | A | 1051 | Insert | 351 |
| | G-A | 1167 | NA (frame shift) | NA (frame shift) |
| | C-T | 1203 | NA (frame shift) | NA (frame shift) |
| | T-C | 1363 | NA (frame shift) | NA (frame shift) |
| | C-A | 1370 | NA (frame shift) | NA (frame shift) |
| | A-T | 1396 | NA (frame shift) | NA (frame shift) |
| | T-A | 1447 | NA (frame shift) | NA (frame shift) |
| | T-G | 1495 | NA (frame shift) | NA (frame shift) |
| H10 (SEQ ID NOs: 10, 27) | C-T | 146 | A-V | 49 |
| | G-A | 190 | G-S | 64 |
| | A-G | 352 | N-D | 118 |
| | T-A | 559 | C-S | 187 |
| | T-A | 593 | I-N | 198 |
| | C-A | 629 | S-Y | 210 |
| | G-A | 671 | C-Y | 224 |
| | G-A | 1090 | D-N | 364 |
| | T-A | 1416 | T-T | 472 |
| M1 (SEQ ID NOs: 11, 28) | A-G | 1049 | E-G | 350 |
| | G-A | 1124 | G-D | 375 |
| | C-T | 1170 | D-D | 390 |
| | C-T | 1442 | T-I | 481 |
| M3 (SEQ ID NOs: 12, 29) | No mutations | | | |
| M4 (SEQ ID NOs: 13, 30) | No mutations | | | |
| M5 (SEQ ID NOs: 14, 31) | G-A | 142 | G-S | 48 |
| | C-A | 938 | T-N | 313 |
| M6 (SEQ ID NOs: 15, 32) | C-T | 1433 | P-L | 478 |
| M7 (SEQ ID NOs: 16, 33) | T-C | 1429 | S-P | 477 |
| M8 (SEQ ID NOs: 17, 34) | No mutations found | | | |
| M9 (SEQ ID NOs: 18, 35) | C-A | 743 | P-Q | 248 |
| M10 (SEQ ID NOs: 19, 36) | C-T | 113 | T-I | 38 |
| | T-A | 511 | S-T | 171 |
| | G-C | 676 | A-P | 226 |
| | G-A | 935 | G-D | 312 |
| | G-A | 1079 | G-D | 360 |

Overall, 82% of the clones in the sequenced library had mutations at different frequencies. A table summarizing the types of mutations in the different clones is shown in Table 2.

TABLE 2

Details of the sequenced clones from the Tecbh1-Trcbm1 random mutagenesis library.

| Mutant clone | Total # | Missense mutation | Silent mutation | Nonsense mutation | Insertion | Deletion | Mutations in Tecbh1 | Mutations in Trlinker | Mutations in Trcbm |
|---|---|---|---|---|---|---|---|---|---|
| H1 | 1 | 1 | 0 | 0 | 0 | 0 | 1 | 0 | 0 |
| H2* | 4 | 1 | 1 | 0 | 0 | 1 | 2 | 0 | 1 |
| H3 | 9 | 9 | 0 | 0 | 0 | 0 | 6 | 1 | 2 |
| H4 | 6 | 5 | 1 | 0 | 0 | 0 | 6 | 0 | 0 |
| H5 | 19 | 16 | 2 | 1 | 0 | 0 | 14 | 4 | 1 |
| H6 | 7 | 6 | 1 | 0 | 0 | 0 | 6 | 1 | 0 |
| H8 | 9 | 1 | 0 | 0 | 1 | 0 | 7 | 1 | 1 |
| H10 | 9 | 8 | 1 | 0 | 0 | 0 | 9 | 0 | 0 |
| M1 | 4 | 3 | 1 | 0 | 0 | 0 | 3 | 0 | 1 |
| M3 | 0 | 0 | 0 | 0 | 0 | 0 | 0 | 0 | 0 |

TABLE 2-continued

Details of the sequenced clones from the Tecbh1-Trcbm1 random mutagenesis library.

| Mutant clone | Total # | Missense mutation | Silent mutation | Nonsense mutation | Insertion | Deletion | Mutations in Tecbh1 | Mutations in Trlinker | Mutations in Trcbm |
|---|---|---|---|---|---|---|---|---|---|
| M4 | 0 | 0 | 0 | 0 | 0 | 0 | 0 | 0 | 0 |
| M5 | 2 | 2 | 0 | 0 | 0 | 0 | 2 | 0 | 0 |
| M6 | 1 | 1 | 0 | 0 | 0 | 0 | 0 | 1 | 0 |
| M7 | 1 | 1 | 0 | 0 | 0 | 0 | 0 | 1 | 0 |
| M8 | 0 | 0 | 0 | 0 | 0 | 0 | 0 | 0 | 0 |
| M9 | 1 | 1 | 0 | 0 | 0 | 0 | 1 | 0 | 0 |
| M10 | 5 | 5 | 0 | 0 | 0 | 0 | 5 | 0 | 0 |

*indicates the sum of different types of mutations does not add up to the total number of mutations, since the deletion results in change of amino acid sequence downstream of the deletion site.
H and M represent individual clones from the "high" and "medium" library. "Te" represents *Talaromyces emersonii*. "Tr" represents *Trichoderma reesei*.

Example 3: Screening and Identification of Improved Cel7A Mutants

Figure 5:
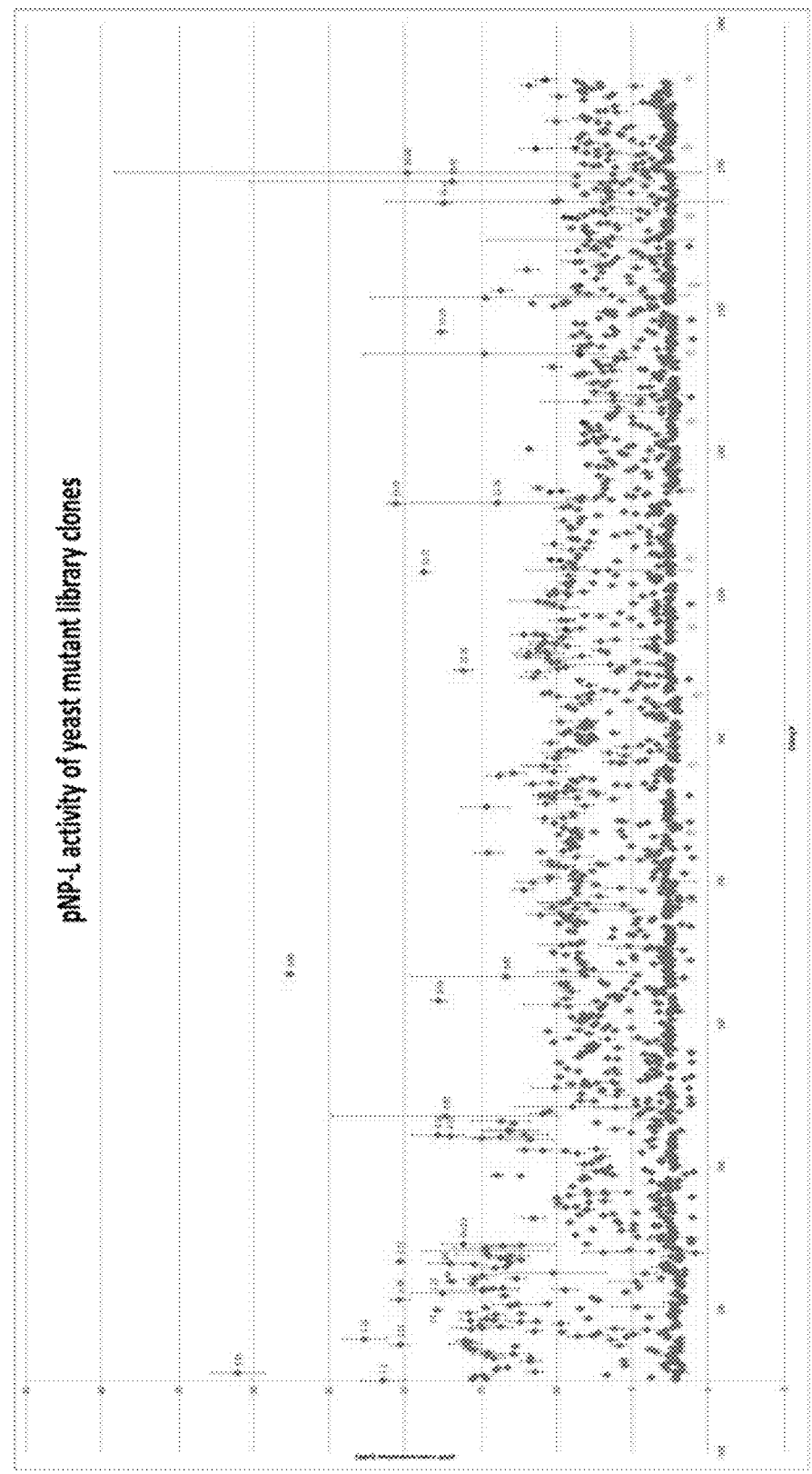
FIG. 5 depicts the pNP-L activity of the yeast transformed with mutant sequences.

The library of CBH mutants was transformed into the yeast strain Y294 expressing a heterologous β-glucosidase from *Aspergillus aculeatus* and selected on synthetic complete medium lacking tryptophan and uracil (SCD-trp-ura). A total of 2000 clones were transferred to 96 well plates containing SCD-trp-ura medium. pNP-L activity assay was performed on the extracellular broth to identify transformants that displayed higher pNP-L activity than the vector-only transformed control. Twenty-two yeast transformants were identified that showed higher pNP-L activity than the controls (FIG. 5). Each of these transformants was subjected to DNA extraction using Quick-DNA Fungal/Bacterial Miniprep kit. Each of the 22 DNA preparations were transformed into *E. coli* Zymo 5α cells to select for the individual plasmids that confer the improved pNP-L activity to the yeast cells. Plasmid DNA was then extracted from the *E. coli* transformants and sequenced to identify the Cel7A mutations in these plasmids.

DNA sequencing of the plasmids revealed 0-11 mutations in these mutants. These mutations included two plasmids with no mutations, 11 plasmids with 1 mutation, two plasmids with 2 mutations, 4 plasmids with 3 mutations, and one plasmids each with 4, 8, and 11 mutations. One of the 22 mutants involved a frameshift which led to truncation of the protein. A table summarizing the types of mutations in each of the mutant plasmids are presented in Table 3.

TABLE 3

Summary of mutations in the high pNP-L active yeast clones.

| Mutants | # of mutations | Missense | Silent mutations | Insertions | Deletions | Nonsense | Frameshift |
|---|---|---|---|---|---|---|---|
| 19-47a | 0 | 0 | 0 | 0 | 0 | 0 | None |
| 13-77b | 0 | 0 | 0 | 0 | 0 | 0 | None |
| 1-11 | 1 | 0 | 0 | 0 | 0 | 0 | None |
| 1-59 | 1 | 1 | 0 | 0 | 0 | 0 | None |
| 2-4c | 1 | 1 | 0 | 0 | 0 | 0 | None |
| 2-69c | 1 | 1 | 0 | 0 | 0 | 0 | None |
| 19-17b | 1 | 1 | 0 | 0 | 0 | 0 | None |
| 19-29b | 1 | 0 | 1 | 0 | 0 | 0 | None |
| 19-60b | 1 | 1 | 0 | 0 | 0 | 0 | None |
| 13-78a | 1 | 1 | 0 | 0 | 0 | 0 | None |
| 12-77 | 1 | 1 | 0 | 0 | 0 | 0 | None |
| 11-35a | 1 | 1 | 0 | 0 | 0 | 0 | None |
| 4-83b | 1 | 0 | 1 | 0 | 0 | 0 | None |
| 1-1d | 2 | 1 | 1 | 0 | 0 | 0 | None |
| 4-56a | 2 | 1 | 1 | 0 | 0 | 0 | None |
| 2-27a | 3 | 2 | 1 | 0 | 0 | 0 | None |
| 6-87a | 3 | 1 | 2 | 0 | 0 | 0 | None |
| 6-53a | 3 | 3 | 0 | 0 | 0 | 0 | None |
| 2-18c | 3 | 2 | 1 | 0 | 0 | 0 | None |
| 1-51 | 4 | 3 | 1 | 0 | 0 | 1 | None |
| 2-72b | 8 | 6 | 1 | 0 | 1 | 0 | Yes |
| 6-90a | 11 | 10 | 1 | 0 | 0 | 0 | None |

Example 4: Down-Selection of Mutants for Testing in *T. reesei* Cel7A

Figure 6:
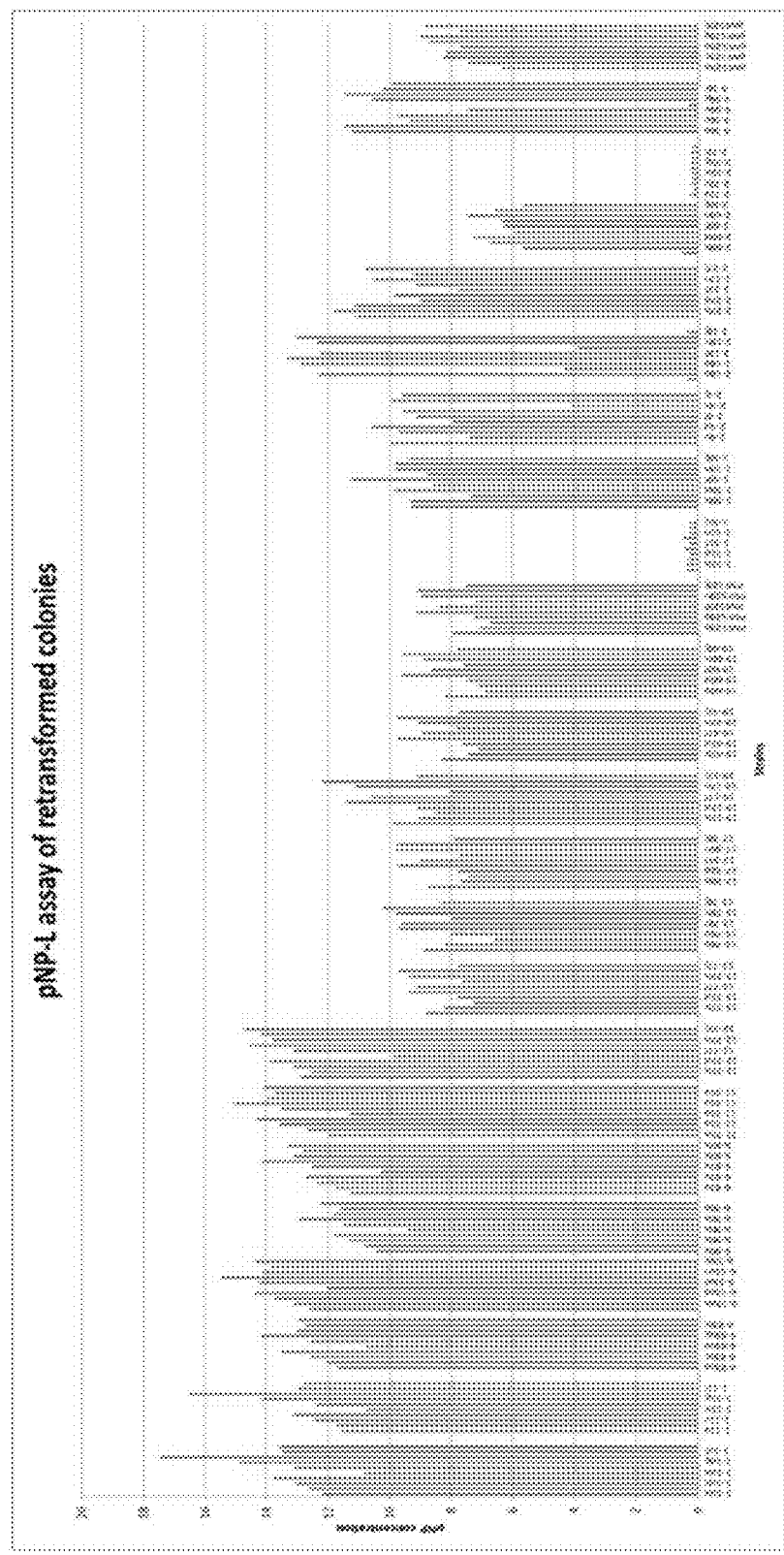
FIG. 6 depicts the pNP-L activity of the yeast after retransformation with mutant sequences.

Each of the 22 plasmids that were extracted from high-pNP-L active clones were retransformed into the yeast strain Y294 expressing a heterologous β-glucosidase from *Aspergillus aculeatus* in order to verify the mutant's ability to confer higher pNP-L activity to the yeast broth. Ten individual colonies were picked for determining the pNP-L activity of each mutant. The activity of each of the yeast colonies towards pNP-L substrate is presented in FIG. 6. Of the 22 mutants, we identified 10 mutants that showed high pNP-L activity tested from the extracellular medium. These mutants were designated 1-1d, 1-11, 4-56a, 6-90c, 6-87a, 12-77, 11-35a, 4-83b, 6-53a, and 2-18c. Mutant 4-83b contained only a silent mutation, so this mutant was not subjected to further analysis.

Example 4: Transferring Mutations to *T. reesei* Cel7A for Activity Analysis The wild-type (wt) TrCel7A sequence was aligned with all the high-pNP-L activity sequences in order to identify the corresponding positions of mutations in TrCel7A. Without being bound by theory, these mutations should result in improving pNP-L activity of TrCel7A. PCR-based point mutagenesis or gene synthesis was used to generate the corresponding 9 TrCel7A mutants. A table representing the positions and the type of mutations in Tecbh1-Trcbm1 and TrCel7A are presented in Table 4.

TABLE 4

Point mutations in Tecbh1-Trlnk-Trcbm1 clones and corresponding mutations in the TrCel7A sequence.

| Mutants | Location of mutations in Tecbh1TrlnkTrcbm (with secretion signal) | Location of mutations in TrCel7A (with secretion signal) | Location of mutations in TrCel7A (without secretion signal) |
|---|---|---|---|
| 1-11 | L371M | L366M | L349M |
| 1-1d | A239V | A241V | A224V |
| 4-56a | T481I | T479I | T462I |
| 6-87a | D272V | D274V | D257V |
| 12-77 | V385A | V380A | V363A |
| 11-35a | G463D | G461D | G444D |
| 6-53a | L111M | I110M | I93M |
|  | Y281N | Y283N | Y266N |
|  | T464I | T462I | T445I |
| 2-18c | T411S | T406S | T389S |
|  | A394V | A389V | A372V |

The mutation 6-90a (10 missense and one silent mutation) is not included in the table. The TrCel7A constructs were introduced into the vector pTrEno, such that they were under the control of the ENO gene promoter and the TrCBH2 terminator. Plasmids were transformed into the cbh1 deleted strain AST1116 (derived from QM6a) by electroporation. Briefly, competent spores were prepared as described in Linger et al., Biotechnol Biofuels 8:45 (2015), which involved time-specific sporulation on PDA, followed by re-sporulation, collection and washing of spores before freezing at −80° C. as electro-competent spore stocks. Five µg of plasmid was linearized with SbfI and further purified using DNA clean and concentrator-5 kit (Zymo Research Corp, Irvine, Calif.). Frozen competent spores were thawed on ice and mixed with ~1.0 µg of the linearized plasmid. Electroporation was carried out using a BioRad Gene Pulser (BioRad Laboratories, Inc., Hercules, Calif.) using the following conditions: 1.8 kV, 25 µF, 800Ω, and incubated for a few minutes on ice. One mL of 'complete medium lactose' medium was then added to the transformation mixture and transferred to six-well tissue culture plates and incubated at room temperature for 18 hours to allow recovery and germination of spores. Two hundred µL of this cell suspension was then plated on to potato dextrose agar containing 100 µg/mL hygromycin and 0.1% (v/v) Triton X-100 for colony size restriction (PDHX) and incubated at 30° C. in lighted incubator for 2-3 days to allow colony development.

Example 5: Screening of Transformants for Cel7A Expression by Western Blotting

A small piece of mycelial fragment from transformant colonies grown on PDHX plates was transferred to 2 mL of Mandels Andreotti minimal medium containing 5% glucose (MAG) and hygromycin (100 µg/mL) in a 24-well microtiter plate and incubated statically in a lighted 30° C. incubator for 3 days until a mycelial mat was observed on the liquid medium. Fifteen µL of cell free culture broth (containing secreted proteins) was transferred to microcentrifuge tubes containing 5 µL SDS-PAGE loading buffer and subjected to boiling at 95° C. for 10 min. This protein extract was separated on 4-12% NuPAGE gel in MOPS buffer, 200V constant for 50 minutes. Post-separation, proteins were electro-transferred onto PVDF membrane for Western blot analysis using an iBlot2 (Thermo Fisher Scientific, Inc. Grand Island, N.Y.). For hybridization of Cel7A protein, a *P. funiculosum* anti-Cel7A polyclonal antibody raised in rabbit was used as primary antibody at a dilution of 1:20,000. Detection of Cel7A was carried out using alkaline phosphatase-conjugated anti-rabbit secondary antibody (Thermo Fisher Scientific, Inc. Grand Island, N.Y.). Colonies displaying hybridization were subjected to clonal isolation by restreaking a spore suspension from the transformants onto hygromycin selection plates. Five individual colonies arising from this restreak were inoculated into MAG medium containing hygromycin, followed by Western blotting again to confirm the expression of Cel7A in these individual colonies.

Example 6: Cel7A Purification

Cel7A was purified as described in Linger et al., Biotechnol Biofuels 8:45 (2015). Briefly, fermentation broths (~8 to 10 L) were harvested, vacuum filtered, concentrated, and then loaded onto a 26/10 Phenyl Sepharose Fast Flow column. Buffer A was 20 mM Bis-Tris pH 6.5 and buffer B was 20 mM Bis-Tris pH 6.5, 2.0 M $(NH_4)_2SO_4$. After binding and washing, a descending gradient of 80% B (1.6 M $(NH_4)_2SO_4$) to 0% B over eight column volumes was used to elute the bound proteins from the column. Active fractions were identified by a p-nitrophenyl-β-(1-4)-D-lactopyranoside (pNP-L) activity assay. The pNP-L-active fractions were pooled and concentrated as needed. Protein was desalted and exchanged into 20 mM Bis-Tris buffer pH 6.5. This sample was then loaded onto a Tricorn 10/100 anion exchange column packed with Source 15Q and eluted with a 0-50% salt gradient over 30 column volumes. Buffers were 20 mM Bis-Tris pH 6.5 (A) and the same supplemented with 1.0 M NaCl (B). pNP-L activity was followed again to identify the active fractions. Active fractions were pooled, brought to 1.5 M $(NH_4)_2SO_4$ in 20 mM Bis-Tris pH 6.5, loaded onto a Tricorn 10/100 Source-Iso column, washed, and eluted with a descending gradient from 1.6 to 0.4 M $(NH_4)_2SO_4$. Active fractions were concentrated to <10 mL and subjected to size exclusion chromatography using a 26/60 Superdex 75 column and 20 mM sodium acetate buffer pH 5.0 containing 100 mM NaCl as the mobile phase. All chromatography buffers contained 0.02% (w/v) $NaN_3$ as a microbial inhibitor. SDS-PAGE and anti-Cel7A immunoblotting were performed to assess purity.

Example 7: pNP-Lactopyranoside Assay

The pNP-L assay was performed by incubating 150 µL of 2 mM pNP-L with 25 µL of sample at 45° C. for 30 minutes. Reactions were quenched with 25 µL of 1 M $Na_2CO_3$, and the absorbance at 405 nm was measured. Standard curve concentrations range from 0 to 250 µM pNP-L. For kcat and kM evaluation, the assay was performed with substrate concentration in the range 8 mM-0.133 mM. Reported values were obtained using GraphPad Prism version 7.00 for Mac (GraphPad Software, La Jolla Calif. USA) and are representative of three experiments (Table 5).

TABLE 5

Activity assay of Cel7A mutants on pNP-L substrate.

| Protein | Specific Activity (U/mg) | Relative specific activity (ratio) | $k_{cat}$ (min$^{-1}$) | $K_M$ (mM) |
|---|---|---|---|---|
| TrCel7A WT | 256 ± 24 | 1 | 20 ± 1 | 1,930 ± 112 |
| TrCel7A 1-11 | 170 ± 3 | 0.7 | 10.9 ± 0.2 | 1,065 ± 81 |

TABLE 5-continued

Activity assay of Cel7A mutants on pNP-L substrate.

| Protein | Specific Activity (U/mg) | Relative specific activity (ratio) | $k_{cat}$ (min$^{-1}$) | $K_M$ (mM) |
|---|---|---|---|---|
| TrCel7A 1-1d | 592 ± 18 | 2.3 | 56 ± 4 | 2,403 ± 338 |
| TrCel7A 4-56a | n.a. | n.a. | n.a. | n.a. |
| TrCel7A 6-87a | 212 ± 24 | 0.8 | 24 ± 4 | 1,968 ± 116 |
| TrCel7A 12-77 | 298 ± 21 | 1.2 | n.a. | n.a. |
| TrCel7A 11-35a | 199 ± 3 | 0.8 | 11 | 987 |
| TrCel7A 6-53a | 326 ± 11 | 1.3 | 21 ± 3 | 2,100 ± 213 |
| TrCel7A 2-18c | 388 ± 32 | 1.5 | 28 ± 7 | 1,980 ± 180 |

We observed that among the 8 tested mutants, 4 mutants (1-1d, 12-77, 6-53a and 2-18c) showed higher pNP-L activity in comparison to the wild-type TrCel7A. The increase in specific activity in these mutants ranged from 1.2- to 2.3-fold. The highest specific activity was observed in 1-1d with a specific activity of 592±18 U/mg, which corresponded to 2.3-fold improved pNP-L conversion to pNP.

Example 8: Cel7A Enzyme Activity Measurement

Figure 7:
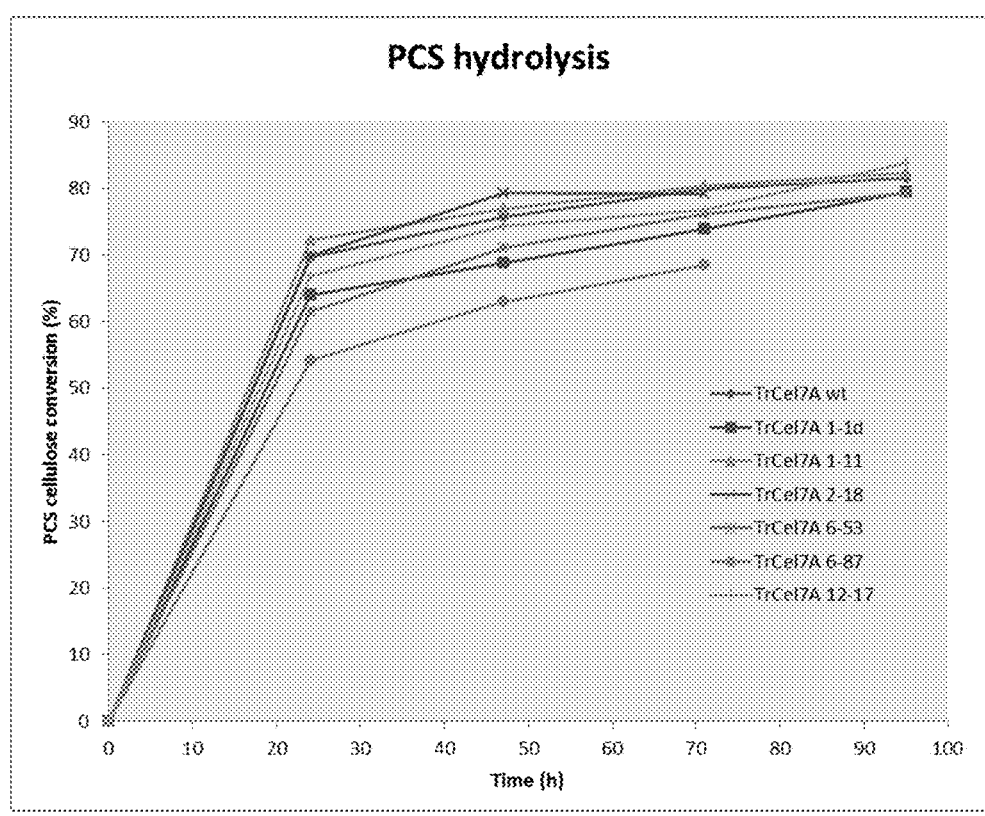
FIG. 7 depicts the cellulase activity of purified Cel7A (WT and mutants) on pretreated corn stover.
Figure 15A:
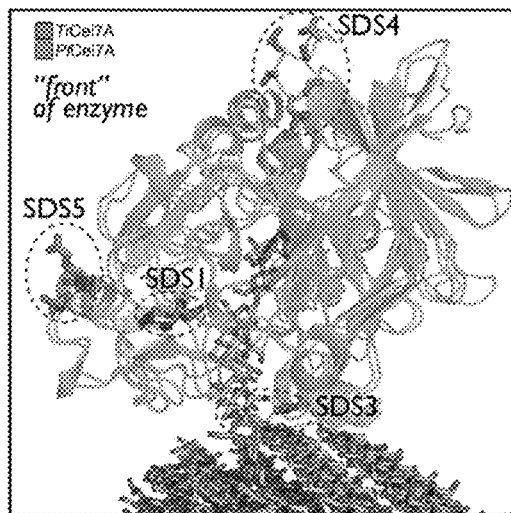
FIGS. 15A, 15B, 15C, and 15D depict a ribbon diagram of Cel7A showing the areas where amino acid residues were altered in the indicated SDS mutants.
Figure 15B:
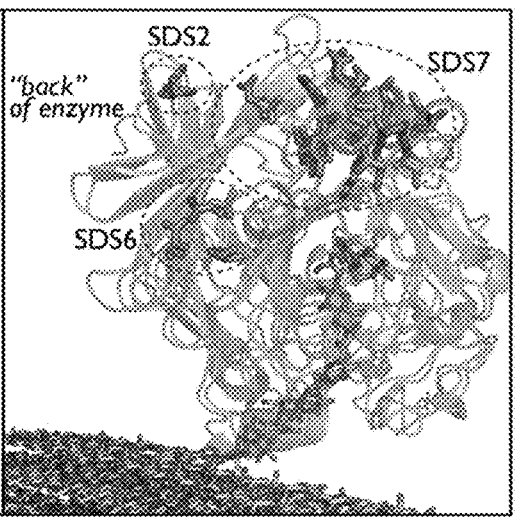
Figure 15C:
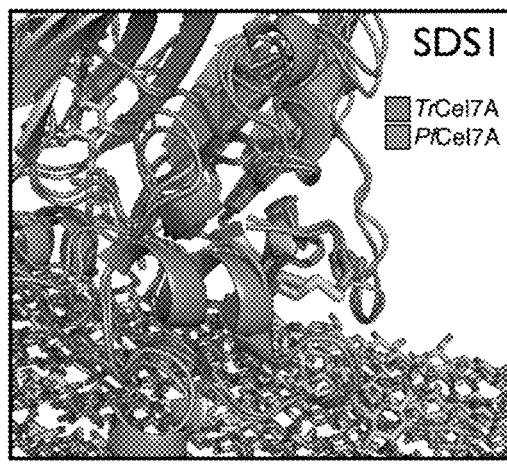
Figure 15D:
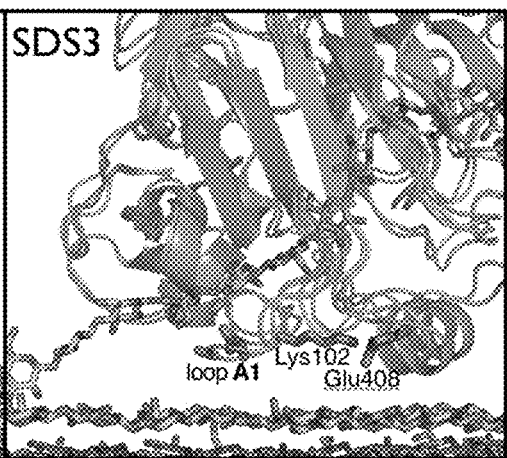
Figure 17:
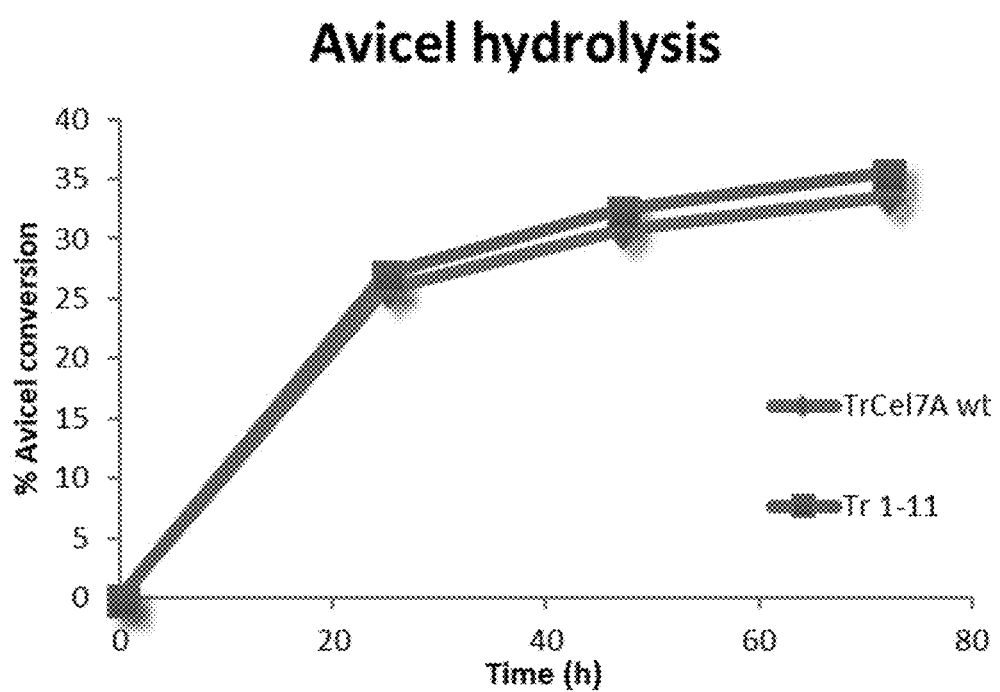
FIG. 17 depicts the cellulase activity of purified Cel7A (WT and mutants) on Avicel. Tr 1-11 is a L371M mutation of wild type Cel7A from *Trichoderma reesei* (SEQ ID NO: 2).

The biomass substrate used in this work is dilute acid-pretreated corn stover (PCS) P120927 prepared and analyzed by the standard National Renewable Energy Laboratory (NREL) laboratory analytical procedures (Chen et al., Bioresour Technol. 401-8 (2013)). The substrate was suspended in 20 mM acetic acid/sodium acetate buffer at pH 5.0. Digestions were conducted at 40° C. in high-performance liquid chromatography (HPLC) vials placed in a rotator at 10 rpm up to 96 hours. An amount of substrate equivalent to 8.5 mg of glucan was added to the enzymatic cocktail made of TrCel7A (wild-type or mutant), endoglucanase I from *Trichoderma longibrachiatum* (Megazyme Co., Bray Ireland), and β-glucosidase from *Aspergillus niger* (Megazyme Co., Bray Ireland) at a concentration of 28.008, 1.894, and 0.5 mg protein/g of glucan, respectively. Adjustment of the biomass assay aliquots to a 1.7 mL final volume resulted in a cellulose concentration of 5.0 mg/mL. Experiments were performed in duplicate. Sugar analyses were performed on an Agilent 1100 LC system equipped with a G1362A refractive index detector (RID). Each sample was injected at a volume of 20 μL into the HPLC-RID system, with the RID held at 55° C. Compounds were separated using a BioRad Aminex HPX-87H column 9 μm, 7.8×300 mm column (BioRad, Hercules, Calif.) at a column temperature of 55° C. The HPLC solvent regime consisted of an isocratic flow of 0.01 N $H_2SO_4$ in water at 0.6 mL/min for a total run time of 27 minutes. A four-point calibration curve ranging from 0.05 mg/mL to 40 mg/mL was used to quantitate the samples. The PCS hydrolysis assay results are presented in FIG. 7. The mutants 1-11 and 2-18 showed higher hydrolysis of the substrate, in comparison to the wild-type TrCel7A, during the initial incubation periods (up to 48 hours). Mutant 1-11 was further tested on the substrate avicel, which showed ~7% higher activity than the wild-type TrCel7A (FIG. 17).

Example 9: Construction of Sub-Domain Swap Library

The PfCel7A crystal structure was solved, and eight areas of the enzyme wherein the structure differed significantly from that of TrCel7A were identified. Each of these motifs was swapped into the corresponding region of the TrCel7A parent (see FIGS. 8-15).

Figure 16:
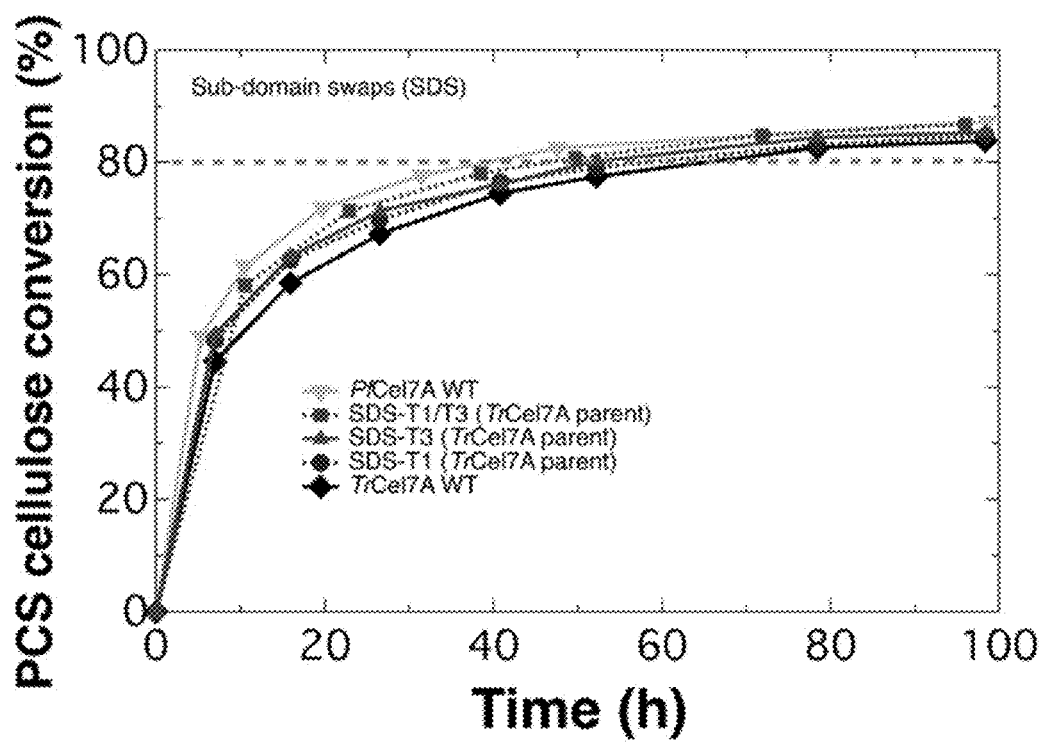
FIG. 16 shows activity of exemplary mutant enzymes on pre-treated corn stover (PCS) compared to wildtype *T. reesei* Cel7A (TrCel7A wt). SDS-T1 and SDS-T3 mutants show increased activity over TrCel7A, while the combined double mutant SDS-T1/T3 shows a larger increase in activity. Activity of wildtype Cel7A from *P. funiculosum* (PfCel7A wt) is also included.

Two of these sub-domain swaps, SDS-T1 (removal of the tenth disulfide bridge) and SDS-T3 (three-residue deletion in the A1 loop), exhibited higher activity on pre-treated corn stover than the WT TrCel7A parent enzyme (FIG. 16), representing a successful instance of cellulase engineering. Combining these two sub-domain swaps into the same mutant enzyme produces an augmented result: with the mutation of two localized regions of the parent enzyme TrCel7A, hydrolytic activity was demonstrated to match that of the PfCel7A WT, representing an improvement of more than 100%, as measured by the time to 80% conversion.

The Examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

What is claimed is:

1. A non-naturally occurring, mutated Cel7A polypeptide having increased hydrolase activity when compared to the naturally occurring Cel7A polypeptide from which the non-naturally occurring mutated Cel7A polypeptide was derived; and
wherein said mutated Cel7A polypeptide has an amino acid sequence identity of at least 85% of SEQ ID NO: 2.

2. The non-naturally occurring mutated Cel7A polypeptide of claim 1 wherein the non-naturally occurring mutated Cel7A polypeptide comprises a L371M mutation of SEQ ID NO: 2.

3. The non-naturally occurring mutated Cel7A polypeptide of claim 1 wherein the non-naturally occurring mutated Cel7A polypeptide comprises a D92E mutation of SEQ ID NO: 2.

4. The non-naturally occurring mutated Cel7A polypeptide of claim 1 wherein the non-naturally occurring mutated Cel7A polypeptide comprises a A239V mutation of SEQ ID NO: 2.

5. The non-naturally occurring mutated Cel7A polypeptide of claim 1 wherein the non-naturally occurring mutated Cel7A polypeptide comprises a T481I mutation of SEQ ID NO: 2.

6. The non-naturally occurring mutated Cel7A polypeptide of claim 1 having up to 2.3 times the hydrolase activity when compared to the naturally occurring Cel7A polypeptide from which the non-naturally occurring mutated Cel7A polypeptide was derived.

7. The non-naturally occurring mutated Cel7A polypeptide of claim 1 having up to 2.3 times the hydrolase activity when compared to the naturally occurring Cel7A polypeptide from which the non-naturally occurring mutated Cel7A polypeptide was derived wherein the non-naturally occurring Cel7A polypeptide comprises a L371M mutation of SEQ ID NO: 2.

8. The non-naturally occurring mutated Cel7A polypeptide of claim 1 having up to 2.3 times the hydrolase activity when compared to the naturally occurring Cel7A polypeptide from which the non-naturally occurring mutated Cel7A polypeptide was derived wherein the non-naturally occurring Cel7A polypeptide comprises a D92E mutation of SEQ ID NO: 2.

9. The non-naturally occurring mutated Cel7A polypeptide of claim 1 having up to 2.3 times the hydrolase activity when compared to the naturally occurring Cel7A polypeptide from which the non-naturally occurring mutated Cel7A polypeptide was derived wherein the non-naturally occurring Cel7A polypeptide comprises a A239V mutation of SEQ ID NO: 2.

10. The non-naturally occurring mutated Cel7A polypeptide of claim 1 having up to 2.3 times the hydrolase activity when compared to the naturally occurring Cel7A polypeptide from which the non-naturally occurring mutated Cel7A polypeptide was derived wherein the non-naturally occurring Cel7A polypeptide comprises a T481I mutation of SEQ ID NO: 2.

11. An isolated nucleic acid molecule encoding the non-naturally occurring mutated Cel7A polypeptide of claim 1.

12. The isolated nucleic acid molecule of claim 11, further comprising a promoter operably linked to the nucleic acid molecule.

13. The isolated nucleic acid molecule of claim 12, wherein the promoter allows expression of the nucleic acid in a filamentous fungal host cell.

14. The isolated nucleic acid molecule of claim 13, wherein the nucleic acid is within an expression vector.

15. A host cell expressing a recombinant polypeptide encoded by the nucleic acid molecule of claim 11.

16. The host cell of claim 15, wherein the cell is a fungal cell.

* * * * *